United States Patent
Ho et al.

(10) Patent No.: US 11,066,479 B2
(45) Date of Patent: Jul. 20, 2021

(54) MONOCLONAL ANTIBODIES TARGETING GLYPICAN-2 (GPC2) AND USE THEREOF

(71) Applicant: The U.S.A., as represented by the Secretary, Department of Health and Human Services, Bethesda, MD (US)

(72) Inventors: Mitchell Ho, Urbana, MD (US); Nan Li, Laurel, MD (US); Dimiter S. Dimitrov, Pittsburgh, PA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 350 days.

(21) Appl. No.: 16/322,712

(22) PCT Filed: Jul. 20, 2017

(86) PCT No.: PCT/US2017/043112
§ 371 (c)(1),
(2) Date: Feb. 1, 2019

(87) PCT Pub. No.: WO2018/026533
PCT Pub. Date: Feb. 8, 2018

(65) Prior Publication Data
US 2020/0216558 A1    Jul. 9, 2020

Related U.S. Application Data

(60) Provisional application No. 62/369,861, filed on Aug. 2, 2016.

(51) Int. Cl.
| C07K 16/30 | (2006.01) |
| A61K 47/69 | (2017.01) |
| A61K 47/64 | (2017.01) |
| A61P 35/00 | (2006.01) |
| C07K 7/08  | (2006.01) |
| C07K 16/28 | (2006.01) |

(52) U.S. Cl.
CPC ...... C07K 16/3053 (2013.01); A61K 47/6415 (2017.08); A61K 47/6929 (2017.08); A61P 35/00 (2018.01); C07K 7/08 (2013.01); C07K 16/2809 (2013.01)

(58) Field of Classification Search
CPC .......... A61K 2039/505; A61K 47/6451; A61K 47/6851; A61K 47/6929; C07K 16/18; C07K 16/2809; C07K 16/30; C07K 16/3053; C07K 2317/569
See application file for complete search history.

(56) References Cited

U.S. PATENT DOCUMENTS

| 9,416,190 B2 * | 8/2016 | Ho .................. G01N 33/57492 |
| 2018/0318444 A1 * | 11/2018 | Maris ..................... C07K 16/18 |
| 2019/0134091 A1 * | 5/2019 | Dropulic ................ A61K 35/15 |
| 2020/0223937 A1 * | 7/2020 | Pastan ................ A61K 47/6849 |

FOREIGN PATENT DOCUMENTS

| WO | WO 2016/201394 | 12/2016 |
| WO | WO 2017/027291 | 2/2017 |
| WO | WO 2017/083296 | 5/2017 |

OTHER PUBLICATIONS

Chen et al., "Construction of a Large Phage-Displayed Human Antibody Domain Library with a Scaffold Based on a Newly Identified Highly Soluble, Stable Heavy Chain Variable Domain," *J. Mol. Biol.*, vol. 382:779-789, 2008.

Dai et al., "Chimeric Antigen Receptors Modified T-Cells for Cancer Therapy," *J. Natl. Cancer Inst.*, vol. 108:1-14, 2016.

Hewes, "Human Monoclonal Antibodies Targeting Glypican-2 in Neuroblastoma," Federal Register, vol. 81:54583, 2016.

Li et al., "Therapeutically Targeting Glypican-2 via Single-Domain Antibody-Based Chimeric Antigen Receptors and Immunotoxins in Neuroblastoma," *Proc. Natl. Acad. Sci. USA*, vol. 114:E6623-E6631, 2017.

Orentas et al., "Identification of Cell Surface Proteins as Potential Immunotherapy Targets in 12 Pediatric Cancers," *Front. Oncol.*, vol. 2:1-16, 2012.

Rodgers et al., "Switch-mediated Activated and Retargeting of CAR-T Cells for B-Cell Malignancies," *Proc. Natl. Acad. Sci. USA*, vol. 113:E459-E468, 2016.

\* cited by examiner

*Primary Examiner* — Jessica H Roark
(74) *Attorney, Agent, or Firm* — Klarquist Sparkman, LLP

(57) ABSTRACT

A panel of human variable heavy (VH) single domain monoclonal antibodies specific for cell-surface glypican-2 (GPC2) are described. Methods for the diagnosis and treatment and GPC2-positive cancer are also described. Recombinant immunotoxins comprised of a GPC2-specific VH domain antibody and a clinically used form of *Pseudomonas* exotoxin A (PE38) were generated and shown to inhibit GPC2-positive neuroblastoma tumor cell growth and inhibit neuroblastoma xenograft growth in nude mice, without significant toxicity. Chimeric antigen receptors comprising a GPC2-specific VH single domain antibody are also described. T cells expressing the GPC2-specific CARs potently killed GPC2-positive neuroblastoma cells in a dose-dependent manner.

45 Claims, 30 Drawing Sheets
Specification includes a Sequence Listing.

FIG. 15

Clustal Omega Alignment:

```
LH1  QVQLVQSGGGLVQPGGSLRLSCAASDFDFAAYEMSWVRQAPGKGLEWIGEINHSG-STTY   59
LH2  QVQLVQSGGGLVQPGGSLRLSCAASDFYFYSYEVSWVRQAPGKALEWIGYIYYSG-STTY   59
LH6  QVQLVQSGGGLVQPGGSLRLSCAASDFYFDDYEMSWVRQAPGKGLEWVSTISGSGGTYY   60
LH7  QVQLVQSGGGLVQPGGSLRLSCAASDFYFYDYEMSWVRQAPGKGLEWIGTVSYSG-STYY   59
LH3  QVQLVQSGGGLVQPGGSLRLSCAASSFSFADYEMSWVRQAPGKALEWIGRIYTSG-STNY   59
LH4  QVQLVQSGGGLVQPGGSLRLSCAASSFYFDDYEMSWVRQAPGKALEWIGRIYTSG-STNY   59
     *:*********************..:.* * :*************.****:. ** *

LH1  NPSLKSRVTISRDNSKNTLYLQMNTLRAEDTAVYYCATAVHYDSSGYYHDAFDIWGQGT  119
LH2  NPSLKSRVTISRDNSKNTLYLQMNTLRAEDTAIYYCAVR----DNWND---VDYWGQGT  111
LH6  ADSVKGRFTISRDNSKNTLYLQMNTLRAEDTATYYCARGYS-YDDSRY----FDYWGQGT  115
LH7  NPSLKSRVTISRDNSKNTLYLQMNTLRAEDTAMYYCARGYS-YDDSRY----FDYWGQGT  114
LH3  NPSLKSRVTISRDNSKNTLYLQMNTLRAEDTATYYCARGYSGYDGSHY----FDYWGQGT  115
LH4  NPSLKSRVTISRDNSKNTLYLQMNTLRAEDTATYYCARGYCS-GGSCY----FDYWGQGT  114
     ..*:*..***************************:****.     .        ******

LH1  LVTVSS 125    SEQ ID NO: 2
LH2  LVTVSS 117    SEQ ID NO: 4
LH6  LVTVSS 121    SEQ ID NO: 10
LH7  LVTV-- 118    SEQ ID NO: 12
LH3  LVTVSS 121    SEQ ID NO: 6
LH4  LVTVSS 120    SEQ ID NO: 8
     ****
```

MONOCLONAL ANTIBODIES TARGETING GLYPICAN-2 (GPC2) AND USE THEREOF

CROSS REFERENCE TO RELATED APPLICATIONS

This application is the U.S. National Stage of International Application No. PCT/US2017/043112, filed Jul. 20, 2017, published in English under PCT Articles 21(2), which claims the benefit of U.S. Provisional Application No. 62/369,861, filed Aug. 2, 2016, which is herein incorporated by reference in its entirety.

FIELD

This disclosure concerns monoclonal antibodies that specifically bind glypican-2 and uses thereof, such as for the treatment of pediatric cancers.

BACKGROUND

Neuroblastoma is the most common extracranial solid tumors of children. Derived from neuroendocrine tissue of the sympathetic nervous system, it accounts for 8-10% of childhood cancers in the USA (Maris and Hogarty, *Lancet* 369:2106-2120, 2007). Neuroblastoma is a complex and heterogeneous disease, with nearly 50% of patients having a high-risk phenotype characterized by widespread dissemination of the cancer and poor long-term survival even if intensive multimodal treatments are used (Yu et al., *New Engl J Med* 363:1324-1334, 2010). Approximately 45% of patients receiving standard therapy have a relapse and ultimately die from metastatic disease (Matthay et al., *New Engl J Med* 341:1165-1173, 1999). As such, there is an unmet urgent need for a safe and effective treatment of neuroblastoma.

One of the most important challenges for the treatment of neuroblastoma and other deadly solid tumors (for example, lung cancer and pancreatic cancer) is the lack of tumor-specific targets. It has been shown that glypican-2 (GPC2) mRNA is highly expressed in neuroblastoma and other pediatric cancers (Orentas et al., *Front Oncol* 2:194, 2012). GPC2 belongs to the six-member human glypican family of proteins that are attached to the cell surface by a glycosylphosphatidylinositol (GPI) anchor (Filmus et al., *Genome Biol* 9:224, 2008). Unlike other known glypicans, GPC2 is uniquely expressed in the nervous system (Stipp et al., *J Cell Biol* 124:149-160, 1994), participates in cell adhesion and is thought to regulate the growth and guidance of axons. However, a possible role of GPC2 in neuroblastoma carcinogenesis has not been reported.

Antibody-based therapeutics are of growing significance for cancer therapy. Despite the success of monoclonal antibodies in the clinic, naked antibodies themselves might not always be sufficient to generate a potent antitumor response. However, they could be utilized as vehicles for the delivery of a variety of effector molecules to tumor cells. Immunotoxins are chimeric proteins composed of an antibody fragment fused to a toxin, for example the 38-kDa truncated fragment of *Pseudomonas* exotoxin (PE38). This linkage dramatically increases the activity of the monoclonal antibody and enables killing of tumor cells with relatively few target sites (Pastan et al., *Nat Rev Cancer* 6:559-565, 2006; Kreitman et al., *J Clin Oncol* 27:2983-2990, 2009; Hassan et al., *Sci Transl Med* 5, 208ra147, 2013; Hassan et al., *Clin Cancer Res* 20:5927-5936, 2014; Kreitman and Pastan, *Clin Cancer Res* 17:6398-6405, 2011). Chimeric antigen receptors (CARs) are composed of an antibody fragment (scFv) specific to a tumor antigen, fused to a transmembrane domain and a T-cell-signaling moiety. The receptors, when expressed on the surface of T cells, mediate binding of the target and activate T cells, ultimately inducing target cell lysis. CARs are emerging as one of the most promising approaches to treat leukemia (Kochenderfer et al., *Blood* 119:2709-2720, 2012; Kochenderfer and Rosenberg, *Nat Rev Clin Oncol* 10:267-276, 2013; Porter et al., *New Engl J Med* 365:725-733, 2011; Maude et al., *New Engl J Med* 371:1507-1517, 2014; Grupp et al., *New Engl J Med* 368:1509-1518, 2013). However, CARs have not been as successful in solid tumors.

Other antibody conjugates have also been utilized in the treatment of cancer. For example, antibody-drug conjugates (ADCs) are compounds that include a tumor antigen-specific antibody and a drug, typically a cytotoxic agent capable of killing tumor cells that express the tumor antigen. Since ADCs specifically target cancer cells that express the tumor antigen, the drug can be much more potent than agents used for standard chemotherapy. ADCs targeting a variety of different tumor antigens and utilizing a number of different drugs are currently being tested in clinical trials (Polakis, *Pharmacol Rev* 68(1):3-19, 2016).

Multi-specific antibodies have also been evaluated as therapeutic agents for cancer immunotherapy. Multi-specific antibodies bind at least two different antigens or epitopes to simultaneously target both tumor antigens and activating receptors, such as those expressed by T cells or natural killer cells, to enhance an anti-tumor immune response (Weidle et al., *Semin Oncol* 41(5):653-660, 2014). Bispecific antibodies targeting a variety of different tumor antigens, including HER2, CD20, EGFR, carcinoembryonic antigen (CEA) and prostate-specific membrane antigen (PSMA), are currently being evaluated in clinical trials (Fan et al., *J Hematol Oncol* 8:130, 2015).

The Wnt/β-catenin signaling pathway is a highly conserved signaling pathway during evolution. It not only plays an essential role in various processes of embryonic development (Taipale and Beachy, *Nature* 411:349-354, 2001), but also in the pathogenesis of numerous adult and pediatric tumors (Clevers and Nusse, *Cell* 149, 1192-1205, 2012). Wnt/β-catenin signaling may be of particular relevance to neuroblastoma, which arises from migratory neural crest-derived neuroblasts, as this program mediates neural crest cell fate and neural stem-cell expansion (Chenn and Walsh, *Science* 297:365-369, 2002; Lee et al., *Science* 303:1020-1023, 2004; Zechner et al., *Dev Biol* 258:406-418, 2003). In addition, glypicans play a critical role in developmental morphogenesis, and have been suggested as regulators for the Wnt signaling pathway. It has been shown that GPC3, another member of the glypican family, interacts with the Wnt ligand and may function as a co-receptor for Wnt and facilitates Wnt/Frizzled binding in liver cancer cells (Capurro et al., *Cancer Res* 65:6245-6254, 2005; Gao et al., *Hepatology* 60:576-587, 2014).

SUMMARY

Disclosed herein are six GPC2-specific human VH domain antibodies isolated by phage display. The VH single domain antibodies, referred to as LH1, LH2, LH3, LH4, LH6 or LH7, bind cell-surface human GPC2. Also disclosed herein is the finding that conjugates of the GPC2 single domain antibodies (for example, immunotoxins and chimeric antigen receptor (CAR) T cells) are capable of inhibiting GPC2-positive tumor cell growth and potently killing GPC2 positive-tumor cells.

Provided herein are VH single domain monoclonal antibodies that bind, such as specifically bind, GPC2. In some embodiments, the single domain antibodies include the complementarity determining region (CDR) sequences of LH1, LH2, LH3, LH4, LH6 or LH7. Also provided herein are conjugates that include a disclosed VH single domain monoclonal antibody. In some examples, provided are immunoconjugates, CARs, multi-specific antibodies, antibody-drug conjugates (ADCs), antibody-nanoparticles, conjugates or fusion proteins that include a monoclonal antibody or antigen-binding fragment disclosed herein. Compositions that include a GPC-specific single domain antibody and a pharmaceutically acceptable carrier are also provided by the present disclosure.

Also provided herein are nucleic acid molecules and vectors encoding the GPC2-specific single domain antibodies, immunoconjugates, CARs, multi-specific antibodies and fusion proteins disclosed herein.

Methods of treating a GPC2-positive cancer in a subject, and methods of inhibiting tumor growth or metastasis of a GPC2-positive cancer in a subject are also provided. In some embodiments, the methods include administering to the subject a VH single domain monoclonal antibody disclosed herein, or administering to the subject an immunoconjugate, CAR, ADC, multi-specific antibody, antibody-nanoparticle conjugate or fusion protein comprising a VH single domain monoclonal antibody disclosed herein.

Further provided herein are methods of detecting expression of GPC2 in a sample. In some embodiments, the method includes contacting the sample with a VH single domain monoclonal antibody disclosed herein, and detecting binding of the antibody to the sample.

The foregoing and other objects, features, and advantages of the invention will become more apparent from the following detailed description, which proceeds with reference to the accompanying figures.

BRIEF DESCRIPTION OF THE DRAWINGS

(FIG. 1A) Phage-displayed single domain antibody fragments were selected against recombinant GPC2-hFc after 4 rounds of panning A gradual increase in phage titers was observed during each round of panning (FIG. 1B) Polyclonal phage ELISA from the output phage of each round of panning BSA was used as an irrelevant antigen. (FIG. 1C) Monoclonal phage ELISA of the seven GPC2 binders. (FIG. 1D) Distribution of unique sequences of GPC2 binders in 27 selected phage clones. (FIG. 1E) Monoclonal phage ELISA analysis of cross-reactivity of GPC2 binders to human GPC1 and GPC3 and mouse GPC2. (FIG. 1F) Octet association and dissociation kinetic analysis for the interaction between various concentrations of the LH7 antibody and human GPC2. All data are represented as mean±s.e.m. of three independent experiments.

(FIG. 2A) GPC2 protein levels in human neuroblastoma cell lines including SKNSH, LAN1, IMR5, LAN5, IMR32 and NBEB as determined by western blotting. (FIG. 2B) Kaplan-Meier analysis of overall survival in neuroblastoma patients with high GPC2 mRNA expression (n=18) and low GPC2 mRNA expression (n=458) from Kocak dataset in R2 Genomics Platform. (FIG. 2C) Kaplan-Meier analysis of event-free survival in neuroblastoma patients with high GPC2 mRNA expression (n=20) and low GPC2 mRNA expression (n=456) from Kocak dataset.

(FIG. 3A) GPC2 protein expression in LAN1 and IMR5 neuroblastoma cells after siRNA-mediated knockdown of GPC2. (FIG. 3B) Inhibition of tumor cell growth by GPC2 siRNAs in both LAN1 and IMR5 cell lines. (FIG. 3C) GPC2 expression in IMR5 neuroblastoma cells after GPC2 knockout using CRISPR-Cas9 technique. GPC2 knockout decreased active β-catenin protein levels at 72 hours post transfection. (FIG. 3D) Caspase 3/7 activity in IMR5 cells after treatment with GPC2 targeted sgRNA. (FIG. 3E) Protein expression of Wnt3a and Wnt11 in neuroblastoma cell lines. (FIG. 3F) Interaction between GPC2 and Wnt3a as determined by immunoprecipitation. (FIG. 3G) Reduction of active β-catenin levels by LH7 treatment after 6 hours in HEK293 Supertopflash cells that were stimulated with Wnt3a CM. (FIG. 3H) LH7 suppressed the expression of β-catenin in HEK293 Supertopflash cells that were stimulated with LiCl and/or Wnt3a CM. Whole cell lysates were collected after 6 hours of treatment. (FIG. 3I) The anti-GPC2 antibodies decreased topflash activity in Wnt3a-activated HEK293 Supertopflash cells after 6 hours of treatment. (FIG. 3J) N-Myc protein level in neuroblastoma cell lines as determined by western blotting. (FIG. 3K) Inhibition of N-Myc expression by silencing GPC2 in neuroblastoma cells. (FIG. 3L) The proposed mechanism mediated by anti-GPC2 antibodies to inhibit neuroblastoma cell growth. Blockade of GPC2 suppresses the expression of β-catenin and its targeted genes including N-Myc. All data are represented as mean±s.e.m. of three independent experiments. *P<0.05, **P<0.01.

(FIG. 4A) Purity of LH1-PE38 (molecular weight of 53 kDa), LH4-PE38 (molecular weight of 52 kDa), and LH7-PE38 (molecular weight of 52 kDa) as determined by SDS-PAGE. (FIGS. 4B-4D) Effectiveness of anti-GPC2 immunotoxins on the growth of IMR5 (FIG. 4B), LAN1 (FIG. 4C), and SKNSH (FIG. 4D) cell lines, as measured by the WST-8 assay. An anti-mesothelin immunotoxin was used as an irrelevant control immunotoxin. (FIG. 4E) Toxicity detection of LH7-PE38 in vivo. Athymic nu/nu nude mice were treated with indicated doses of immunotoxin intravenously every other day for a total of ten injections. Each arrow indicates an individual injection (n=5 per group). (FIG. 4F) Antitumor activity of LH7-PE38. Athymic nu/nu nude mice were s.c. inoculated with $1 \times 10^7$ LAN1 cells mixed with Matrigel. When tumors reached an average volume of 150 mm$^3$, mice were treated with a 0.4 mg/kg dose of LH7-PE38 intravenously every other day for ten injections. Each arrow indicates an individual injection. n=5 per group. *P<0.05. (FIG. 4G) Body weight of the mice treated in FIG. 4F. Values represent mean±s.e.m.

(FIG. 5A) Schematic diagram of bicistronic lentiviral constructs expressing CARs targeting GPC2 along with GFP using the T2A ribosomal skipping sequence. (FIG. 5B) Timeline of CAR T cell production. (FIG. 5C) GPC2 specific CAR expression on human T cells transduced with lentiviral particles was analyzed using flow cytometry by detection of GFP fluorescence. (FIGS. 5D-5E) Cytolytic activities of GPC2 targeting CAR T cells in cell assays. The luciferase expressing IMR5 (FIG. 5D) and SKNSH (FIG. 5E) neuroblastoma cells were co-cultured with mock or GPC2 CAR-transduced T cells at the indicated Effector:Target (E:T) ratios for 20 hours, and specific lysis was measured using a luminescent-based cytolytic assay. (FIGS. 5F-5G) The above culture supernatants at an E:T ratio of 8 were harvested to measure IFN-γ (FIG. 5F) and TNF-α (FIG. 5G) secretions via ELISA. All data are represented as mean±s.e.m. of three independent experiments. *P<0.05, **P<0.01.

(FIGS. 6A-6B) Cytotoxic activity of LH7 CAR T cells derived from multiple donors. PMBCs were isolated from eight healthy donors. The luciferase expressing IMR5 cells were co-cultured with LH7 CAR-transduced T cells (FIG. 6A) or mock T cells (FIG. 6B) at the indicated E:T ratios for 20 hours, and specific lysis was measured using a luminescent-based cytolytic assay. (FIG. 6C) Quantitation of bioluminescence in mice treated in panel C. Values represent mean±s.e.m.

(FIG. 8A) Cell surface GPC2 expression in the GPC2 low expression SKNSH cell line and GPC2 overexpressing cell lines including IMR5, LAN1, IMR32 and LAN5 as determined by flow cytometry. White peaks represent the cell surface staining with isotype control, and shaded grey peaks represent the cell surface staining of GPC2. (FIG. 8B) Quantification of GPC2 sites per neuroblastoma cell using QuantiBrite PE beads. LH7 at 100 µg/ml was used for staining.

(FIG. 9A) GPC2 knockout by GPC2 sgRNAs inhibited LAN1 cell growth after 3 days of culture. (FIG. 9B) Increased expression of cleaved PARP, an apoptotic marker, in IMR5 cells after GPC2 deletion. All data are represented as mean±s.e.m. of three independent experiments. *P<0.05, **P<0.01.

(FIG. 14A) LH7 CAR T cells significantly suppressed tumor growth in a LAN1 xenograft mouse model. Nude mice were injected s.c. with 10×10$^6$ LAN1 cells. On day 13, 20 and 27 after inoculation, each mouse received 10×10$^6$ mock T cells or LH7 CAR T cells (arrows) via tail vein (n=5/group). (FIG. 14B) Body weight of mice in FIG. 14A. Arrows indicate individual injection. n=5 per group. Values represent mean±s.e.m.

FIG. 15: Clustal Omega alignment of LH1, LH2, LH3, LH4, LH6 and LH7 amino acid sequences. CDR regions according to Kabat are underlined and regions according to IMGT are shown in bold.

SEQUENCE LISTING

Figure 1A:
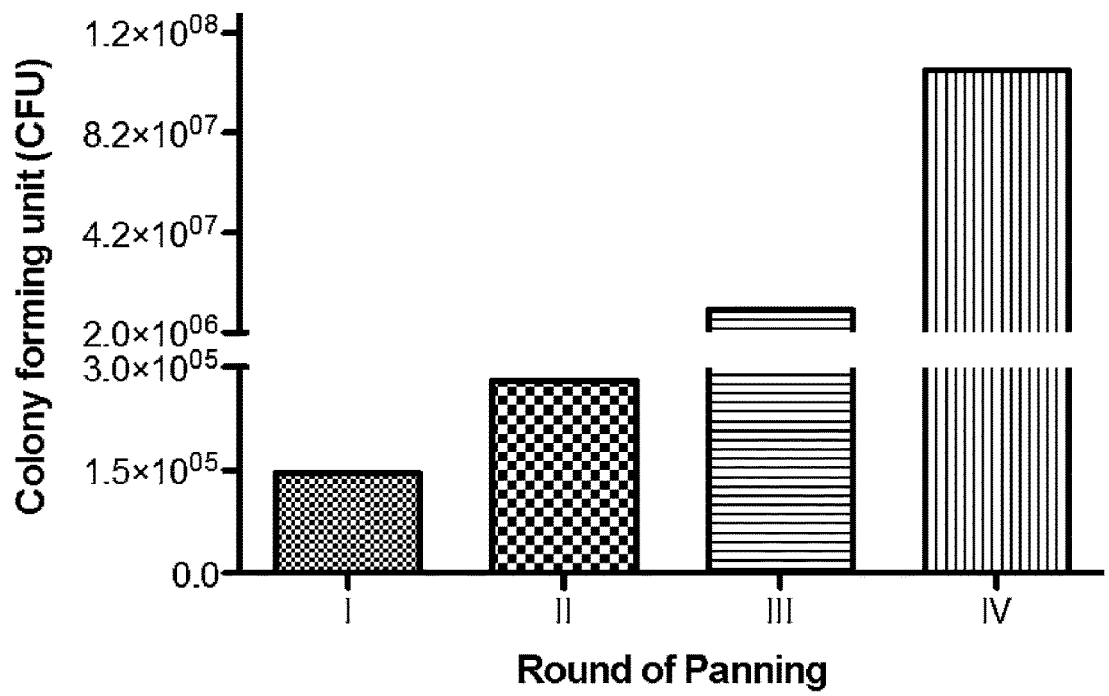
FIGS. 1A-1F: Isolation of GPC2 specific human single domain antibodies by phage display.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 28, 2019, 16.2 KB, which is incorporated by reference herein. In the accompanying sequence listing:

SEQ ID NO: 1 is the nucleotide sequence of $V_H$ single domain antibody LH1.

SEQ ID NO: 2 is the amino acid sequence of $V_H$ single domain antibody LH1.

SEQ ID NO: 3 is the nucleotide sequence of $V_H$ single domain antibody LH2.

SEQ ID NO: 4 is the amino acid sequence of $V_H$ single domain antibody LH2.

SEQ ID NO: 5 is the nucleotide sequence of $V_H$ single domain antibody LH3.

SEQ ID NO: 6 is the amino acid sequence of $V_H$ single domain antibody LH3.

SEQ ID NO: 7 is the nucleotide sequence of $V_H$ single domain antibody LH4.

SEQ ID NO: 8 is the amino acid sequence of $V_H$ single domain antibody LH4.

SEQ ID NO: 9 is the nucleotide sequence of $V_H$ single domain antibody LH6.

SEQ ID NO: 10 is the amino acid sequence of $V_H$ single domain antibody LH6.

SEQ ID NO: 11 is the nucleotide sequence of $V_H$ single domain antibody LH7.

SEQ ID NO: 12 is the amino acid sequence of $V_H$ single domain antibody LH7.

SEQ ID NO: 13 is a CDR1 consensus amino acid sequence (IMGT).

SEQ ID NO: 14 is a CDR1 consensus amino acid sequence (Kabat).

SEQ ID NO: 15 is a CDR2 consensus amino acid sequence (IMGT).

SEQ ID NO: 16 is a CDR2 consensus amino acid sequence (IMGT).

SEQ ID NO: 17 is a CDR2 consensus amino acid sequence (Kabat).

SEQ ID NO: 18 is a CDR2 consensus amino acid sequence (Kabat).

SEQ ID NO: 19 is a CDR3 consensus amino acid sequence (IMGT/Kabat).

SEQ ID NOs: 20-22 are sgRNA sequences.

SEQ ID NOs: 23-25 are GPC2-specific siRNA sequences.

SEQ ID NO: 26 is the amino acid sequence of a peptide neo-epitope.

DETAILED DESCRIPTION

I. Abbreviations

ADC antibody-drug conjugate
BSA bovine serum albumin
CAR chimeric antigen receptor
CTL cytotoxic T lymphocyte
CM condition media
E:T effector to target
ELISA enzyme linked immunosorbent assay
FACS fluorescent activated cell sorting GFP green fluorescent protein
GPC2 glypican-2
GPI glycosylphosphatidylinositol
hFc human Fc
HRP horseradish peroxidase
IFN interferon
IL interleukin
i.p. intraperitoneal
i.v. intravenous
mFc murine Fc
MOI multiplicity of infection
PARP poly-ADP ribose polymerase
PBMC peripheral blood mononuclear cells
PE *Pseudomonas* exotoxin
PE phycoerythrin
PEI polyethylenimine
PFU plaque forming units
RLU relative light units
s.c. subcutaneous
scFv single chain variable fragment
SEM standard error of the mean
sgRNA single guide RNA
siRNA small interfering RNA
TCF T cell factor

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

4-1BB: A co-stimulatory molecule expressed by T cell receptor (TCR)-activated lymphocytes, and by other cells including natural killer cells. Ligation of 4-1BB induces a signaling cascade that results in cytokine production, expression of anti-apoptotic molecules and an enhanced immune response.

Acute lymphoblastic leukemia (ALL): An acute form of leukemia characterized by the overproduction of lymphoblasts. ALL is most common in childhood, peaking at ages 2-5.

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_HH$ antibodies, and $V_L$ domain antibodies. $V_{NAR}$ antibodies are produced by cartilaginous fish, such as nurse sharks, wobbegong sharks, spiny dogfish and bamboo sharks. Camelid $V_HH$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Antibody-drug conjugate (ADC): A molecule that includes an antibody (or antigen-binding fragment of an antibody) conjugated to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand cross-linking agents (e.g., pyrrolobenzodiazepines; PDBs).

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as GPC2) is an antibody that binds the antigen with high affinity and does not significantly bind other unrelated antigens.

Bispecific antibody: A recombinant protein that includes antigen-binding fragments of two different monoclonal antibodies, and is thereby capable of binding two different antigens. In some embodiments, bispecific antibodies are used for cancer immunotherapy by simultaneously targeting, for example, both CTLs (such as a CTL receptor component such as CD3) or effector natural killer (NK) cells, and a tumor antigen. Similarly, a multi-specific antibody is a recombinant protein that includes antigen-binding fragments of at least two different monoclonal antibodies, such as two, three or four different monoclonal antibodies.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neuroblastoma. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds GPC2 used in combination with a radioactive or chemical compound.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs are comprised of an antigen-binding moiety, a transmembrane domain and an endodomain. The endodomain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28, 4-1BB (CD137), ICOS, OX40 (CD134), CD27 and/or DAP10.

Complementarity determining region (CDR): A region of hypervariable amino acid sequence that defines the binding affinity and specificity of an antibody.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, carbohydrate or recombinant virus. An antibody conjugate is often referred to as an "immunoconjugate." When the conjugate comprises an antibody linked to a drug (e.g., a cytotoxic agent), the conjugate is often referred to as an "antibody-drug conjugate" or "ADC." Other antibody conjugates include, for example, multi-specific (such as bispecific or trispecific) antibodies and chimeric antigen receptors (CARs).

Conservative variant: "Conservative" amino acid substitutions are those substitutions that do not substantially affect or decrease the affinity of a protein, such as an antibody to GPC2. For example, a monoclonal antibody that specifically binds GPC2 can include at most about 1, at most about 2, at most about 5, and most about 10, or at most about 15 conservative substitutions and specifically bind the GPC2 polypeptide. The term "conservative variant" also includes the use of a substituted amino acid in place of an unsubstituted parent amino acid, provided that antibody specifically binds GPC2. Non-conservative substitutions are those that reduce an activity or binding to GPC2.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxic agent: Any drug or compound that kills cells.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a GPC2 polypeptide or an antibody that binds GPC2 that includes a sequence that is degenerate as a result of the genetic code. There are 20 natural amino acids, most of which are specified by more than one codon. Therefore, all degenerate nucleotide sequences are included as long as the amino acid sequence of the GPC2 polypeptide or antibody that binds GPC2 encoded by the nucleotide sequence is unchanged.

Desmoplastic small round cell tumor (DRCT): A soft tissue sarcoma that predominantly occurs in childhood, particularly in boys. DRCT is an aggressive and rare type of cancer that primarily occurs as a masses in the abdomen, but can also be found in the lymph nodes, the lining of the abdomen, diaphragm, spleen, liver, chest wall, skull, spinal cord, intestine, bladder, brain, lungs, testicles, ovaries and the pelvis.

Diagnostic: Identifying the presence or nature of a pathologic condition, such as neuroblastoma. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as neuroblastoma.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms. Therapeutic agents (or drugs) include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-GPC2 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels. Detectable labels useful for such purposes are also well known in the art, and include radioactive isotopes such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as GPC2.

Ewing's sarcoma: A rare type of malignant tumor found in bone or soft tissue. Ewing's sarcoma is a small, blue, round cell tumor.

Framework region: Amino acid sequences interposed between CDRs. Framework regions include variable light and variable heavy framework regions. The framework regions serve to hold the CDRs in an appropriate orientation for antigen binding.

Fusion protein: A protein comprising at least a portion of two different (heterologous) proteins.

Glypican-2 (GPC2): A member of the six-member glypican family of heparan sulfate (HS) proteoglycans that are attached to the cell surface by a GPI anchor (Filmus et al., *Genome Biol* 9:224, 2008). GPC2 is uniquely expressed in the nervous system (Stipp et al., *J Cell Biol* 124:149-160, 1994), participates in cell adhesion and is thought to regulate the growth and guidance of axons. In addition, GPC2 mRNA is highly expressed in neuroblastoma and other pediatric cancers (Orentas et al., *Front Oncol* 2:194, 2012). GPC2 is also known as cerebroglycan proteoglycan and glypican proteoglycan 2. GPC2 genomic, mRNA and protein sequences are publically available (see, for example, NCBI Gene ID 221914).

GPC2-positive cancer: A cancer that overexpresses GPC2. Examples of GPC2-positive cancers include, but are not limited to, neuroblastoma, acute lymphoblastic leukemia, embryonal rhabdomyosarcoma, alveolar rhabdomyosarcoma, Ewing's sarcoma, desmoplastic small round cell tumor or osteosarcoma.

Heterologous: Originating from a separate genetic source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4$^+$ response or a CD8$^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunoliposome: A liposome with antibodies or antibody fragments conjugated to its surface Immunoliposomes can carry cytotoxic agents or other drugs to antibody-targeted cells, such as tumor cells.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Neuroblastoma: A solid tumor arising from embryonic neural crest cells. Neuroblastoma commonly arises in and around the adrenal glands, but can occur anywhere that sympathetic neural tissue is found, such as in the abdomen, chest, neck or nerve tissue near the spine. Neuroblastoma typically occurs in children younger than 5 years of age.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Osteosarcoma: A type of cancerous tumor found in the bone. Osteosarcoma is an aggressive cancer arising from primitive transformed cells of mesenchymal origin. This type of cancer is most prevalent in children and young adults.

Pediatric cancer: A cancer that develops in children ages 0 to 14. The major types of pediatric cancers include, for example, neuroblastoma, acute lymphoblastic leukemia (ALL), embryonal rhabdomyosarcoma (ERMS), alveolar rhabdomyosarcoma (ARMS), Ewing's sarcoma, desmoplastic small round cell tumor (DRCT), osteosarcoma, brain and other CNS tumors, Wilm's tumor, non-Hodgkin lymphoma, and retinoblastoma.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Pyrrolobenzodiazepine (PBD): A class of sequence-selective DNA minor-groove binding crosslinking agents originally discovered in *Streptomyces* species. PDBs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2):254-293, 2012).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Rhabdomyosarcoma (RMS): A soft tissue malignant tumor of skeletal muscle origin. The most common primary sites for rhabdomyosarcoma are the head and neck (e.g., parameningeal, orbit, pharyngeal, etc.), the genitourinary tract, and the extremities. Other less common primary sites include the trunk, chest wall, the abdomen (including the retroperitoneum and biliary tract), and the perineal/anal region. There are at least two types of RMS; the most common forms are alveolar RMS (ARMS) and embryonal histological RMS (ERMS). Approximately 20% of children with rhabdomyosarcoma have the ARMS subtype. An increased frequency of this subtype is noted in adolescents and in patients with primary sites involving the extremities, trunk, and perineum/perianal region. ARMS is associated with chromosomal translocations encoding a fusion gene involving FKHR on chromosome 13 and members of the PAX family. The embryonal subtype is the most frequently observed subtype in children, accounting for approximately 60-70% of rhabdomyosarcomas of childhood. Tumors with embryonal histology typically arise in the head and neck region or in the genitourinary tract, although they may occur at any primary site. ERMS is characterized by a younger age at diagnosis, loss of heterozygosity, and altered genomic imprinting.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_H$ of an antibody that specifically binds a GPC2 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

The glypican-2 (GPC2) protein is required for neuronal cell adhesion and neurite outgrowth. However, prior to the present disclosure, its role in neuroblastoma carcinogenesis remained unclear. The data disclosed herein demonstrated that GPC2 protein expression was elevated in neuroblastomas as compared with human normal tissues. Seven human single domain antibodies (LH1-LH7) specific for cell surface GPC2 were isolated. Recombinant immunotoxins were produced by fusing the LH1, LH4 and LH7 antibody fragments to a clinically used form of *Pseudomonas* exotoxin A (PE38). All three immunotoxins inhibited GPC2-positive neuroblastoma tumor cell growth with $EC_{50}$ values of 4.6 nM to 43.9 nM and had no effect on GPC2-negative cells. One of the immunotoxins (LH7-PE38) was tested in vivo and was shown to significantly inhibit neuroblastoma xenograft growth in nude mice without significant toxicity or any other side effects. Chimeric antigen receptors (CARs) were also generated using antibodies LH1, LH2, LH3, LH4, LH6 and LH7. All GPC2-targeted CAR-T cells potently killed GPC2 positive-neuroblastoma cells in a dose-dependent manner, but not GPC2-negative cells, and induced production of both IFN-γ and TNF-α. LH7 CAR T cells were tested in two animal models of neuroblastoma. The results demonstrated that LH7 CAR T cells were able to effectively suppress metastatic tumors and reduce tumor volume. In addition, silencing GPC2 via CRISPR-Cas9 and siRNA techniques significantly inhibited neuroblastoma tumor cell growth and induced apoptosis. Moreover, the LH7 antibody blocked the interaction between GPC2 and Wnt3a and thereby suppressed active β-catenin level and T-cell factor (TCF) transcriptional activity in GPC2-expressing cells. The present disclosure establishes GPC2 as a therapeutic target for neuroblastoma and provides antibody drug candidates for the treatment of neuroblastoma.

IV. Single Domain Antibodies Specific for Glypican-2 (GPC2)

Disclosed herein are six GPC2-specific human VH domain antibodies isolated by phage display with selection against GPC2-hFc. The VH domain antibodies, referred to herein as LH1, LH2, LH3, LH4, LH6 and LH7, bind cell-surface human GPC2. VH domain antibodies LH3, LH4 and LH6 also bind mouse GPC2, and LH3 is cross-reactive with other glypican proteins (see FIG. 1E).

The nucleotide and amino acid sequences of the VH single domain antibodies LH1, LH2, LH3, LH4, LH6 and LH7 are provided below. The locations of the CDRs, using both the Kabat and IMGT numbering schemes, are listed in Tables 1 and 2. However, one of skill in the art could readily determine the CDR boundaries using alternative numbering schemes, such as the Chothia numbering scheme. In the amino acids sequences below, the CDR regions according to Kabat are underlined and the CDR regions according to IMGT are shown in bold.

```
LH1 DNA
                                        (SEQ ID NO: 1)
CAGGTGCAGCTGGTGCAGTCTGGGGGAGGCTTGGTACAGCCTGGAGGGT

CCCTGAGACTCTCCTGTGCAGCCTCTGATTTCGATTTCGCTGCTTATGA

AATGAGCTGGGTCCGCCAGGCTCCAGGGAAGGGTCTAGAGTGGATTGGG

GAAATCAATCATAGTGGAAGCACCACCTACAACCCGTCCCTCAAGAGTC

GAGTCACCATCTCCAGAGACAATTCCAAGAACACGCTGTATCTGCAAAT

GAACACCCTGAGAGCCGAGGACACAGCCGTGTATTACTGTGCGACCGCC

GTGCATTACTATGATAGTAGTGGTTATTACCATGATGCTTTTGATATCT

GGGGCCAAGGCACCCTGGTCACCGTCTCCTCA

LH1 protein
                                        (SEQ ID NO: 2)
QVQLVQSGGGLVQPGGSLRLSCAASDFDFAAYEMSWVRQAPGKGLEWIG

EINHSGSTTYNPSLKSRVTISRDNSKNTLYLQMNTLRAEDTAVYYCATA

VHYYDSSGYYHDAFDIWGQGTLVTVSS

LH2 DNA
                                        (SEQ ID NO: 3)
CAGGTGCAGCTGGTGCAGTCTGGGGGAGGCTTGGTACAGCCTGGAGGGT

CCCTGAGACTCTCCTGTGCAGCCTCTGATTTCTATTTCTATTCTTATGA
```

AGTGAGCTGGGTCCGCCAGGCTCCAGGGAAGGCCCTGGAGTGGATTGGG

TATATCTATTACAGTGGGAGCACCACCTACAACCCGTCCCTCAAGAGTC

GAGTCACCATCTCCAGAGACAATTCCAAGAACACGCTGTATCTGCAAAT

GAACACCCTGAGAGCCGAGGACACAGCCATATATTACTGTGCGGTCCGG

GACAACTGGAACGACGTTGACTACTGGGGCCAGGGAACCCTGGTCACCG

TCTCCTCA

LH2 protein
(SEQ ID NO: 4)
QVQLVQSGGGLVQPGGSLRLSCAASDFYFYSYEVSWVRQAPGKALEWIG

YIYYSGSTTYNPSLKSRVTISRDNSKNTLYLQMNTLRAEDTAIYYCAVR

DNWNDVDYWGQGTLVTVSS

LH3 DNA
(SEQ ID NO: 5)
CAGGTGCAGCTGGTGCAGTCTGGGGGAGGCTTGGTACAGCCTGGAGGGT

CCCTGAGACTCTCCTGTGCAGCCTCTTCTTTCTCTTTCGCTGATTATGA

AATGAGCTGGGTCCGCCAGGCTCCAGGGAAGGCCCTGGAGTGGATTGGG

CGTATCTATACCAGTGGGAGCACCAACTACAACCCCTCCCTCAAGAGTC

GAGTCACCATCTCCAGAGACAATTCCAAGAACACGCTGTATCTGCAAAT

GAACACCCTGAGAGCCGAGGACACAGCCACATATTACTGTGCGAGAGGA

TATAGTGGCTACGATGGATCGCACTACTTTGACTACTGGGGCCAGGGAA

CCCTGGTCACCGTCTCCTCA

LH3 protein
(SEQ ID NO: 6)
QVQLVQSGGGLVQPGGSLRLSCAASSFSFADYEMSWVRQAPGKALEWIG

RIYTSGSTNYNPSLKSRVTISRDNSKNTLYLQMNTLRAEDTATYYCARG

YSGYDGSHYFDYWGQGTLVTVSS

LH4 DNA
(SEQ ID NO: 7)
CAGGTGCAGCTGGTGCAGTCTGGGGGAGGCTTGGTACAGCCTGGAGGGT

CCCTGAGACTCTCCTGTGCAGCCTCTTCTTTCTATTTCGATGATTATGA

AATGAGCTGGGTCCGCCAGGCTCCAGGGAAGGCCCTGGAGTGGATTGGG

CGTATCTATACCAGTGGGAGCACCAACTACAACCCCTCCCTCAAGAGTC

GAGTCACCATCTCCAGAGACAATTCCAAGAACACGCTGTATCTGCAAAT

GAACACCCTGAGAGCCGAGGACACAGCCACGTATTACTGTGCGAGGGGA

TATTGTAGTGGTGGTAGCTGCTACTTTGACTACTGGGGCCAGGGAACCC

TGGTCACCGTCTCCTCA

LH4 protein
(SEQ ID NO: 8)
QVQLVQSGGGLVQPGGSLRLSCAASSFYFDDYEMSWVRQAPGKALEWIG

RIYTSGSTNYNPSLKSRVTISRDNSKNTLYLQMNTLRAEDTATYYCARG

YCSGGSCYFDYWGQGTLVTVSS

LH6 DNA
(SEQ ID NO: 9)
CAGGTGCAGCTGGTGCAGTCTGGGGGAGGCTTGGTACAGCCTGGAGGGT

CCCTGAGACTCTCCTGTGCAGCCTCTGATTTCTATTTCGATGATTATGA

AATGAGCTGGGTCCGCCAGGCTCCAGGGAAGGGGCTGGAGTGGGTCTCA

ACTATTAGTGGTAGTGGTGGTGGCACATACTACGCAGACTCAGTGAAGG

GCCGATTCACCATCTCCAGAGACAATTCCAAGAACACGCTGTATCTGCA

AATGAACACCCTGAGAGCCGAGGACACAGCCACATATTACTGTGCGAGA

GGTTACAGTTATGACGACTCCCGATATTTTGACTACTGGGGCCAGGGAA

CCCTGGTCACCGTCTCCTCA

LH6 protein
(SEQ ID NO: 10)
QVQLVQSGGGLVQPGGSLRLSCAASDFYFDDYEMSWVRQAPGKGLEWVS

TISGSGGGTYYADSVKGRFTISRDNSKNTLYLQMNTLRAEDTATYYCAR

GYSYDDSRYFDYWGQGTLVTVSS

LH7 DNA
(SEQ ID NO: 11)
CAGGTGCAGCTGGTGCAGTCTGGGGGAGGCTTGGTACAGCCTGGAGGGT

CCCTGAGACTCTCCTGTGCAGCCTCTGATTTCTATTTCTATGATTATGA

AATGAGCTGGGTCCGCCAGGCTCCAGGGAAGGGTCTGGAGTGGATTGGG

ACTGTCTCCTATAGTGGGAGCACCTACTACAACCCGTCCCTCAAGAGTC

GAGTCACCATCTCCAGAGACAATTCCAAGAACACGCTGTATCTGCAAAT

GAACACCCTAAGAGCCGAGGACACAGCCATGTATTACTGTGCGAGAGGT

TACAGCTATGATGACTCCCGATATTTTGACTACTGGGGCCAGGGAACCC

TGGTCACCGTCTCCTCA

LH7 protein
(SEQ ID NO: 12)
QVQLVQSGGGLVQPGGSLRLSCAASDFYFYDYEMSWVRQAPGKGLEWIG

TVSYSGSTYYNPSLKSRVTISRDNSKNTLYLQMNTLRAEDTAMYYCARG

YSDDSRYFDYWGQGTLVTVSS

TABLE 1

CDR Residues According to IMGT

| Antibody | CDR1 | CDR2 | CDR3 | SEQ ID NO: |
|---|---|---|---|---|
| LH1 | 26-33 | 51-57 | 96-114 | 2 |
| LH2 | 26-33 | 51-57 | 96-106 | 4 |
| LH3 | 26-33 | 51-57 | 96-110 | 6 |
| LH4 | 26-33 | 51-57 | 96-109 | 8 |
| LH6 | 26-33 | 51-58 | 97-110 | 10 |
| LH7 | 26-33 | 51-57 | 96-109 | 12 |

TABLE 2

CDR Residues According to Kabat

| Antibody | CDR1 | CDR2 | CDR3 | SEQ ID NO: |
|---|---|---|---|---|
| LH1 | 31-35 | 50-65 | 96-114 | 2 |
| LH2 | 31-35 | 50-65 | 96-106 | 4 |
| LH3 | 31-35 | 50-65 | 96-110 | 6 |
| LH4 | 31-35 | 50-65 | 96-109 | 8 |
| LH6 | 31-35 | 50-66 | 97-110 | 10 |
| LH7 | 31-35 | 50-65 | 96-109 | 12 |

As shown in FIG. 15, the CDR sequences of each antibody share at least some degree of similarity. Therefore, consensus CDR sequences (both IMGT and Kabat) were determined for each single domain antibody.

CDR Consensus Sequences of LH1, LH2, LH3, LH4, LH6 and LH7

CDR1 consensus (IMGT; All):

$X_1FX_2FX_3X_4YE$ (SEQ ID NO: 13), where $X_1$=D or S; $X_2$=D, Y or S; $X_3$=A, Y or D; and $X_4$=A, S or D CDR1 Consensus (Kabat; All):

$X_1YEX_2S$ (SEQ ID NO: 14), where $X_1$=A, S or D; and $X_2$=M or V

CDR2 Consensus (IMGT; All):

$X_1X_2X_3SGX_4X_5T$ (SEQ ID NO: 15), where $X_1$=I or V; $X_2$=N, Y or S; $X_3$=H, Y, G or T; $X_4$=G or no amino acid; and $X_5$=S or G CDR2 Consensus (IMGT; Excluding LH6):

$X_1X_2X_3SGST$ (SEQ ID NO: 16), where $X_1$=I or V; $X_2$=N, Y or S; and $X_3$=H, Y, G or T CDR2 Consensus (Kabat; all):

$X_1X_2X_3X_4SGX_5X_6TX_7YX_8X_9SX_{10}KX_{11}$ (SEQ ID NO: 17), where $X_1$=E, Y, T or R; $X_2$=I or V; $X_3$=N, Y S; $X_4$=H, Y, G or T; $X_5$=G or no amino acid; $X_6$=S or G; $X_7$=T, Y or N; $X_8$=N or A; $X_9$=P or D; $X_{10}$=L or V; and $X_{11}$=S or G CDR2 Consensus (Kabat; Excluding LH6):

$X_1X_2X_3X_4SGSTX_5YNPSLKS$ (SEQ ID NO: 18), where $X_1$=E, Y, T or R; $X_2$=I or V; $X_3$=N, Y or S; $X_4$=H, Y or T; and $X_5$=T, Y or N CDR3 Consensus (IMGT/Kabat; LH3, LH4, LH6 and LH7 Only):

$ARGYX_1X_2X_3X_4X_5SX_6YFDY$ (SEQ ID NO: 19), where $X_1$=S or C; $X_2$=G, S or no amino acid; $X_3$=Y or no amino acid; $X_4$=D or G; $X_5$=D or G; and $X_6$=R, H or C Provided herein are VH single domain monoclonal antibodies that bind (for example, specifically bind) GPC2, such as cell-surface or soluble GPC2. In some embodiments, the VH domain comprises at least a portion of the amino acid sequence set forth herein as SEQ ID NO: 2 (LH1), SEQ ID NO: 4 (LH2), SEQ ID NO: 6 LH3), SEQ ID NO: 8 (LH4), SEQ ID NO: 10 (LH6), or SEQ ID NO: 12 (LH7), such as one or more (such as all three) CDR sequences.

In some embodiments, the VH single domain antibody that binds GPC2 includes a CDR1 sequence set forth as SEQ ID NO: 13 or SEQ ID NO: 14; a CDR2 sequence set forth as SEQ ID NO: 15, SEQ ID NO: 16, SEQ ID NO: 17 or SEQ ID NO: 18; and/or a CDR3 sequence set forth as SEQ ID NO: 19, residues 96-114 of SEQ ID NO: 2 or residues 96-106 of SEQ ID NO: 4.

In particular embodiments, the VH single domain monoclonal antibody includes the CDR1, CDR2 and/or CDR3 sequences of SEQ ID NO: 2, SEQ ID NO: 4, SEQ ID NO: 6, SEQ ID NO: 8, SEQ ID NO: 10 or SEQ ID NO: 12.

In some embodiments, the CDR sequences are determined using the IMGT, Kabat or Chothia numbering scheme.

In some examples, the CDR1, CDR2 and CDR3 sequences of the GPC2-specific VH domain antibody are determined using IMGT and are respectively set forth as residues 26-33, 51-57 and 96-114 of SEQ ID NO: 2; residues 26-33, 51-57 and 96-106 of SEQ ID NO: 4; residues 26-33, 51-57 and 96-110 of SEQ ID NO: 6; residues 26-33, 51-57 and 96-109 of SEQ ID NO: 8; residues 26-33, 51-58 and 97-110 of SEQ ID NO: 10; or residues 26-33, 51-57 and 96-109 of SEQ ID NO: 12.

In other examples, the CDR1, CDR2 and CDR3 sequences of the GPC2-specific VH domain antibody are determined using Kabat and are respectively set forth as residues 31-35, 50-65 and 96-114 of SEQ ID NO: 2; residues 31-35, 50-65 and 96-106 of SEQ ID NO: 4; residues 31-35, 50-65 and 96-110 of SEQ ID NO: 6; residues 31-35, 50-65 and 96-109 of SEQ ID NO: 8; residues 31-35, 50-66 and 97-110 of SEQ ID NO: 10; or residues 31-35, 50-65 and 96-109 of SEQ ID NO: 12.

In particular examples, the amino acid sequence of the VH single domain monoclonal antibody is at least 80%, at least 85%, at least 90%, at least 95%, at least 96%, at least 97%, at least 98% or at least 99% identical to SEQ ID NO: 2, SEQ ID NO: 4, SEQ ID NO: 6, SEQ ID NO: 8, SEQ ID NO: 10 or SEQ ID NO: 12.

In specific, non-limiting examples, the amino acid sequence of the VH single domain monoclonal antibody comprises or consists of SEQ ID NO: 2, SEQ ID NO: 4, SEQ ID NO: 6, SEQ ID NO: 8, SEQ ID NO: 10 or SEQ ID NO: 12.

In some embodiments, the VH single domain monoclonal antibody is a chimeric, synthetic, humanized or human antibody.

Also provided herein are immunoconjugates that include a VH single domain monoclonal antibody disclosed herein and an effector molecule. In some embodiments, the effector molecule is a toxin, such as *Pseudomonas* exotoxin or a variant thereof. In some examples, the *Pseudomonas* toxin is PE38. In other embodiments, the effector molecule is a detectable label, such as a fluorophore, an enzyme or a radioisotope. Immunoconjugates are further described in section V.

Further provided herein are chimeric antigen receptors (CARs) that include a VH single domain monoclonal antibody disclosed herein. In some embodiments, the CAR further includes one or more of a hinge region, a transmembrane domain, a costimulatory signaling moiety, and a signaling domain. In some examples, the hinge region includes a CD8a hinge region. In some examples, the transmembrane domain includes a CD8α or a CD28 transmembrane domain. In some examples, the costimulatory signaling moiety comprises a 4-1BB and/or a CD28 signaling moiety. In some examples, the signaling domain comprises a CD3ζ signaling domain. Isolated cells, such as CTLs, expressing a GPC2-targeting CAR are also provided. CARs are further described in section VI.

Also provided herein are antibody-drug conjugates (ADCs) that include a drug conjugated to a VH single domain monoclonal antibody disclosed herein. In some embodiments, the drug is a small molecule. In some embodiments, the drug is an anti-microtubule agent, an anti-mitotic agent and/or a cytotoxic agent. ADCs are further described in section VII.

Further disclosed herein are multi-specific antibodies that include a VH single-domain monoclonal antibody described herein and at least one additional monoclonal antibody or antigen-binding fragment thereof. In some embodiments, the multi-specific antibody is a bispecific antibody. In other embodiments, the multi-specific antibody is a trispecific antibody. In some examples, the at least one additional monoclonal antibody or antigen binding fragment thereof specifically binds a component of the T cell receptor or a natural killer (NK) cell activating receptor. Multi-specific antibodies are further described in section VIII.

Also provided are antibody-nanoparticle conjugates that include a nanoparticle conjugated to a VH single-domain monoclonal antibody disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent. Antibody-nanoparticle conjugates are further described in section IX.

Further provided herein are fusion proteins that include a VH single domain monoclonal antibody disclosed herein and a heterologous protein or peptide. In some embodiments, the heterologous protein is an Fc protein. In some examples, the Fc protein is a mouse Fc or a human Fc protein. In some embodiments, the heterologous peptide is not endogenous to humans (for example, the heterologous peptide is a peptide neo-epitope). In some embodiments, the heterologous peptide is about 8 to about 20 amino acids in length. In particular examples, the heterologous peptide is about 14 amino acids in length. In one specific, non-limiting example, the heterologous peptide comprises of consists of NYHLENEVARLKKL (SEQ ID NO: 26).

Compositions that include a pharmaceutically acceptable carrier and a VH single domain monoclonal antibody, an immunoconjugate, a CAR, an isolated cell (expressing a CAR), an ADC, a multi-specific antibody, an antibody-nanoparticle conjugate, or a fusion protein disclosed herein are further provided by the present disclosure.

Also provided are nucleic acid molecules encoding a VH single domain monoclonal antibody disclosed herein. In some embodiments, the nucleic acid molecule is at least 80%, at least 85%, at least 90%, at least 95%, at least 96%, at least 97%, at least 98% or at least 99% identical to SEQ ID NO: 1, SEQ ID NO: 3, SEQ ID NO: 5, SEQ ID NO: 7, SEQ ID NO: 9 or SEQ ID NO: 11. In some examples, the nucleic acid molecule comprises of consists of SEQ ID NO: 1, SEQ ID NO: 3, SEQ ID NO: 5, SEQ ID NO: 7, SEQ ID NO: 9 or SEQ ID NO: 11. Further provided are nucleic acid molecules encoding an immunoconjugate, CAR, multi-specific antibody, or fusion protein disclosed herein. In some embodiments, the nucleic acid molecule is operably linked to a promoter. Vectors that include the nucleic acid molecules are further provided herein.

Methods of treating a GPC2-positive cancer in a subject are provided herein. Also provided are methods of inhibiting tumor growth or metastasis of a GPC2-positive cancer in a subject. In some embodiments, the methods include administering to the subject a VH single domain monoclonal antibody disclosed herein, or administering to the subject an immunoconjugate, CAR, ADC, multi-specific antibody, antibody-nanoparticle conjugate or fusion protein comprising a VH single domain monoclonal antibody disclosed herein. In some embodiments, the GPC2-positive cancer is a pediatric cancer. In some examples, the GPC2-positive cancer is a neuroblastoma, acute lymphoblastic leukemia, embryonal rhabdomyosarcoma, alveolar rhabdomyosarcoma, Ewing's sarcoma, desmoplastic small round cell tumor or osteosarcoma.

Further provided herein are methods of detecting expression of GPC2 in a sample. In some embodiments, the method includes contacting the sample with a VH single domain monoclonal antibody disclosed herein; and detecting binding of the antibody to the sample, thereby detecting expression of GPC2 in the sample. In some embodiments, the VH single domain monoclonal antibody is directly labeled. In other embodiments, the method further includes contacting the VH single domain monoclonal antibody with a second antibody, and detecting the binding of the second antibody to the VH single domain monoclonal antibody. In some examples, the sample is obtained from a subject suspected of having a GPC2-positive cancer. In some examples, the sample is a tumor biopsy.

V. Immunoconjugates

The disclosed monoclonal antibodies can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; U.S. Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/031741, WO 2009/32954, WO 2011/32022, WO 2012/154530, and WO 2012/170617.

The antibodies described herein can also be used to target any number of different diagnostic or therapeutic compounds to cells expressing the tumor or viral antigen on their surface. Thus, an antibody of the present disclosure can be attached directly or via a linker to a drug that is to be delivered directly to cells expressing cell-surface antigen. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Chimeric Antigen Receptors (CARs)

The disclosed monoclonal antibodies can also be used to produce CARs (also known as chimeric T cell receptors, artificial T cell receptors or chimeric immunoreceptors) and/or cytotoxic T lymphocytes (CTLs) engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010; Dai et al., *J Natl Cancer Inst* 108(7):djv439, 2016). In many instances, the binding moiety is an antigen binding fragment of a monoclonal antibody, such as a scFv or single-domain antibody. The spacer/hinge region typically includes sequences from IgG subclasses, such as IgG1, IgG4, IgD and CD8 domains. The transmembrane domain can be can derived from a variety of different T cell proteins, such as CD3ζ, CD4, CD8 or CD28. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28, 4-1BB (CD137, TNFRSF9), OX-40 (CD134), ICOS, CD27 and/or DAP10.

CTLs expressing CARs can be used to target a specific cell type, such as a GPC2-positive tumor cell. Thus, the monoclonal antibodies disclosed herein can be used to engineer CTLs that express a CAR containing the GPC2-specific single domain antibody, thereby targeting the engineered CTLs to GPC2-expressing tumor cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Accordingly, provided herein are CARs that include a GPC2-specific antibody. Also provided are isolated nucleic acid molecules and vectors encoding the CARs, and host cells, such as CTLs, expressing the CARs. CTLs expressing CARs comprised of a GPC2-specific monoclonal antibody can be used for the treatment of cancers that express GPC2. In some embodiments herein, the CAR is a bispecific CAR.

In some instances, it is desirable to regulate the activation and expansion of CAR-expressing T cells after they have been infused into a patient. Several strategies have been developed to module CAR-expressing T cells in vivo, including the use of antibody-based switches that mediate interactions between CAR-expressing T cells and targeted tumors cells, as described by Rodgers et al. (*Proc Natl Acad Sci USA* 113(4):E459-E468, 2016, which is incorporated herein by reference). The antibody-based switches are comprised of a tumor antigen-specific antibody that has been grafted with a peptide neo-epitope (PNE). Switchable CAR T (sCAR-T) cells are designed to specifically bind the PNE. Since the sCAR-T cells do not bind endogenous antigens, the presence of the switch is required for its activation.

Thus, provided herein are antibody-based switches that include a GPC2-specific VH single domain antibody disclosed herein fused to a heterologous peptide, such as a PNE. In some embodiments, the heterologous peptide is not endogenous to humans (for example, it is a peptide that is not found in the human proteome). In some examples, the heterologous peptide is about 8 amino acids to about 20 amino acids in length, such about 10 to about 18 amino acids in length, such as about 12 to about 16 amino acids in length, such as about 14 amino acids in length. In particular examples, the heterologous peptide is about 8, 9, 10, 11, 12, 13, 14, 15, 16, 17, 18, 19 or 20 amino acids in length. In a specific non-limiting example, the PNE comprises or consists of NYHLENEVARLKKL (SEQ ID NO: 26).

VII. Antibody-Drug Conjugates (ADCs)

ADCs are compounds comprised of a tumor antigen-specific antibody (or antigen-binding fragment thereof) and a drug, typically a cytotoxic agent, such as an anti-microtubule agent or cross-linking agent. Because ADCs are capable of specifically targeting cancer cells, the drug can be much more potent than agents used for standard chemotherapy. The most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as a cytotoxic agent) conjugated to a monoclonal antibody that binds (such as specifically binds) GPC2. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, *vinca* alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc*, 87:5793-5795, 1965; Leimgruber et al., *J Am Chem Soc*, 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663,149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of a GPC2-positive cancer alone or in combination with another therapeutic agent and/or in combination with any standard therapy for the treatment of cancer (such as surgical resection of the tumor, chemotherapy or radiation therapy).

VIII. Multi-Specific Antibodies

Multi-specific antibodies are recombinant proteins comprised of antigen-binding fragments of two or more different monoclonal antibodies. For example, bispecific antibodies are comprised of antigen-binding fragments of two different monoclonal antibodies. Thus, bispecific antibodies bind two different antigens and trispecific antibodies bind three different antigens. Multi-specific antibodies can be used for cancer immunotherapy by simultaneously targeting, for example, both CTLs (such as a CTL receptor component such as CD3) or effector natural killer (NK) cells, and at least one tumor antigen. The GPC2-specific monoclonal antibodies disclosed herein can be used to generate multi-specific (such as bispecific or trispecific) antibodies that target both GPC2 and CTLs, or target both GPC2 and NK cells, thereby providing a means to treat GPC2-expressing cancers.

Bi-specific T-cell engagers (BiTEs) are a type of bispecific monoclonal antibody that are fusions of a first single-chain variable fragment (scFv) that targets a tumor antigen and a second scFv that binds T cells, such as bind CD3 on T cells. In some embodiments herein, one of the binding moieties of the BiTE (such as one of the scFv molecules) is specific for GPC2.

Bi-specific killer cell engagers (BiKEs) are a type of bispecific monoclonal antibody that are fusions of a first scFv that targets a tumor antigen and a second scFv that binds a NK cell activating receptor, such as CD16.

Provided herein are multi-specific, such as trispecific or bispecific, monoclonal antibodies comprising a GPC2-specific single domain antibody. In some embodiments, the multi-specific monoclonal antibody further comprises a monoclonal antibody, or antigen-binding fragment thereof, that specifically binds a component of the T cell receptor, such as CD3. In other embodiments, the multi-specific monoclonal antibody further comprises a monoclonal antibody, or antigen-binding fragment thereof, that specifically binds a NK cell activating receptor, such as CD16, Ly49, or CD94. Also provided are isolated nucleic acid molecules and vectors encoding the multi-specific antibodies, and host cells comprising the nucleic acid molecules or vectors. Multi-specific antibodies comprising a GPC2-specific antibody can be used for the treatment of cancers that express GPC2. Thus, provided herein are methods of treating a subject with cancer by selecting a subject with a cancer that expresses GPC2, and administering to the subject a therapeutically effective amount of the GPC2-targeting multi-specific antibody.

IX. Antibody-Nanoparticle Conjugates

The VH single domain monoclonal antibodies disclosed herein can be conjugated to a variety of different types of nanoparticles to deliver cytotoxic agents or other anti-cancer agents directly to tumor cells via binding of the antibody to a tumor specific antigen (e.g. GPC2) expressed on the surface of tumor cells. The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, *Immunotherapy* 3(3):381-394, 2011).

Liposomes are currently one of the most common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, Curr Med Chem 19(31)5239-5277, 2012; Immordino et al., Int J Nanomedicine 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine Niosomes range from small, unilamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents and chemotherapeutic agents.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core. Polymeric micelles can be used to carry drugs that have poor solubility. These nanoparticles have been used to encapsulate a number of anti-cancer drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within a nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly(glycolic acids) (PGA), and poly(D,L-lactic-co-glycolic acid) (PLGA).

Antibodies, including single-domain antibodies, can be conjugated to a suitable nanoparticle according to standard methods known in the art. For example, conjugation can be either covalent or non-covalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, Curr Med Chem 19(31)5239-5277, 2012).

X. Compositions and Methods of Use

Compositions are provided that include one or more of the disclosed VH single domain antibodies that bind (for example specifically bind) GPC2 in a carrier. Compositions comprising ADCs, CARs (and CTLs comprising CARs), multi-specific (such as bispecific or trispecific) antibodies, antibody-nanoparticle conjugates, immunoliposomes and immunoconjugates are also provided. The compositions can be prepared in unit dosage forms for administration to a subject. The amount and timing of administration are at the discretion of the treating clinician to achieve the desired outcome. The antibody, ADC, CAR, CTL, multi-specific antibody, antibody-nanoparticle conjugate, immunoliposome or immunoconjugate can be formulated for systemic or local (such as intra-tumor) administration. In one example, the antibody is formulated for parenteral administration, such as intravenous administration.

The compositions for administration can include a solution of the antibody, ADC, CAR, CTL, multi-specific (such as bispecific or trispecific) antibody, antibody-nanoparticle conjugate, immunoliposome or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, multi-specific antibody, antibody-nanoparticle conjugate, or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as Remington's Pharmaceutical Science, 19th ed., Mack Publishing Company, Easton, Pa. (1995).

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S.

since the approval of RITUXAN™ in 1997. Antibodies, ADCs, CARs, multi-specific (such as bispecific or trispecific) antibodies, antibody-nanoparticle conjugates, immunoliposomes or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies, compositions, CARs (and CTLs expressing CARs), ADCs, multi-specific (such as bispecific or trispecific) antibodies, antibody-nanoparticle conjugates, immunoliposomes and immunoconjugates disclosed herein can be administered to slow or inhibit the growth of tumor cells or inhibit the metastasis of tumor cells, such as GPC2-positive cancers. In these applications, a therapeutically effective amount of a composition is administered to a subject in an amount sufficient to inhibit growth, replication or metastasis of cancer cells, or to inhibit a sign or a symptom of the cancer. Suitable subjects may include those diagnosed with a cancer that expresses GPC2, such as, but not limited to neuroblastoma, acute lymphoblastic leukemia, embryonal rhabdomyosarcoma, alveolar rhabdomyosarcoma, Ewing's sarcoma, desmoplastic small round cell tumor or osteosarcoma.

Provided herein is a method of treating a GPC2-positive cancer in a subject by administering to the subject a therapeutically effective amount of a GPC2-specific antibody, immunoconjugate, CAR (e.g. a CTL expressing a CAR), ADC, multi-specific (such as bispecific or trispecific) antibody, antibody-nanoparticle conjugate, immunoliposome or composition disclosed herein. Also provided herein is a method of inhibiting tumor growth or metastasis of a GPC2-positive cancer in a subject by administering to the subject a therapeutically effective amount of a GPC2-specific antibody, immunoconjugate, CAR (e.g. a CTL expressing a CAR), ADC, multi-specific (such as bispecific or trispecific) antibody, antibody-nanoparticle conjugate, immunoliposome or composition disclosed herein. In some embodiments, the GPC2-positive cancer is a neuroblastoma, acute lymphoblastic leukemia, embryonal rhabdomyosarcoma, alveolar rhabdomyosarcoma, Ewing's sarcoma, desmoplastic small round cell tumor or osteosarcoma.

A therapeutically effective amount of a GPC2-specific VH single domain antibody, ADC, CAR (e.g. a CTL expressing a CAR), multi-specific (such as bispecific or trispecific) antibody, immunoconjugate, immunoliposome or composition disclosed herein will depend upon the severity of the disease, the type of disease, and the general state of the patient's health. A therapeutically effective amount of the antibody-based composition is that which provides either subjective relief of a symptom(s) or an objectively identifiable improvement as noted by the clinician or other qualified observer.

Administration of the GPC2-specific antibodies, ADCs, CARs, immunoconjugates, multi-specific (such as bispecific or trispecific) antibodies, antibody-nanoparticle conjugates, immunoliposomes and compositions disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, antimetabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting GPC2 protein in vitro or in vivo. In some cases, GPC2 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

Provided herein is a method of determining if a subject has a GPC2-positive cancer by contacting a sample from the subject with a GPC2-specific single domain monoclonal antibody disclosed herein; and detecting binding of the antibody to the sample. An increase in binding of the antibody to the sample as compared to binding of the antibody to a control sample identifies the subject as having a GPC2-positive cancer.

In another embodiment, provided is a method of confirming a diagnosis of a GPC2-positive cancer in a subject by contacting a sample from a subject diagnosed with a GPC2-positive cancer with a GPC2-specific single domain monoclonal antibody disclosed herein; and detecting binding of the antibody to the sample. An increase in binding of the antibody to the sample as compared to binding of the antibody to a control sample confirms the diagnosis of a GPC2-positive cancer in the subject.

In some examples of the disclosed methods, the monoclonal antibody is directly labeled.

In other examples, the methods further include contacting a second antibody that specifically binds the monoclonal antibody with the sample; and detecting the binding of the second antibody. An increase in binding of the second antibody to the sample as compared to binding of the second antibody to a control sample detects a GPC2-positive cancer in the subject or confirms the diagnosis of a GPC2-positive cancer in the subject.

In some cases, the cancer is a neuroblastoma, acute lymphoblastic leukemia, embryonal rhabdomyosarcoma, alveolar rhabdomyosarcoma, Ewing's sarcoma, desmoplastic small round cell tumor or osteosarcoma.

In some examples, the control sample is a sample from a subject without cancer. In particular examples, the sample is a blood or tissue sample.

In some embodiments of the methods of diagnosis and detection, the antibody that binds (for example specifically binds) GPC2 is directly labeled with a detectable label. In another embodiment, the antibody that binds (for example, specifically binds) GPC2 (the first antibody) is unlabeled and a second antibody or other molecule that can bind the antibody that specifically binds GPC2 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, GPC2 can be assayed in a biological sample by a competition immunoassay utilizing GPC2 protein standards labeled with a detectable substance and an unlabeled antibody that specifically binds GPC2. In this assay, the biological sample, the labeled GPC2 protein standards and the antibody that specifically bind GPC2 are combined and the amount of labeled GPC2 protein standard bound to the unlabeled antibody is determined. The amount of GPC2 in the biological sample is inversely proportional to the amount of labeled GPC2 protein standard bound to the antibody that specifically binds GPC2.

The immunoassays and methods disclosed herein can be used for a number of purposes. In one embodiment, the antibody that specifically binds may be used to detect the production of GPC2 in cells in cell culture. In another embodiment, the antibody can be used to detect the amount of GPC2 in a biological sample, such as a tissue sample, or a blood or serum sample. In some examples, the GPC2 is cell-surface GPC2. In other examples, the GPC2 protein is soluble (e.g. in a cell culture supernatant or in a body fluid sample, such as a blood or serum sample).

In one embodiment, a kit is provided for detecting GPC2 in a biological sample, such as a blood sample or tissue sample. For example, to confirm a cancer diagnosis in a subject, a biopsy can be performed to obtain a tissue sample for histological examination. Kits for detecting a polypeptide will typically comprise a monoclonal antibody that specifically binds GPC2, such as any of the single domain antibodies disclosed herein. In a further embodiment, the antibody is labeled (for example, with a fluorescent, radioactive, or an enzymatic label).

In one embodiment, a kit includes instructional materials disclosing means of use of an antibody that binds GPC2. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting GPC2 in a biological sample generally includes the steps of contacting the biological sample with an antibody which specifically reacts, under immunologically reactive conditions, to GPC2. The antibody is allowed to specifically bind under immunologically reactive conditions to form an immune complex, and the presence of the immune complex (bound antibody) is detected directly or indirectly.

The antibodies disclosed herein can also be utilized in immunoassays, such as, but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the single-domain monoclonal antibodies that bind GPC2, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1: Materials and Methods

This example describes the experimental procedures and materials used for the studies described in Example 2.
Cell Culture Six neuroblastoma cell lines, including SKNSH, LAN1, LAN5, IMR5, IMR32 and NBEB, were used in the studies disclosed herein. IMR5, LAN1 and SKNSH cell lines were also transduced with lentiviruses expressing firefly luciferase (Day et al., *Pigment Cell Melanoma Res* 22(3):283-295, 2009). Peripheral blood mononuclear cells (PBMCs) were isolated from peripheral blood of eight healthy donors using FICOLL™ according to the manufacturer's instructions. The aforementioned cell lines were cultured in RPMI-1640 medium supplemented with 10% fetal bovine serum, 1% L-glutamine and 1% penicillin-streptomycin at 37° C. in a humidified atmosphere with 5% $CO_2$. The HEK-293T cell line (obtained from the American Type Culture Collection) and the HEK293 SuperTopflash stable cell line were grown in DMEM medium supplemented with 10% fetal bovine serum, 1% L-glutamine and 1% penicillin-streptomycin at 37° C. in a humidified atmosphere with 5% $CO_2$. All cell lines were authenticated by morphology and growth rate and were mycoplasma free.
Preparation and Purification of GPC2

To make recombinant GPC2 protein, the predicted N-terminal secretion signal and C-terminal GPI attachment peptide were removed, a sequence coding for amino acids 24-553 was fused to a human IgG Fc (hFc) at the C terminus, and an IL-2 secretion signal was added at the N terminus. The plasmid was transfected into 293T cells using polyethylenimine (PEI). The GPC2-hFc protein was harvested from the culture supernatant and purified with HITRAP™ protein A column (GE Healthcare).
Phage Display and Biopanning A combinational engineered human VH single domain library, with an estimated size of $2.5 \times 10^{10}$ was used for screening and has been previously described (Chen et al., *J Mol Biol* 382:779-789, 2008). The phage library was subjected to four rounds of panning on Nunc 96-well Maxisorp plate (Thermo Scientific) as described previously (Ho and Pastan, *Methods Mol Biol* 525:293-308, 2009; Ho et al., *J Biol Chem* 280:607-617, 2005; Feng et al., *Proc Natl Acad Sci USA* 110, E1083-E1091, 2013). The recombinant GPC2-hFc fusion protein used for panning was prepared following a published protocol (Feng et al., *Proc Natl Acad Sci USA* 110, E1083-E1091, 2013). The 96-well Maxisorp plate was coated with 100 µg/ml GPC2-hFc in PBS overnight at 4° C. Both the plate and $10^{11}$-$10^{12}$ plaque forming units (pfu) of phage were blocked with 3% skim milk in PBS/0.05% Tween-20 for 1 hour at room temperature. Then pre-blocked phage supernatant was added to each well to allow binding. After 1 hour of incubation at room temperature, the unbound and nonspecifically bound phages were removed using 5 washes with PBS/0.05% Tween-20. The specifically bound phage was eluted with 100 µl pH 2.0 elution buffer for 10 minutes at room temperature. The eluate was neutralized with 30 µl of 1M Tris base and was used to infect freshly prepared *E. coli* TG1 cells. After four rounds of panning, 96 randomly picked clones were analyzed for GPC2 binding by phage ELISA.
Antibody Expression and Purification The coding sequences of the anti-GPC2 antibodies were fused with either hFc or mouse IgG Fc (mFc), and then cloned into an expression plasmid pVRC8400 (Feng et al., *Proc Natl Acad Sci USA* 110, E1083-1091, 2013). The plasmids were transiently transfected into HEK-293T cells using PEI. The antibodies fused with hFc and mFc were harvested from culture supernatants and purified with HITRAP™ protein A column and protein G column (GE Healthcare), respectively.
Antibody Binding Assay The binding kinetics of the LH7 antibody to GPC2 was determined using the Octet RED96 system (ForteBio) as described previously (Maus and June, *Clin Cancer Res* 22(8):1875-1884, 2016). Briefly, all experiments were performed at 30° C. and reagents were prepared in 0.1% BSA, 0.1% Tween20 PBS, pH 7.4 buffer. Biotinylated GPC2-hFc protein was immobilized onto Streptavidin biosensors, which were subsequently used in association and dissociation measurements for a time window of 600 seconds and 1800 seconds, respectively. Data analysis was performed using the ForteBio analysis software provided with the instrument.

ELISA

The phage ELISA was performed as previously described (Ho and Pastan, *Methods Mol Biol* 525:293-308, 2009; Ho et al., *J Biol Chem* 280:607-617, 2005). Briefly, Nunc MaxiSorp 96-well flat-bottomed plates were coated with 50 µl of 5 µg/ml GPC2-hFc overnight at 4° C. Both plate and phage were blocked with 3% skim milk in PBS/0.05% Tween-20 for 1 hour at room temperature. Then pre-blocked phage supernatant was added to the plate. Binding was detected by HRP-conjugated mouse anti-M13 antibody (GE Healthcare). To measure the affinities of anti-GPC2 immunotoxins, Nunc MaxiSorp 96-well plates were coated with GPC2-hFc fusion protein. Then a series of diluted immunotoxins were added to each well. Anti-*Pseudomonas* exotoxin A antibody (Sigma-Aldrich) and HRP-conjugated secondary antibody (Jackson Immunoresearch) were used to detect binding. $EC_{50}$ values were determined by Prism 6.0 software (GraphPad).

Flow Cytometry

Cells were trypsinized into single-cell suspension and then incubated with 100 µg/ml of LH7 antibody and hIgG isotype control (Sigma-Aldrich) in FACS buffer (5% BSA in PBS) for 1 hour on ice. Bound antibodies were detected by incubating with a 1:200 dilution of goat anti-mouse IgG-phycoerythrin (PE) secondary antibody (Invitrogen) in FACS buffer for 1 hour on ice. The fluorescence associated with the live cells was measured using a FACS Calibur (BD Biosciences). The average number of GPC2 sites per cell was measured on a FACS Calibur using BD Quantibrite PE beads (BD Biosciences) according to the manufacturer's instructions. For detection of transduction efficiency of CARs on T cells, GFP expression was used to monitor transduced T cells. Data analysis was carried out using FlowJo software (Tree Star).

Immunohistochemistry

The human neuroblastoma tissue array and normal tissue array were purchased from US Biomax. Mounted tissue sections were deparaffinized with xylene and rehydrated in decreasing concentrations of ethanol. After antigen retrieval, endogenous peroxidase activity was inactivated in 3% hydrogen peroxide solution. The sections were blocked by 3% BSA, then incubated with 1 µg/ml LH7-mFc antibody for 2 hours at room temperature. After rinsing with Tris/0.05% Tween-20 buffer, sections were incubated at room temperature for 30 minutes with horseradish peroxidase (HRP)-conjugated goat anti-mouse antibody. 3,3'-diaminobenzidine (DAB) reactions were performed following washes in Tris/0.05% Tween-20 buffer. Sections were counterstained with hematoxylin for 1 minute, dehydrated and mounted with permount mounting medium.

Western Blotting

Cells were harvested, vortexed in ice-cold lysis buffer (Cell Signaling Technology), and clarified by centrifugation at 10,000×g for 10 minutes at 4° C. Protein concentration was measured using Coomassie blue assay (Pierce) following the manufacturer's specifications. Twenty µg of cell lysates were loaded into 4-20% SDS-PAGE gel for electrophoresis. The anti-GPC2 antibody was purchased from Santa Cruz Biotechnology. The anti-active-β-catenin antibody was obtained from Millipore. All other antibodies were purchased from Cell Signaling Technology.

Production of Recombinant Immunotoxin

Anti-GPC2 single chain antibodies were cloned into pRB98 expression plasmid in which the fragment was fused to a *Pseudomonas* exotoxin A (PE38). The expression and purification of recombinant immunotoxins were performed following a protocol described previously (Pastan and Ho, *Antibody Engineering*, Springer, 2010).

Human Normal Tissue cDNA Array

The human normal tissue array was purchased from Origene (Rockville, Md.). The panel containing 48 samples covering all major human normal tissues at different locations were used to evaluate GPC2 expression according to the manufacturer's recommendation. Tissue cDNAs were synthesized from high quality total RNAs of pathologist-verified tissues, normalized and validated with GAPDH. The GPC2 primer and RT2 SYBR Green qPCR Mastermix were purchased from Qiagen (Germantown, Md.). Real-time quantification was performed on an Applied Biosystems 7900HT real-time PCR system. The results were analyzed using the $2^{-\Delta\Delta Ct}$ method.

siRNA-Mediated Knockdown of GPC2

Three siRNAs targeting human GPC2 and scrambled control siRNA were purchased from Dharmacon. LAN1 and IMR5 cells were transfected with siRNAs using DHARMAFECT™ transfection reagent (Dharmacon) according to the manufacturer's specifications. Cells were then incubated at 37° C. for up to 72 hours post-transfection. Sequences of GPC2 siRNAs are listed in Table 3.

TABLE 3 siRNAs targeting human GPC2

| siRNA | Sequence | SEQ ID NO: |
|---|---|---|
| siRNA-1 | GGAUAUAGCUUAAACCUAA | 23 |
| siRNA-2 | CAACGUGGUUCGUGGCUGU | 24 |
| siRNA-3 | GAAGAUCUCGGAGGGUUUG | 25 |

Construction of GPC2 Knockout Cell Lines

Three sgRNAs targeting human GPC2 are listed in the following table. The lentiCRISPRv2 expression vector was used (Addgene plasmid #52961). sgRNAs targeting human GPC2 were designed based on CHOPCHOP, and are listed in Table 4. The lentiCRISPRv2 plasmid was digested with BsmBI and gel purified using the Gel extraction kit (Qiagen). A pair of oligonucleotides for each targeting site were annealed and ligated into linearized lentiCRISPRv2 vector for generating gRNA-expressing plasmid following a protocol described previously (Sanjana et al., *Nat Methods* 11:783-784, 2014; Shalem et al., *Science* 343:84-87, 2014). Lentiviruses expressing the sgRNAs were produced by transfecting HEK-0293T cells with Mission Lentiviral Packaging Mix (Sigma-Aldrich). LIPOFECTAMINE™ 2000 was used as transfection reagent according to the manufacturer's instructions (Invitrogen). The GPC2 knockout neuroblastoma cells were infected with lentivirus in the presence of 8 µg/ml polybrene (Sigma-Aldrich). After 24 hours of transduction, infected cells were selected with puromycin for 7 days. The pooled GPC2 knockout cells were confirmed by western blotting.

TABLE 4

The sequences of sgRNAs targeting human GPC2

| sgRNA | Sequence | SEQ ID NO: | PAM sequence | GPC2 exon |
|---|---|---|---|---|
| sgRNA-1 | GGACCAGGACCGGGACACAG | 20 | AGG | 1 |
| sgRNA-2 | GAACAGCAGGTGTACTCCTG | 21 | GGG | 2 |
| sgRNA-3 | GAGGCAGAGCAGGTAGTCAG | 22 | GGG | 3 |

Cell Proliferation Assay

Cells were seeded in 96-well plates at a density of 5,000 cells per well. After overnight culture, cells were treated with immunotoxins and incubated at 37° C. for 72 hours. The effect of treatment on cell growth was measured using WST-8 assay as specified by the manufacturer (Dojindo Molecular Technologies) following a previously described protocol (Ho and Pastan, *Methods Mol Biol* 525:293-308, 2009; Ho et al., *J Biol Chem* 280:607-617, 2005). The inhibition of cell growth caused by GPC2 siRNA was determined after 72 hours of treatment using the luminescent CELLTITER-GLO™ assay (Promega), which measured viable cells based on ATP content.

Caspase 3/7 Assay

The GPC2 knockout and vector control cells were seeded in 96-well plates at a density of 5,000 cells per well, and incubated for 72 hours. The induction of apoptosis was determined using luminescent Caspase-Glo 3/7 assay (Promega), which measures cleavage of a substrate for caspase-3 and caspase-7. The assay was performed according to the manufacturer's specifications.

Treatment in HEK293 Supertopflash Cells

To determine the effect of LH7 antibody on β-catenin levels, HEK293 Supertopflash cells were starved overnight and pretreated with different concentrations of LH7. An hour later, equal volumes of Wnt3a conditioned medium (CM) were added. Active β-catenin expression levels were detected by western blotting 6 hours later. For the treatment involving LiCl, HEK293 Supertopflash cells were starved overnight and pretreated with or without 100 μg/ml LH7 for an hour. Then equal volumes of Wnt3a CM (combined with or without 20 mM LiCl or NaCl) were added. β-catenin levels were measured by western blotting after a 6 hour treatment.

Luciferase Reporter Assay

Wnt luciferase reporter assay was conducted following a published protocol (Gao et al., *Hepatology* 60:576-587, 2014; Gao et al., *Nat Commun* 6:6536, 2015). Briefly, HEK293 SuperTopflash cells were seeded into 48-well plates at a density of $7 \times 10^4$ cells per well. After overnight attachment, cells were serum-starved for 24 hours, and then treated with different concentrations of LH7 antibody. After 1 hour, an equal volume of Wnt3a CM was added. Luciferase activity was measured and normalized with total protein after 6 hours of treatment.

Generation of GPC2-Specific CAR

The anti-GPC2 CAR comprising the isolated anti-GPC2 heavy chain antibody fragment was linked in-frame to the hinge domain of CD8a hinge and transmembrane domain, which was fused to the 4-1BB and CD3 intracellular TCR signaling domains. The construct was engineered to express an upstream GFP reporter separated from the CAR by a T2A sequence. The sequence encoding the whole CAR construct was subcloned into the lentiviral vector pLenti6.3/v5 (Invitrogen) bearing the CMV promoter.

Lentivirus Production, T-Cell Transduction and Expansion

To produce viral supernatant, HEK-293T cells were co-transfected with GPC2-CAR lentiviral vectors and Mission viral packaging plasmids (Sigma-Aldrich) using LIPO-FECTAMINE™ 2000 (Invitrogen) per the manufacturer's protocol. The supernatant was collected at 72 hours post-transfection, mixed with Lenti-X concentrator (Clontech) according to the manufacturer's instructions.

PBMCs were purchased from Oklahoma Blood Institute and stimulated for 24 hours with anti-CD3/anti-CD28 antibodies coated beads (Invitrogen) at a 2:1 bead-to-T-cell ratio in growth medium supplemented with IL-2. Activated T cells were then transduced with the lentivirus expressing GPC2-specific CARs at a multiplicity of infection (MOI) of 5. Cells were counted every other day and fed with fresh growth medium every 2-3 days. Once T cells appeared to become quiescent, as determined by both decreased growth kinetics and cell size, they were used either for functional assays or cryopreserved.

T Cell Effector Assays

Effector T cells were co-cultured with luciferase expressing neuroblastoma cells at different ratios for 24 hours. At the end of the co-culture incubation period, supernatant was saved for IFN-γ and TNF-α levels by ELISA (R&D Systems). The remaining tumor cells were lysed for 5 minutes. The luciferase activity in the lysates was measured using the STEADY-GLO™ luciferase assay system on Victor (PerkinElmer). Results are analyzed as percent killing based on luciferase activity in wells with tumor cells alone (% killing=100−((RLU from well with effector and target cells)/(RLU from wells with target cells)×100)).

Animal Studies

For xenograft tumor studies, five-week-old female athymic nu/nu nude mice (NCI-Frederick) were given subcutaneous injections of $10 \times 10^6$ LAN1 cells suspended in Matrigel (Corning). Tumor dimensions were determined using calipers, and tumor volume (mm$^3$) was calculated by the formula V=½ ab$^2$, where a and b represent tumor length and width, respectively. For LH7-PE38 treatment, when average tumor size reached around 150 mm$^3$, mice were intravenously injected with indicated doses every other day for 10 injections. For T cell treatment, when tumor burden was approximately 120 mm$^3$, mice were injected intraperitoneally (i.p.) with 200 mg/kg cyclophosphamide to deplete host lymphocyte compartments. After 24 hours, $10 \times 10^6$ of either mock T cells or LH7 CAR T cells were intravenously injected into mice on Days 13, 20 and 27. Mice were given i.p. injection of 2000U IL-2 twice a week following T cell infusion. Mice were euthanized when the tumor size reached 1500 mm$^3$.

For the disseminated tumor study, five-week-old female athymic nu/nu nude mice were intravenously injected with $7 \times 10^6$ luciferase expressing IMR5 cells. Cyclophosphamide was injected i.p. at 200 mg/kg 24 hours before any cell administration. Then animals were given a single infusion of $30 \times 10^6$ mock T cells or LH7 CAR T cells by tail vein injection. Disease was detected using the Xenogen IVIS Lumina (PerkinElmer). Nude mice were injected i.p. with 3 mg D-luciferin (PerkinElmer) and imaged 10 minutes later. Living Image software was used to analyze the bioluminescence signal flux for each mouse as photons/s/cm$^2$/sr. Mice were euthanized when mice showed any sign of sickness or bioluminescence signal reached $1 \times 10^9$.

Toxicological Analysis

Three nude mice from each group were chosen for toxicology studies. Samples were processed for completed blood counts (CBC), comprehensive serum chemistry (VetScan, Abaxis Veterinary Diagnostics, Union City, Calif.) and internal organ weights.

Statistical Analysis

All experiments were repeated a minimum of three times to determine the reproducibility of the results. All error bars represent standard error of the mean (SEM). Statistical analysis of differences between samples was performed using the Student's t-test. A P value of <0.05 was considered statistically significant.

Example 2

This example describes the identification and characterization of a panel of anti-GPC2 antibodies.

Discovery of Anti-GPC2 Human Monoclonal Antibodies

Figure 1B:
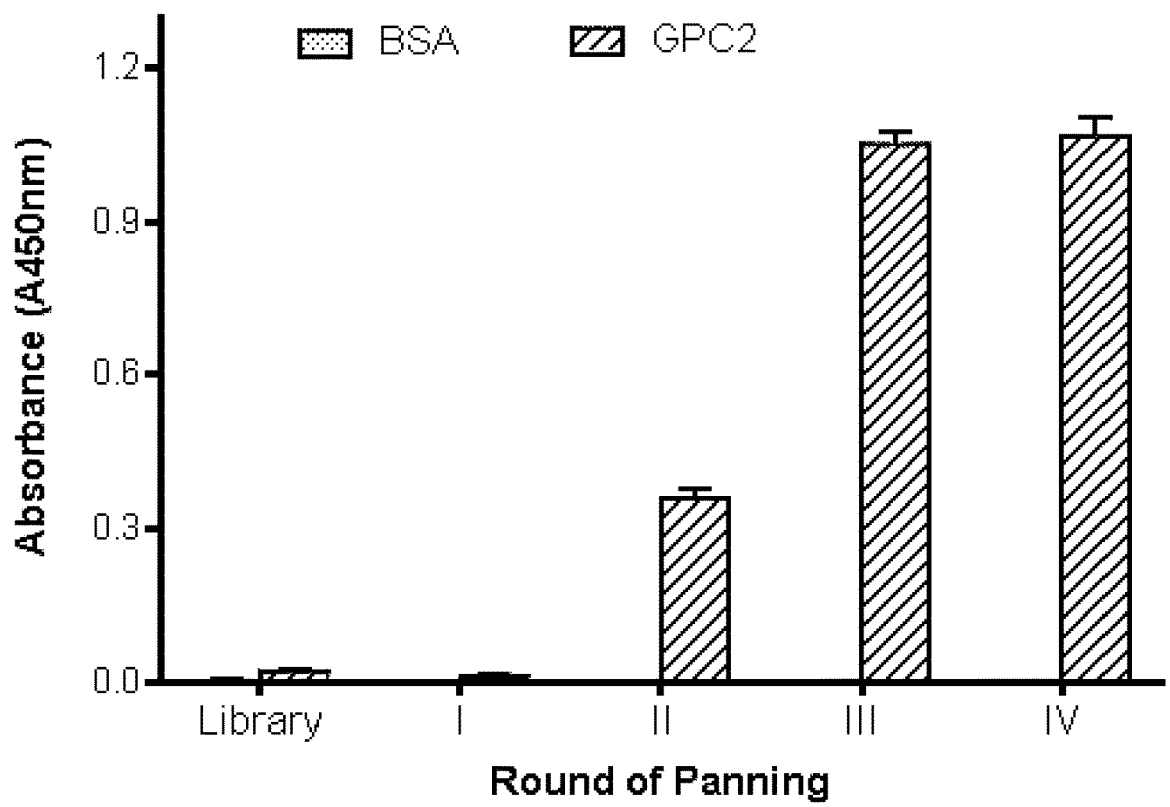
Figure 1C:
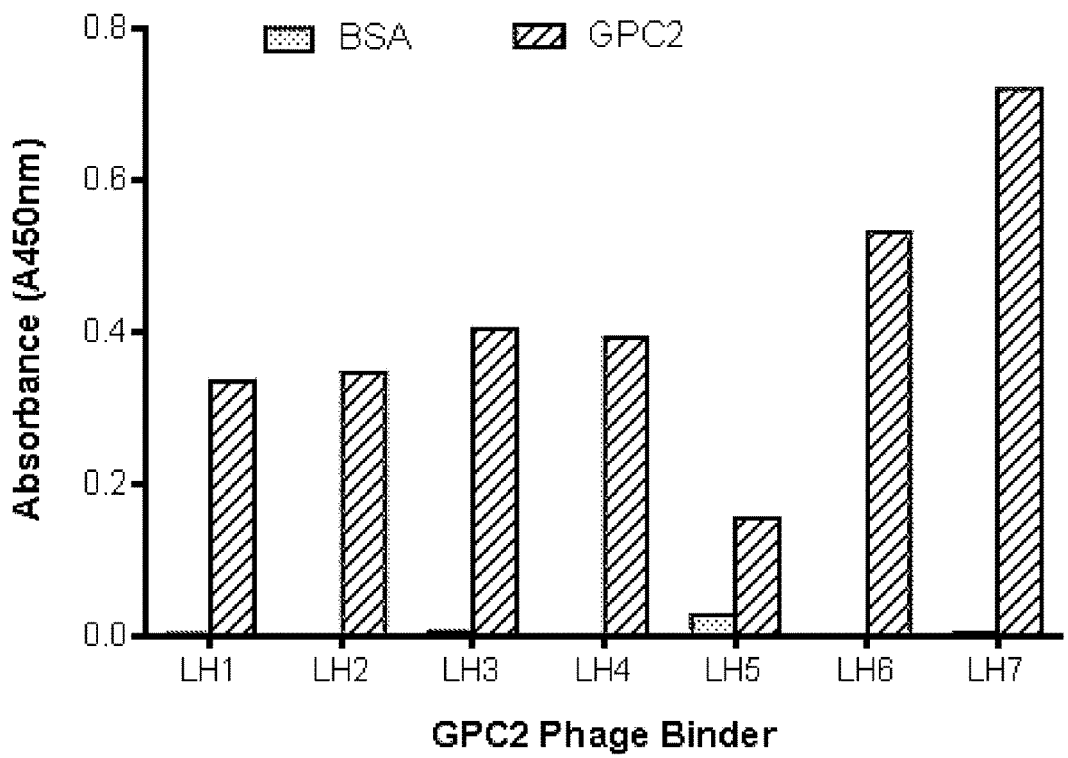
Figure 1D:
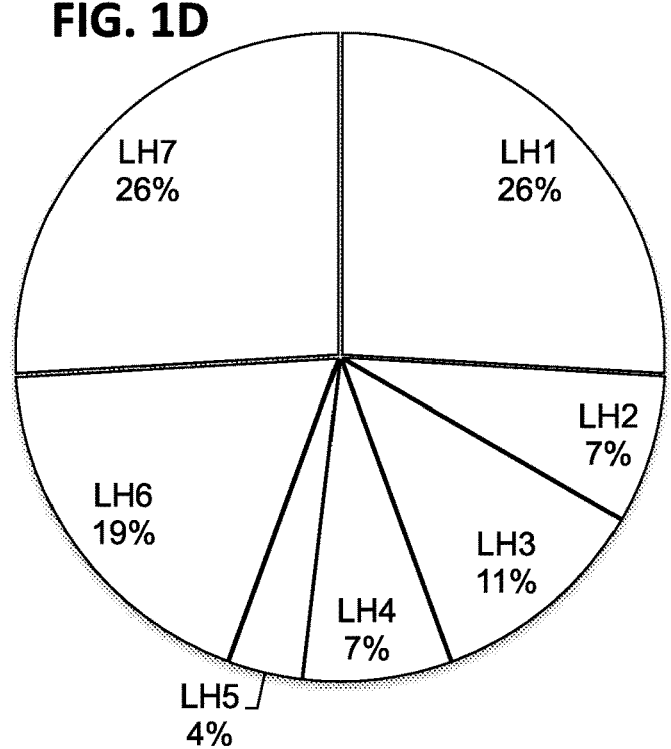

To identify antibodies specific for GPC2, a phage-display technology was utilized to isolate a group of human monoclonal antibodies. GPC2 was made as a recombinant protein in human HEK-293T cells. A phage-display engineered VH single domain antibody library was screened by four rounds of panning on a 96-well ELISA plate coated with GPC2 protein. Enrichment was determined to check the number of phages recaptured after each round of panning by counting the colony forming units (CFU) of the infected *E. coli* TG1. As shown in FIG. 1A, four rounds of panning resulted in an approximately 1000-fold enrichment of eluted phage. Phage pools after two rounds of panning exhibited enhanced binding to GPC2, whereas no binding to BSA was found with pooled phage from any of the four rounds of panning (FIG. 1B). At the end of the fourth round of panning, 192 clones were selected randomly, and 27 of these clones were confirmed to be GPC2 binders by monoclonal phage ELISA. Subsequent sequencing analysis revealed seven unique binders (LH1, LH2, LH3, LH4, LH5, LH6 and LH7). The GPC2-hFc $OD_{450\ nm}$ values of all seven clones were at least 5-fold higher than that of BSA (FIG. 1C), further indicating the specificity of the phages to GPC2. LH1 and LH7 were the two most abundant binders among all seven binders, as shown in FIG. 1D. The LH5 clone was excluded from further study due to its low affinity for GPC2.

Figure 1E:
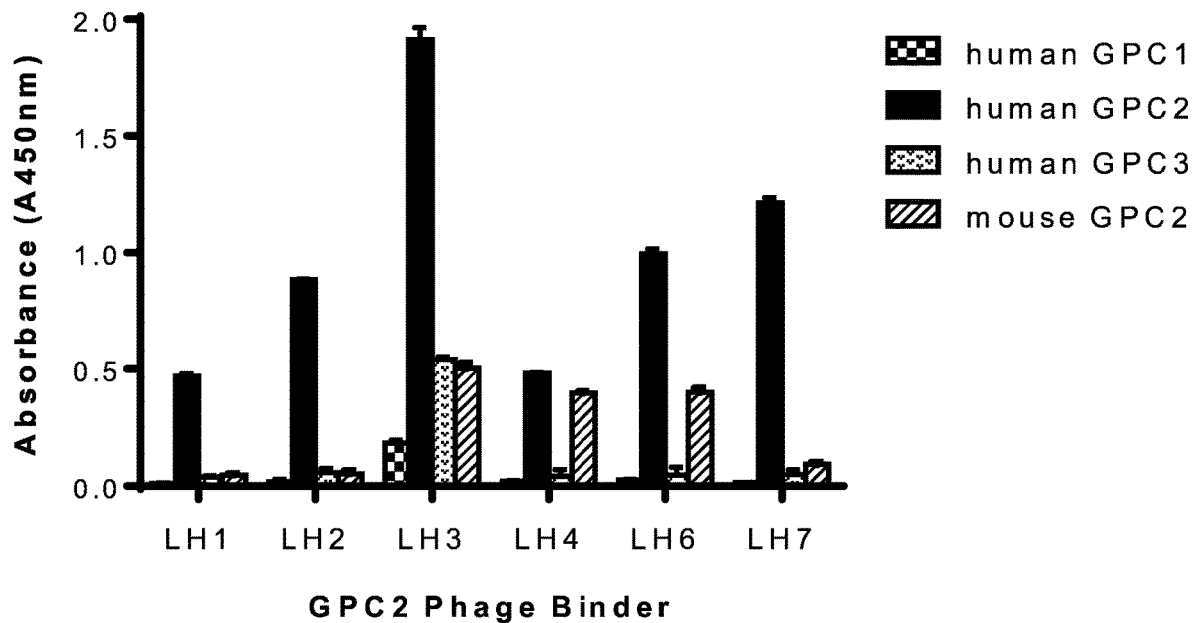
Figure 1F:
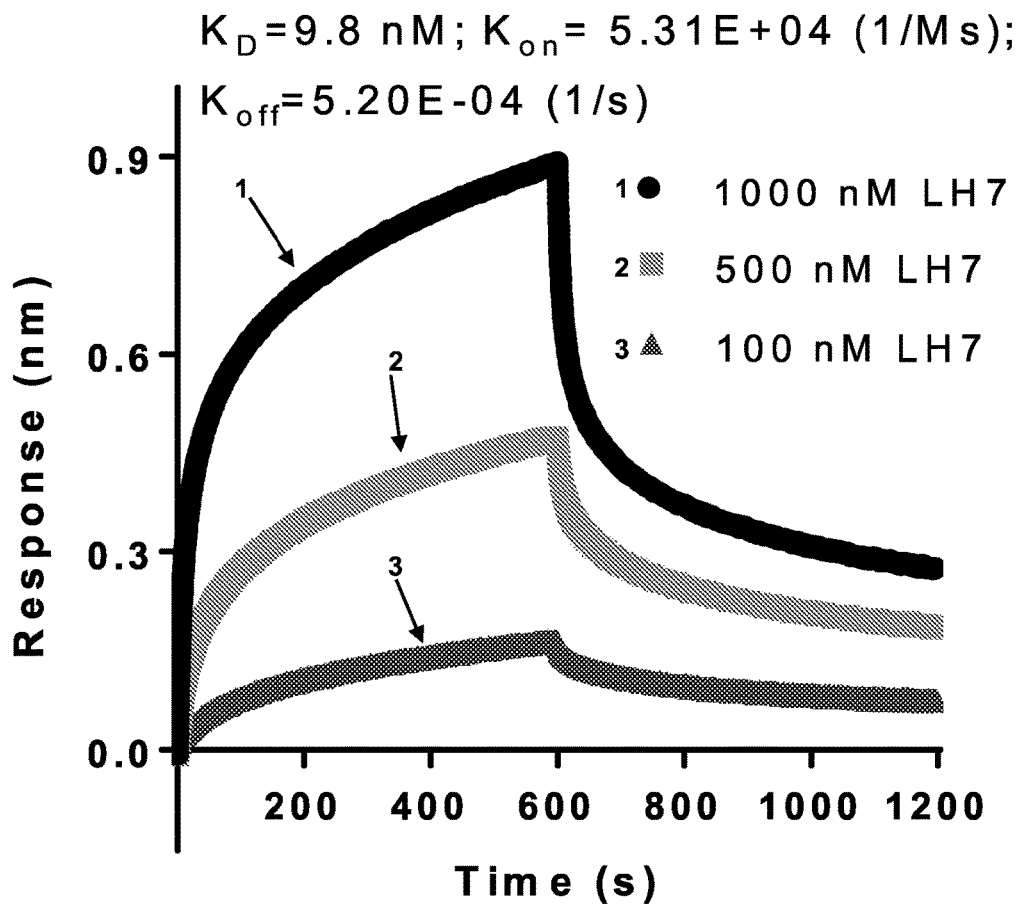

To determine whether these clones bind to other members of the human glypican family, monoclonal phage ELISA was performed using recombinant human GPC1, GPC2 and GPC3, as well as mouse GPC2 proteins. As shown in FIG. 1E, five clones including LH1, LH2, LH4, LH6 and LH7 specifically bound to human GPC2, but not human GPC1 or GPC3. LH4 and LH6 also bound to mouse GPC2. LH3 showed the highest affinity to human GPC2 among all binders, but it was slightly cross-reactive with GPC1 and GPC3. To determine binding kinetics, a LH7-Fc fusion protein was produced and incubated with GPC2 protein in solution on the Octet platform. The $K_D$ value of the LH7-Fc fusion for GPC2 was 9.8 nM (FIG. 1F). Taken together, a group of high-affinity anti-GPC2 human single domain antibodies were successfully identified by phage display.

Expression of GPC2 in Human Neuroblastoma and Normal Tissues

Figure 2A:
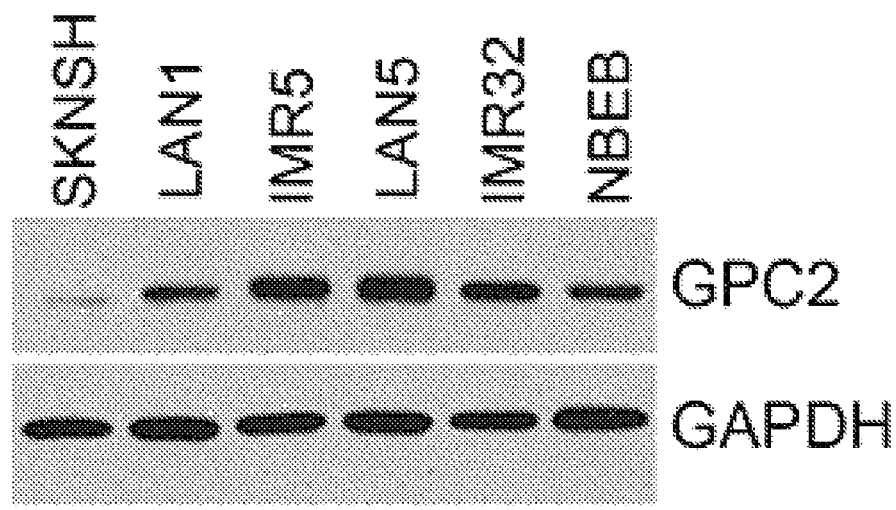
FIGS. 2A-2C: GPC2 expression in human neuroblastoma tumors and normal human tissues.

A previous microarray study showed that GPC2 mRNA was overexpressed in a panel of pediatric cancers including neuroblastoma (Orentas et al., *Front Oncol* 2:194, 2012). To examine GPC2 protein expression in neuroblastoma, the anti-GPC2 antibodies were used as research tools to examine established human cell lines and clinical tissue samples. Western blotting data demonstrated that GPC2 was highly expressed in five neuroblastoma cell lines, including LAN1, IMR5, LAN5, IMR32 and NBEB (FIG. 2A). GPC2 was weakly detected in SKNSH neuroblastoma cells. To assess the clinical relevance of this observation, GPC2 protein levels were measured in human specimens from patients with neuroblastoma or non-malignant disease by immunohistochemistry studies using the LH7 antibody. GPC2 labeling was readily apparent in specimens derived from patients with neuroblastoma, but essentially undetectable in normal peripheral nerves from patients with non-malignant disease. Neuroblastoma tumor tissues showed strong GPC2 staining in 13 of the 25 cases (52%) (Table 5).

TABLE 5

Specifications of human neuroblastoma and peripheral nerve tissue array

| Position | Sex | Age | Pathology | Grade | TNM | Type |
|---|---|---|---|---|---|---|
| A1 | F | 3 | Neuroblastoma (fibrofatty tissue) | 3 | T4N0M0 | Malignant |
| A2 | F | 8 | Neuroblastoma | 2 | T1N0M0 | Malignant |
| A3 | F | 1 | Neuroblastoma | 3 | T3N0M0 | Malignant |
| A4 | M | 18 | Neuroblastoma | 3 | T2N1M0 | Malignant |
| B1 | M | 27 | Neuroblastoma | 3 | T1N0M0 | Malignant |
| B2 | M | 7 | Neuroblastoma | 2 | T1N0M0 | Malignant |
| B3 | F | 4 | Neuroblastoma | 2 | T3N0M0 | Malignant |
| B4 | M | 6 | Neuroblastoma | 3 | T4N0M0 | Malignant |
| C1 | F | 26 | Neuroblastoma | 2 | T1N0M0 | Malignant |
| C2 | F | 3 | Neuroblastoma | 3 | T3N0M0 | Malignant |
| C3 | F | 4 | Neuroblastoma | 3 | T3N1M0 | Malignant |
| C4 | F | 1 | Neuroblastoma | 3 | T3N0M0 | Malignant |
| D1 | M | 84 | Neuroblastoma | 3 | T3N1M0 | Malignant |
| D2 | F | 2 | Neuroblastoma | 2 | T3N0M0 | Malignant |
| D3 | M | 5 | Neuroblastoma | 1 | T2N0M0 | Malignant |
| D4 | M | 5 | Neuroblastoma | 2 | T2N1M0 | Malignant |
| E1 | M | 8 Mon. | Neuroblastoma | 2 | T2N0M0 | Malignant |
| E2 | M | 1 | Neuroblastoma | 3 | T2N0M0 | Malignant |
| E3 | F | 39 | Neuroblastoma | 1 | T3N0M0 | Malignant |
| E4 | F | 14 Mon. | Neuroblastoma | 3 | T2N0M0 | Malignant |
| F1 | F | 2 | Neuroblastoma | 2 | T1N0M0 | Malignant |
| F2 | M | 51 | Neuroblastoma | 1 | T2N0M0 | Malignant |
| F3 | F | 25 | Neuroblastoma | 2 | T3N0M0 | Malignant |

TABLE 5-continued

Specifications of human neuroblastoma and peripheral nerve tissue array

| Position | Sex | Age | Pathology | Grade | TNM | Type |
|---|---|---|---|---|---|---|
| F4 | M | 6 | Neuroblastoma | 2 | T3N0M0 | Malignant |
| G1 | M | 20 | Neuroblastoma | 3 | T2N0M0 | Malignant |
| G2 | M | 31 | Normal peripheral nerve tissue | | | Normal |
| G3 | M | 36 | Normal peripheral nerve tissue | | | Normal |
| G4 | M | 33 | Normal peripheral nerve tissue | | | Normal |

In order to further analyze GPC2 expression in normal human tissues, a FDA-recommended human normal tissue array was used and probed with the LH7 antibody. No significant GPC2 staining was observed in the normal tissues including essential organs such as the brain, heart, lung, and kidney. These results suggest a tumor specific expression of GPC2. The complete panel of all 32 types of normal tissues stained for GPC2 expression is summarized in Table 6.

TABLE 6

Specifications of human normal tissue array

| Position | Sex | Age | Pathology | Type |
|---|---|---|---|---|
| A1 | F | 24 | Cerebrum gray matter tissue | Normal |
| A2 | M | 49 | Cerebrum white matter tissue | Normal |
| A3 | M | 35 | Cerebellum tissue | Normal |
| A4 | F | 2 | Adrenal gland tissue | Normal |
| B1 | F | 46 | Adjacent normal ovary tissue | NAT |
| B2 | F | 35 | Pancreas tissue | Normal |
| B3 | M | 16 | Thyroid gland tissue | Normal |
| B4 | M | 34 | Adenohypophysis tissue | Normal |
| C1 | M | 28 | Testis tissue (cataplasia) | Normal |
| C2 | F | 44 | Thyroid gland tissue | Normal |
| C3 | F | 44 | Adjacent normal breast tissue | NAT |
| C4 | F | 21 | Spleen tissue | Normal |
| D1 | F | 16 | Tonsil tissue | Normal |
| D2 | M | 42 | Thymus gland tissue | Normal |
| D3 | F | 21 | Bone marrow tissue | Normal |
| D4 | M | 48 | Lung tissue | Normal |
| E1 | M | 35 | Cardiac muscle tissue | Normal |
| E2 | F | 42 | Esophagus tissue | Normal |
| E3 | M | 38 | Stomach tissue | Normal |
| E4 | M | 40 | Small intestine tissue | Normal |
| F1 | M | 61 | Adjacent normal colon tissue | NAT |
| F2 | M | 38 | Liver tissue | Normal |
| F3 | M | 30 | Salivary gland tissue | Normal |
| F4 | F | 21 | Kidney tissue | Normal |
| G1 | M | 43 | Prostate tissue | Normal |
| G2 | F | 41 | Adjacent normal endometrium tissue | Normal |
| G3 | F | 45 | Adjacent normal cervix tissue | NAT |
| G4 | M | 50 | Skeletal muscle tissue | Normal |
| H1 | M | 2 mon. | Skin tissue | Normal |
| H2 | M | 36 | Peripheral nerve tissue | Normal |
| H3 | M | 19 | Mesothelial tissue | Normal |
| H4 | F | 21 | Ciliary body tissue | Normal |

Figure 7:
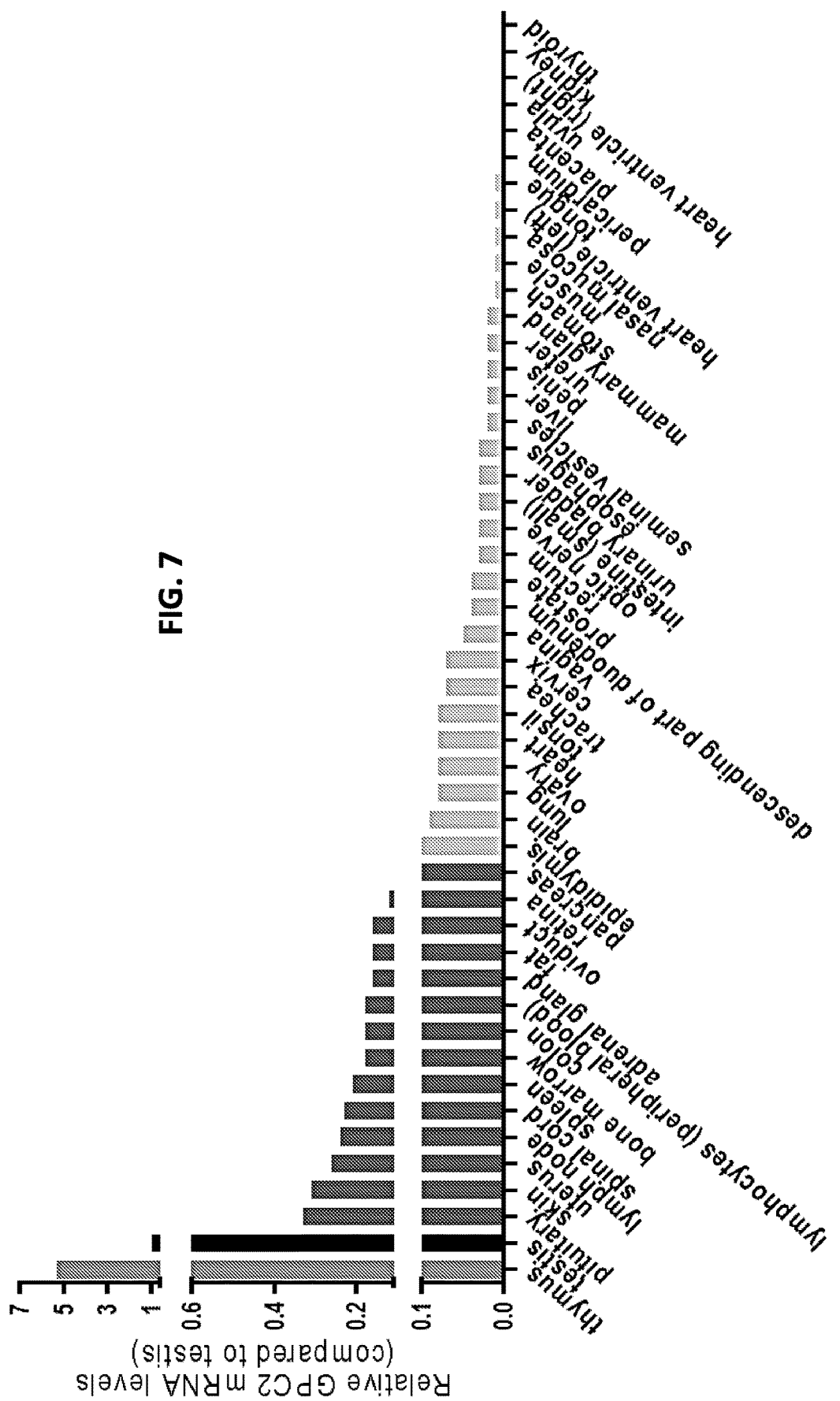
FIG. 7: GPC2 mRNA expression in human normal tissues. The GPC2 mRNA expression was measured by quantitative real-time PCR. The relative GPC2 levels in different normal tissues were compared to GPC2 expression in testis.

GPC2 mRNA levels were also measured in a human normal tissue array by quantitative real-time PCR. GPC2 mRNA expression was not found in any normal tissues except for a moderate mRNA expression in thymus and testis (FIG. 7). However, our immunohistochemistry analysis showed no specific binding of the LH7 antibody for either testis (C1) or thymus (D2) in our immunohistochemistry (FIG. 7). These data strongly support tumor specific expression of GPC2 and suggest it as a promising neuroblastoma biomarker.

Figure 2B:
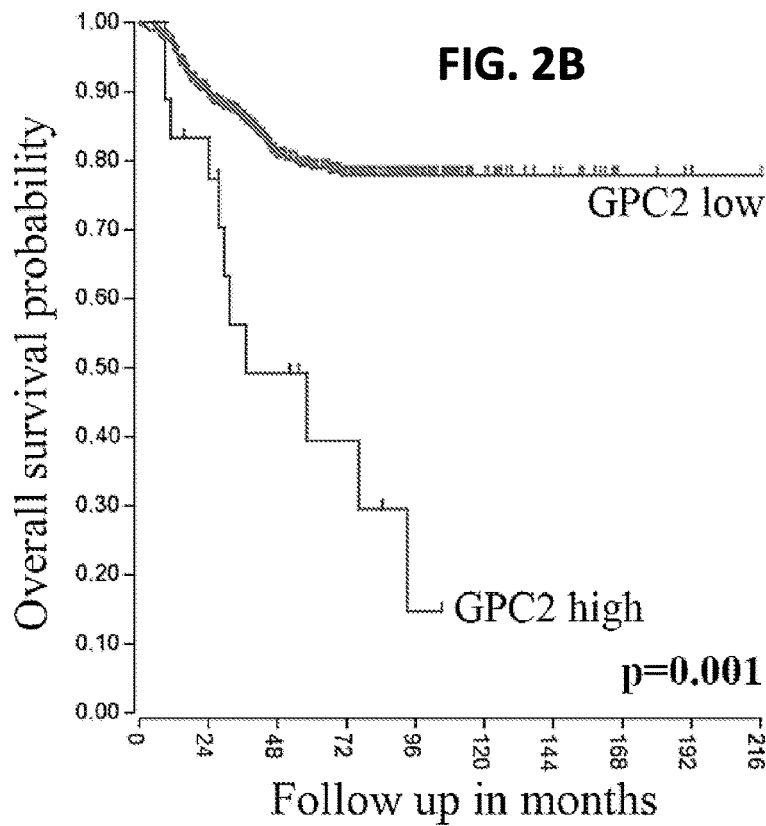
Figure 2C:
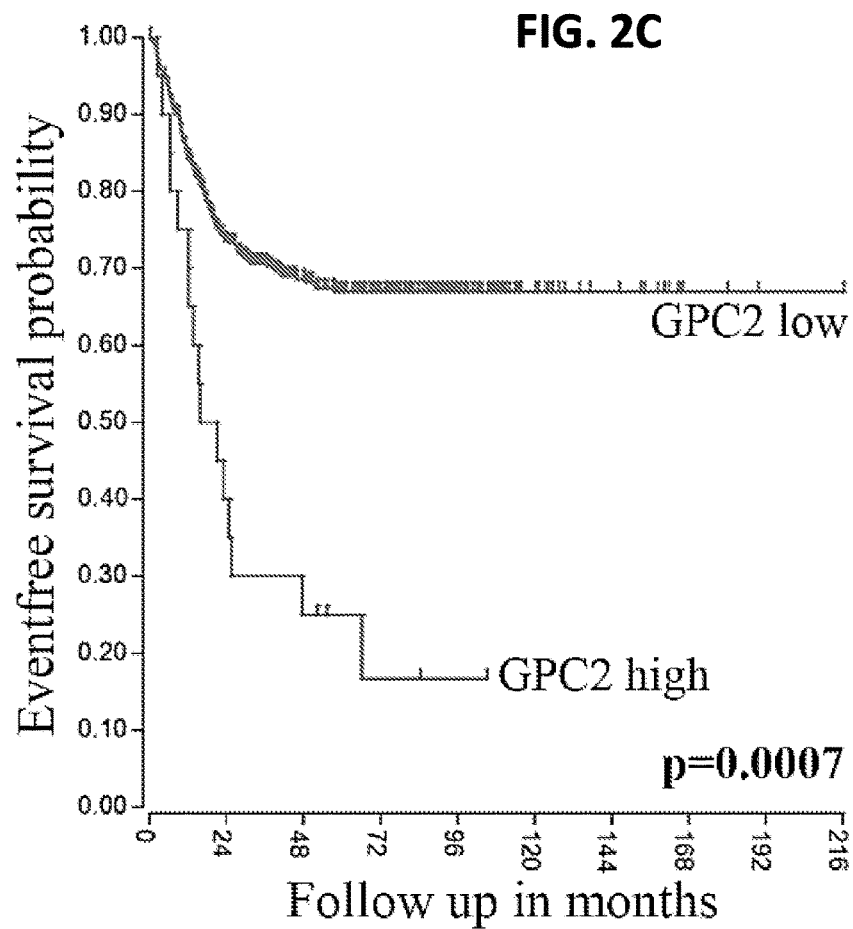

There has been evidence that GPC3 expression or other glypicans (e.g. GPC1) have been correlated with poor prognosis in hepatocellular carcinoma or other types of cancer (Hara et al., Br J Cancer 115(1):66-75, 2016; Herreros-Villanueva and Bujanda, Ann Transl Med 4(4):64, 2016; Shirakawa et al., Cancer Sci 100(8):1403-1407, 2009). To analyze a possible correlation between GPC2 mRNA levels and survival of neuroblastoma patients, the R2 Genomics Analysis Platform was utilized. Patients with high GPC2 expression exhibited poorer overall survival and event-free survival when compared to patients with low GPC2 expression (FIGS. 2B and 2C).

Figure 8A:
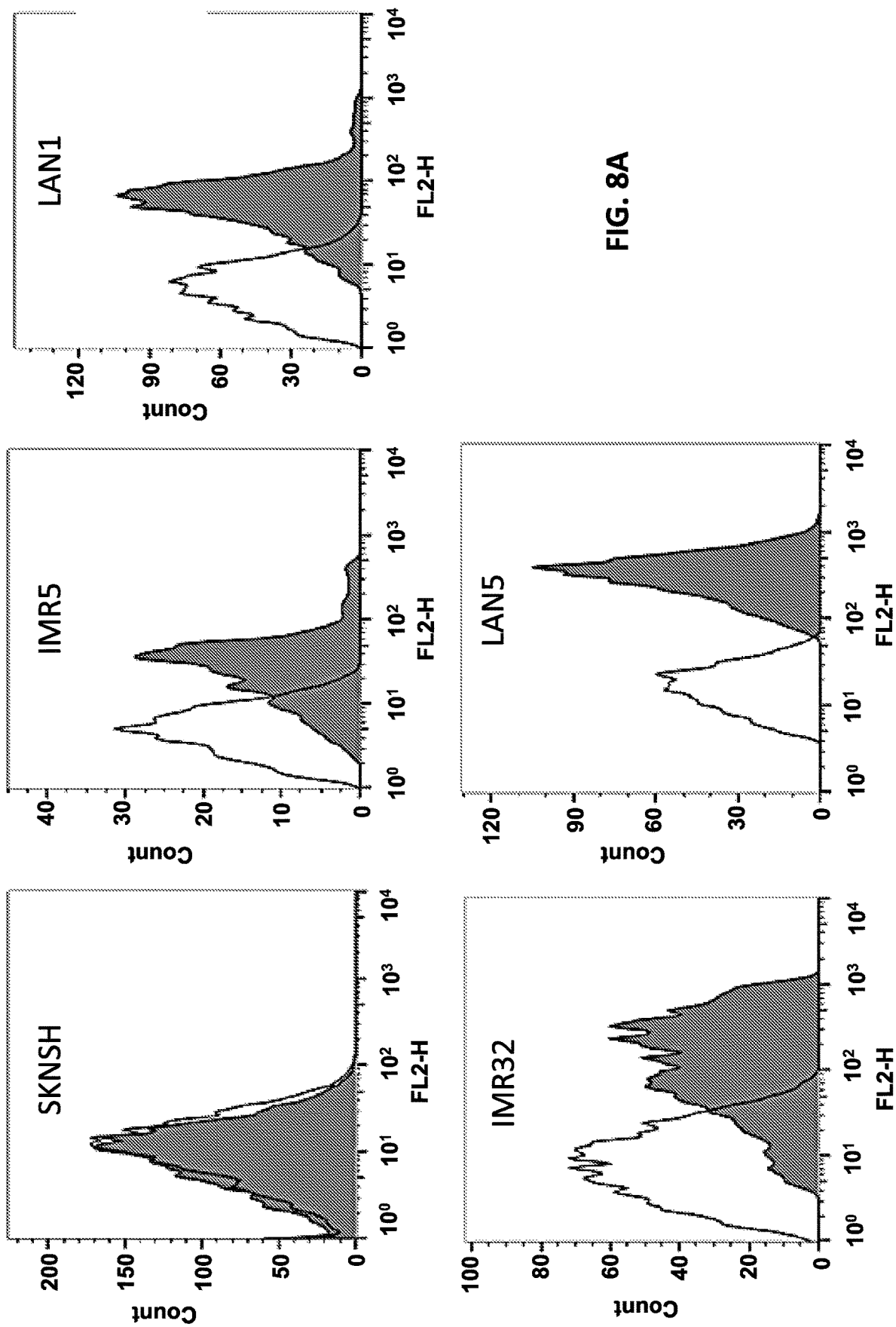
FIGS. 8A-8B: Cell surface GPC2 expression in human neuroblastoma cells.
Figure 8B:
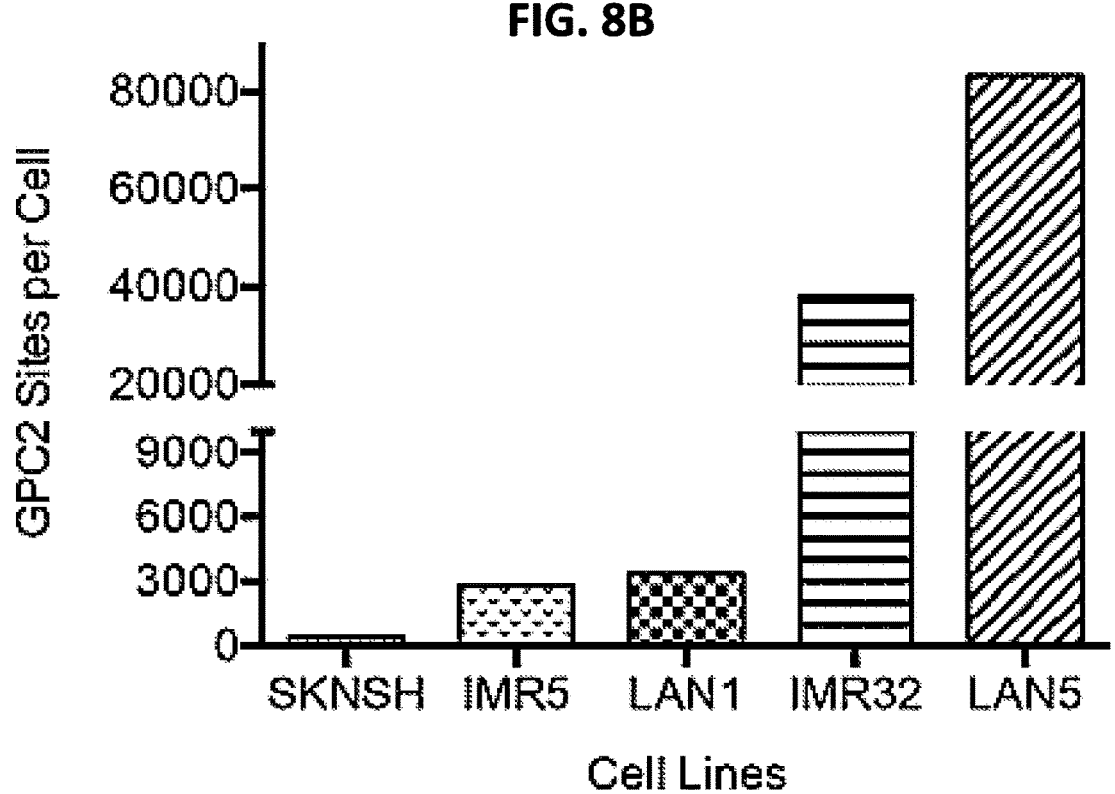

The ability of the LH7 antibody to bind GPC2 on neuroblastoma cells was analyzed by flow cytometry. LH7 showed specific binding to IMR5, LAN1, IMR32 and LAN5 neuroblastoma cells (FIG. 8A). In addition, LH7 exhibited no binding to SKNSH cells, which is consistent with the low expression of GPC2 in this neuroblastoma cell line (FIG. 2A). Furthermore, the number of cell surface GPC2 sites per cell was quantified using flow cytometry. LAN5 and IMR32 cells expressing native GPC2 contain between $10^4$ and $10^5$ sites per cell, while LAN1 and IMR5 cells contain between $10^3$ and $10^4$ GPC2 sites per cell (FIG. 8B). SKNSH cells showed an extremely low number of cell surface GPC2 sites, with only 433 sites per cell. Taken together, these data have demonstrated that GPC2 is a tumor-specific cell surface antigen in neuroblastoma.

Figure 3A:
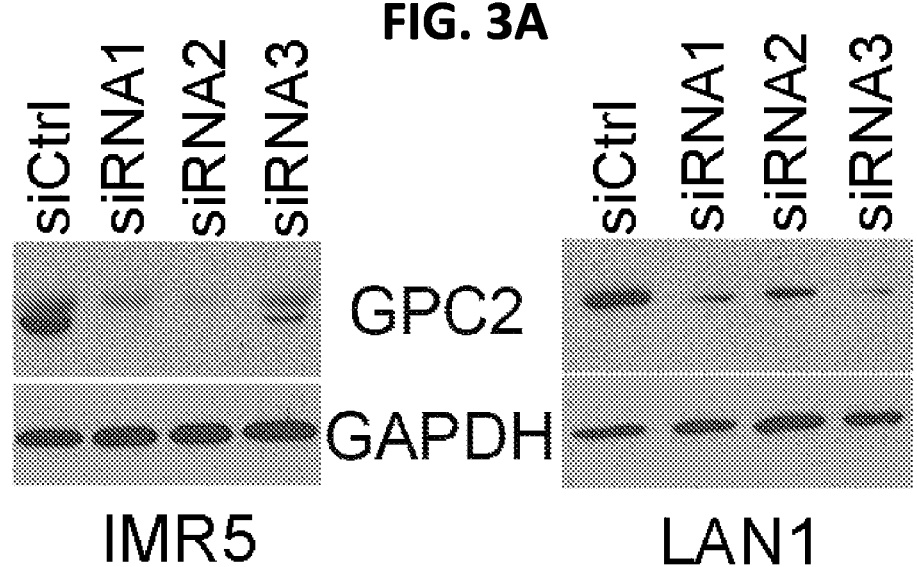
FIGS. 3A-3L: Genetic silencing of GPC2 inhibits neuroblastoma tumor cell growth and induces apoptosis by suppressing Wnt/β-catenin signaling.
Figure 3B:
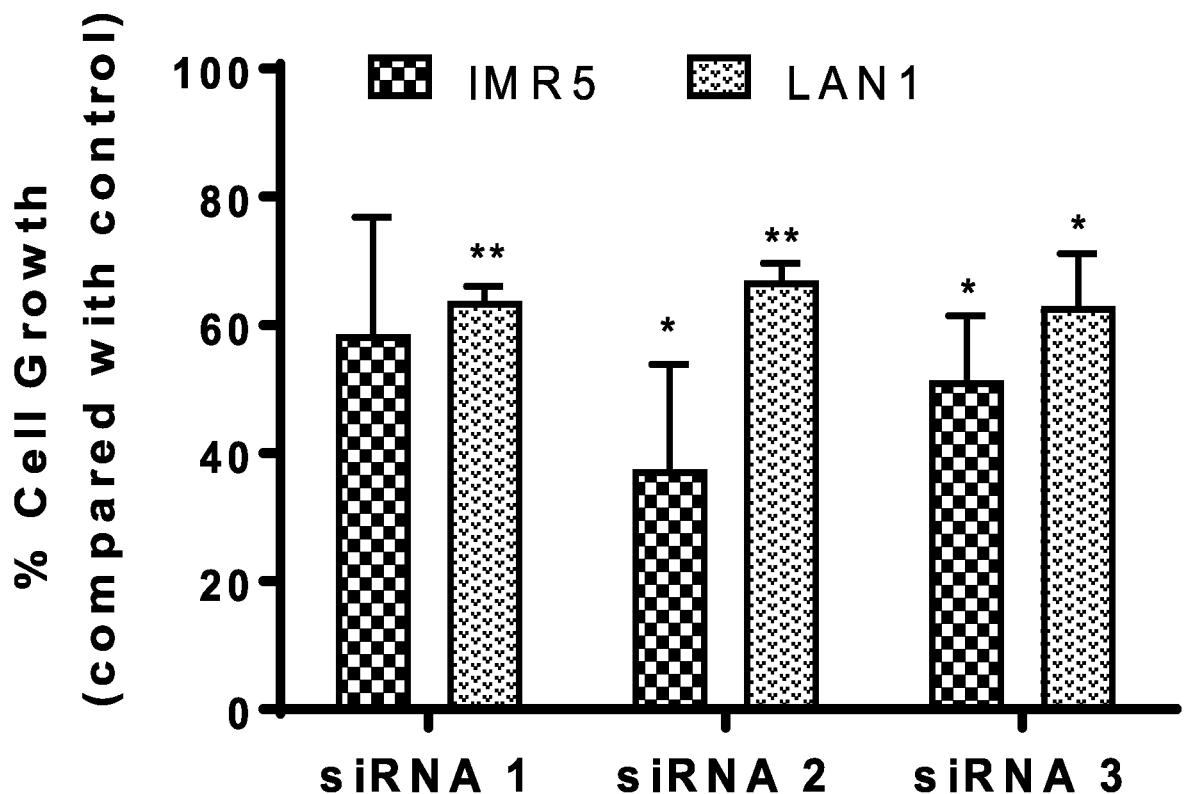
Figure 3C:
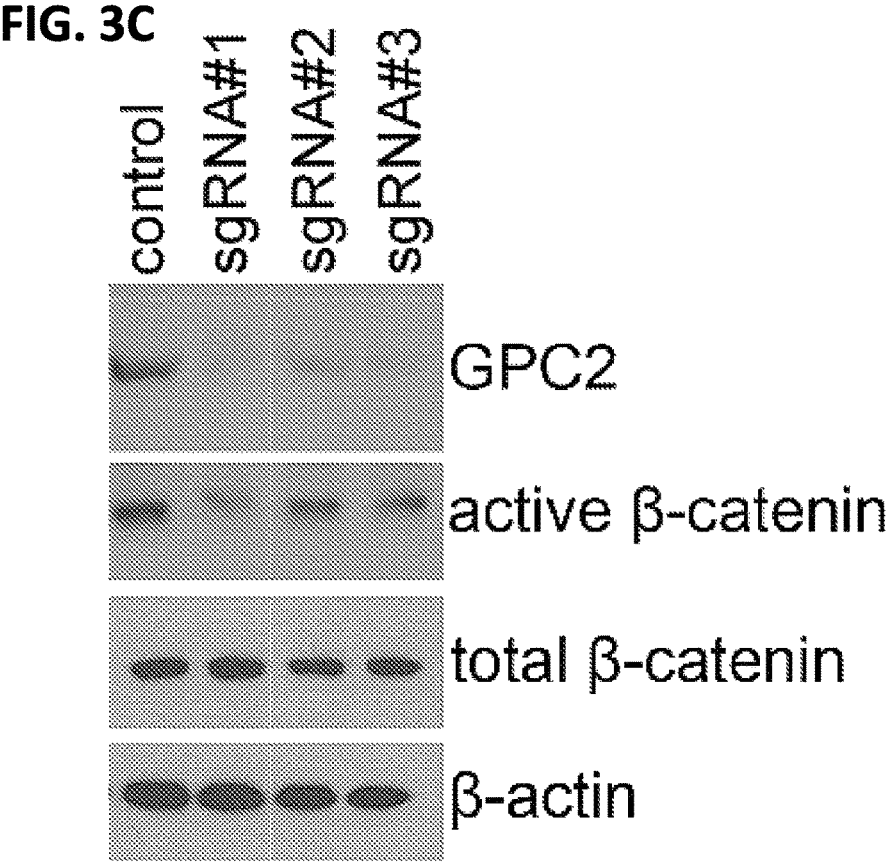
Figure 3D:
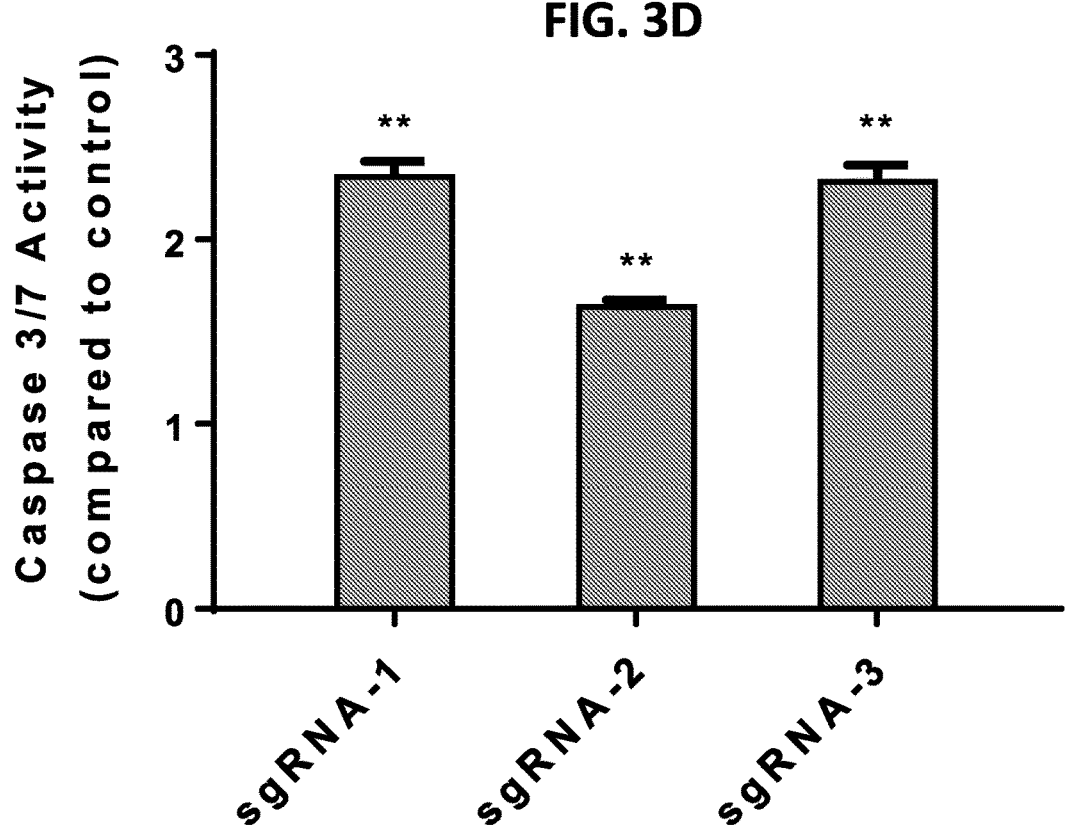
Figure 9A:
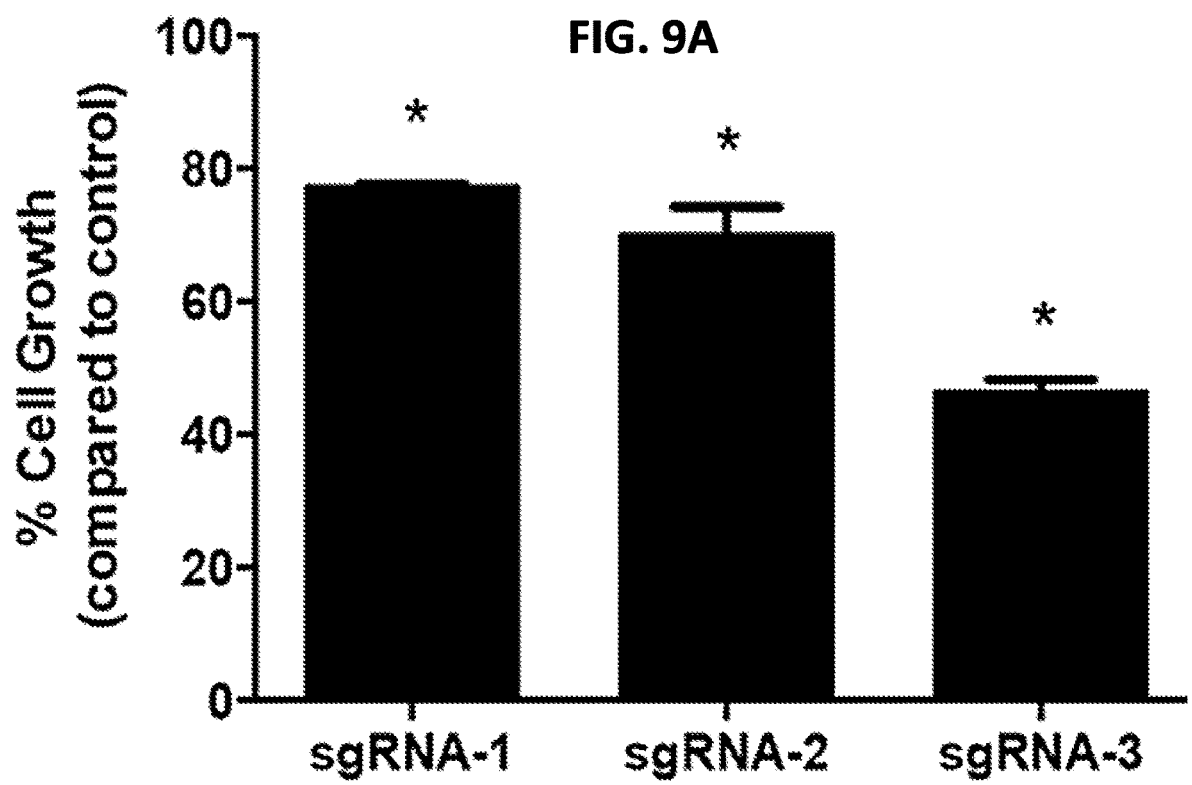
FIGS. 9A-9B: Knockout of GPC2 exhibits antitumor activity in neuroblastoma cells.
Figure 9B:
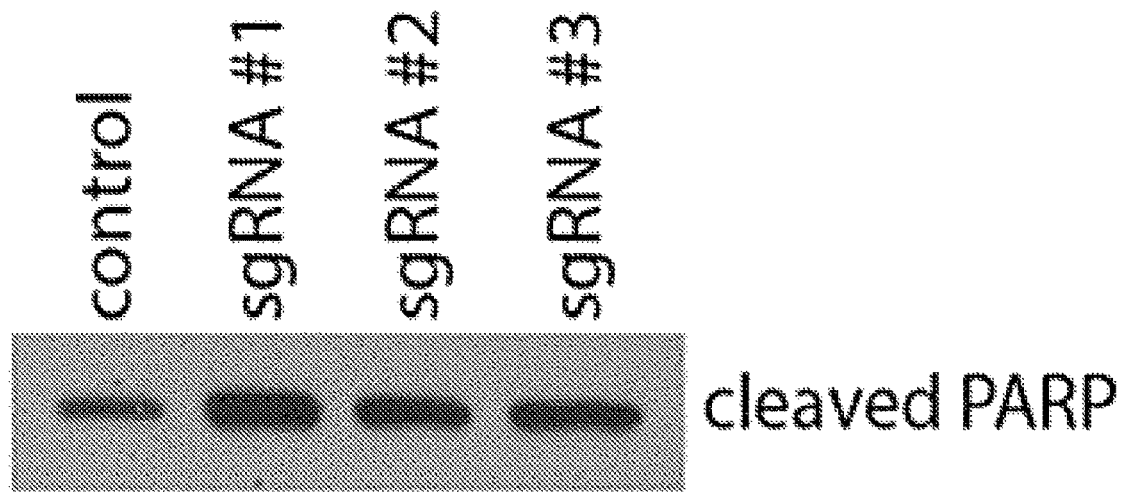

Silencing of GPC2 Inhibits Neuroblastoma Cell Growth Via Suppression of Wnt/β-Catenin Signaling To analyze the role of GPC2 in neuroblastoma cell growth, siRNA and CRISPR-Cas9 techniques were used to silence GPC2 in two neuroblastoma cell models (IMR5 and LAN1). Three different GPC2 siRNAs were used to avoid potential off-target effects of siRNA. GPC2 knockdown efficiency was confirmed by western blotting, which showed substantial reductions of GPC2 levels in both cell lines (FIG. 3A). As shown in FIG. 3B, GPC2 siRNAs suppressed the growth of neuroblastoma cells within three days of transfection by approximately 40-50% when compared to cells transfected with scrambled siRNA. To validate the oncogenic effect of GPC2 in neuroblastoma, GPC2 knockout neuroblastoma cells were generated by using CRISPR-Cas9. Three single guide RNAs (sgRNAs) targeting different GPC2 exons (exons 1, 2, and 3) were transfected into IMR5 cells. Expression of GPC2 protein was almost completely abolished in the sgRNA-transfected cells (FIG. 3C). As shown in FIG. 9A, a 25-50% reduction of growth was observed in GPC2 knockout cells compared with vector control cells after 3 days of growth. In addition, knockout of GPC2 induced apoptosis in neuroblastoma cells as measured by elevated expression of cleaved-Poly (ADP-ribose) polymerase (PARP) (FIG. 9B) and increased activity of caspase-3 and 7 (FIG. 3D).

Figure 3E:
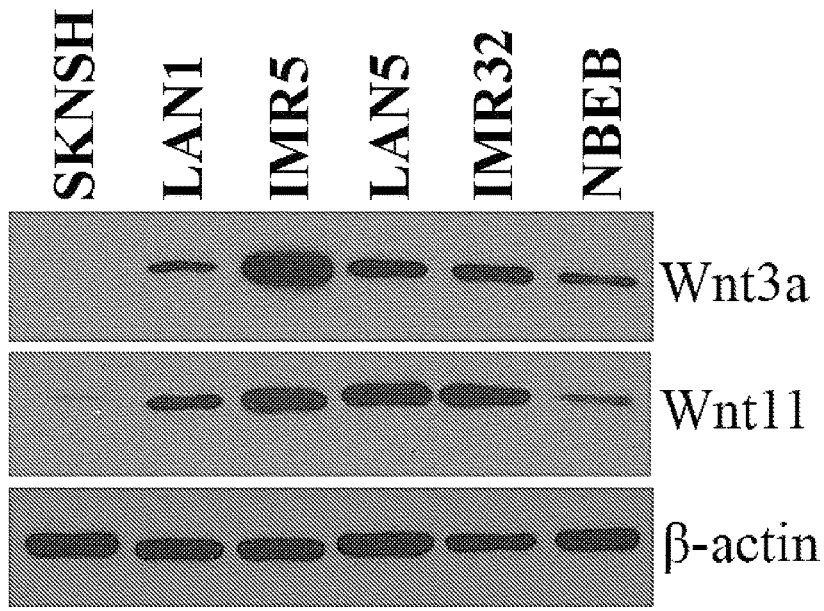
Figure 3G:
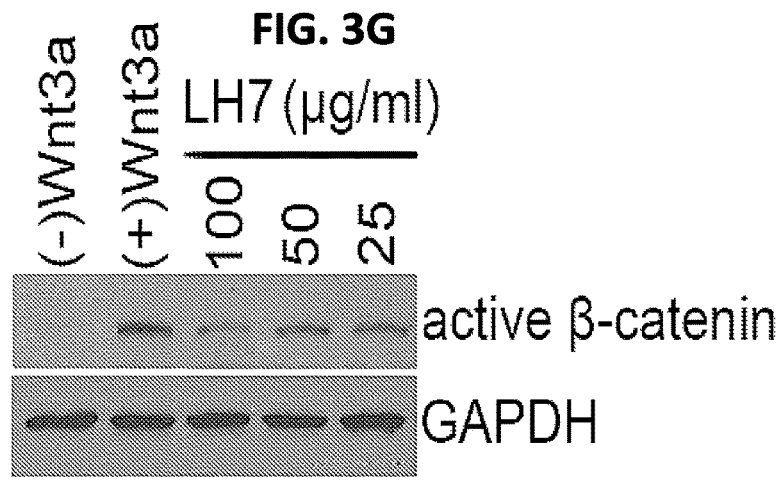
Figure 3F:
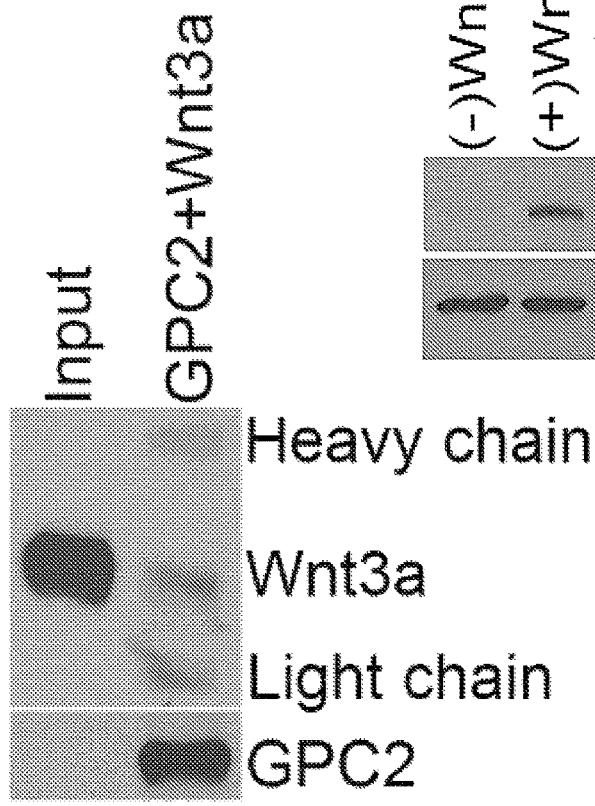
Figure 3H:
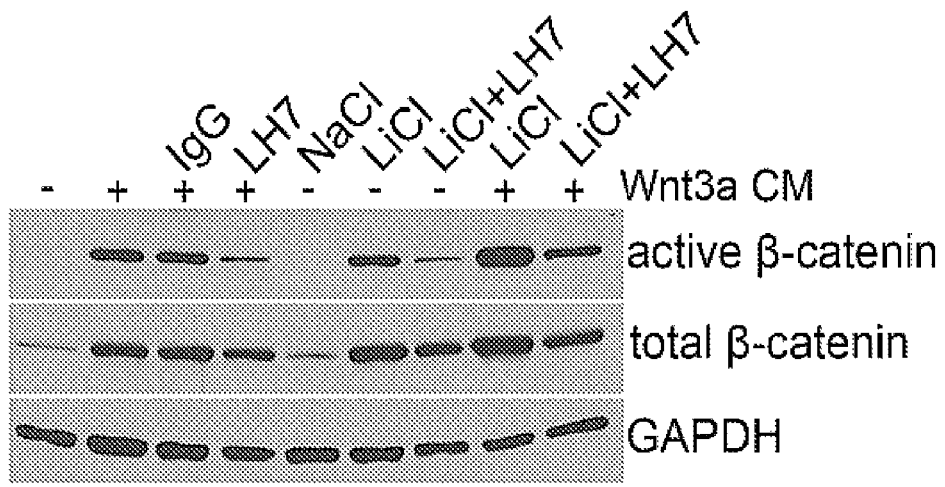
Figure 3I:
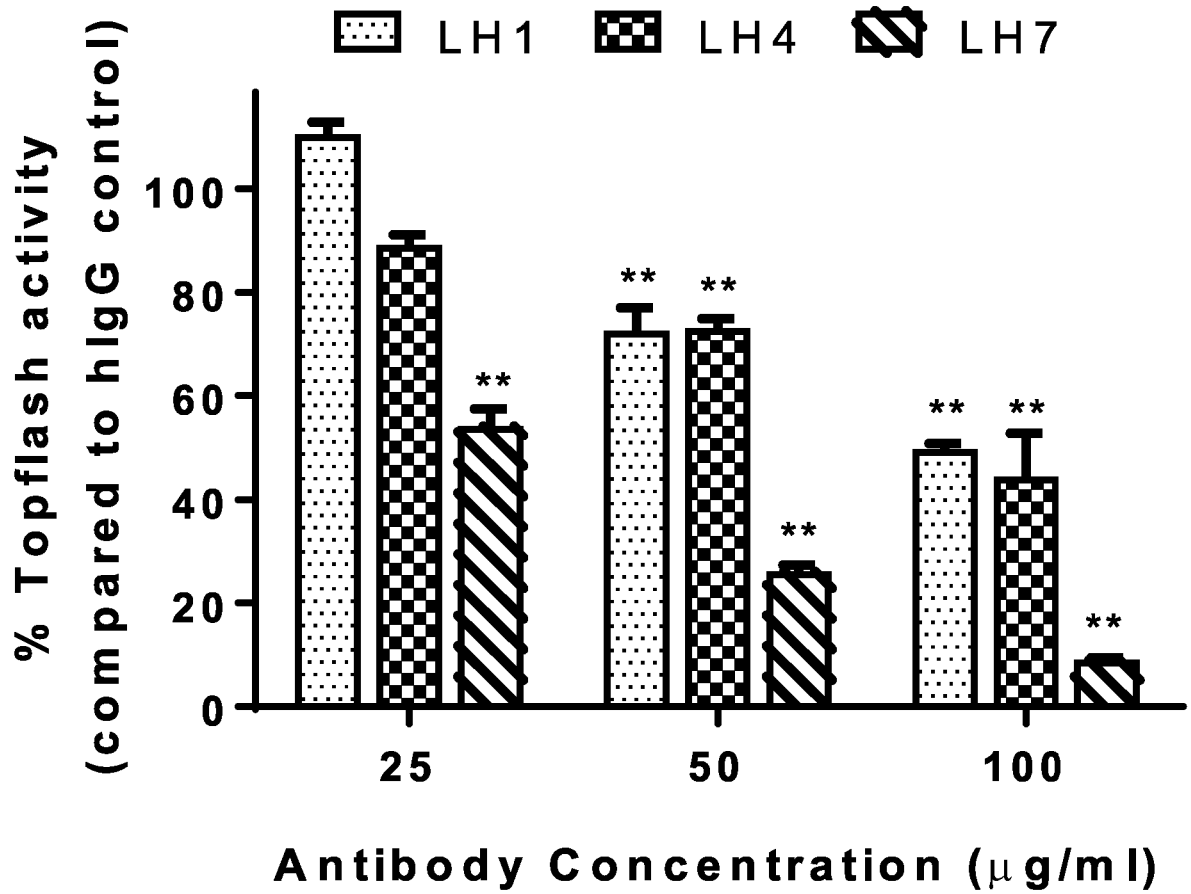
Figure 10:
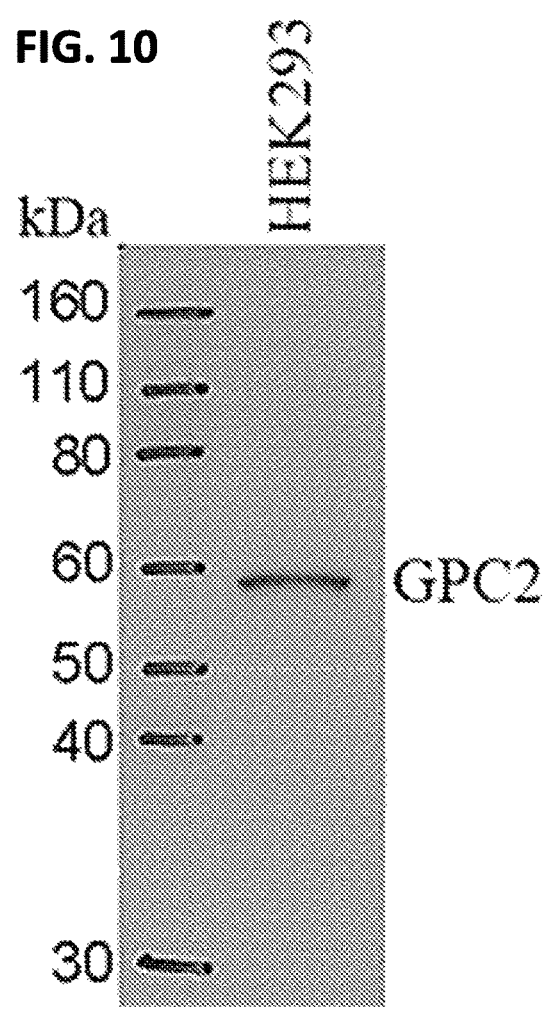
FIG. 10: GPC2 expression in HEK293 Supertopflash cells.

It was hypothesized that GPC2 could be an extracellular modulator of Wnt signaling in neuroblastoma cells. GPC3 has been shown to interact with Wnt and suppress hepatocellular carcinoma cell proliferation (Gao et al., *Hepatology* 60(2):576-587, 2014). To determine if GPC2 could affect Wnt signaling in neuroblastoma cells, active-β-catenin levels were measured. As shown in FIG. 3C, the expression of active-β-catenin was lower in GPC2 knockout IMR5 cells than vector control cells. Expression of Wnt3a and Wnt11 was detected in all the neuroblastoma cell lines expressing high levels of GPC2 (LAN1, IMR5, LAN5, IMR32 and NBEB). However, Wnt3a was undetectable and Wnt11 expression was extremely low in the SKNSH cell line that has low GPC2 expression (FIG. 3E). To determine the interaction of GPC2 and Wnt, a co-immunoprecipitation assay was conducted using Wnt3a-conditioned media (CM) and it was demonstrated that GPC2 could interact with Wnt3a (FIG. 3F). Furthermore, the luciferase-expressing HEK-293 Supertopflash cell model was used to analyze the function of GPC2. As shown in FIG. 10, GPC2 was expressed in HEK-293 cells. Treating cells with the LH7 single domain antibody decreased the Wnt3a-induced active β-catenin levels in a dose-dependent manner (FIG. 3G). Lithium chloride (LiCl) is a GSK3β inhibitor and an intracellular β-catenin signaling inducer (Gao et al., *Hepatology* 60(2):576-587, 2014). As shown in FIG. 3H, a combination of Wnt3a and LiCl showed synergistic elevation of β-catenin expression. The elevated β-catenin expression was reduced by LH7 treatment, supporting the idea that the Wnt/β-catenin pathway can be directly modulated by the addition of the LH7 antibody. In addition to LH7, two other anti-GPC2 single domain antibodies showed dose-dependent reduction of Wnt signaling, but to a lesser degree (FIG. 3I). LH7 at 100 μg/ml resulted in a 90% reduction of β-catenin signaling as compared to control human IgG. The data indicates that the LH7 single domain antibody has the greatest inhibitory effect on Wnt signaling.

Figure 3J:
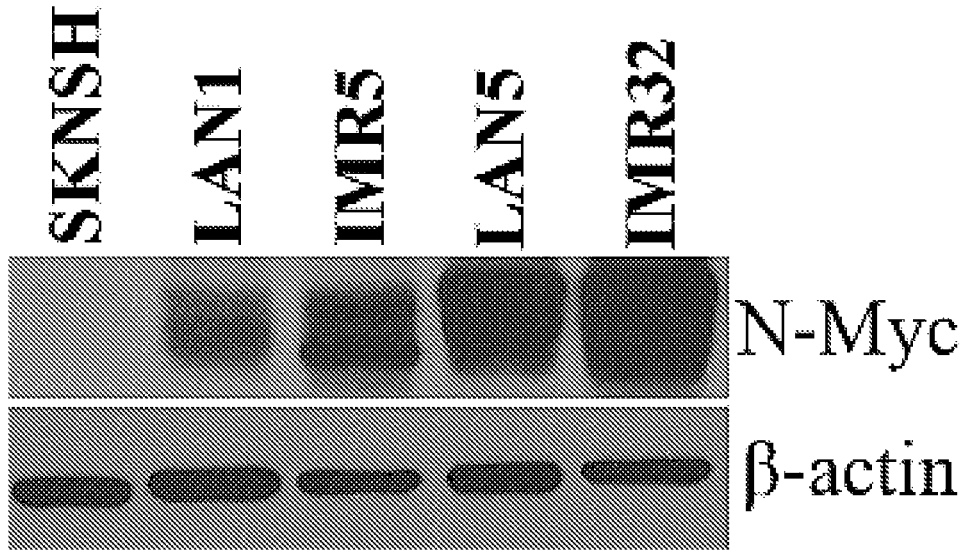
Figure 3K:
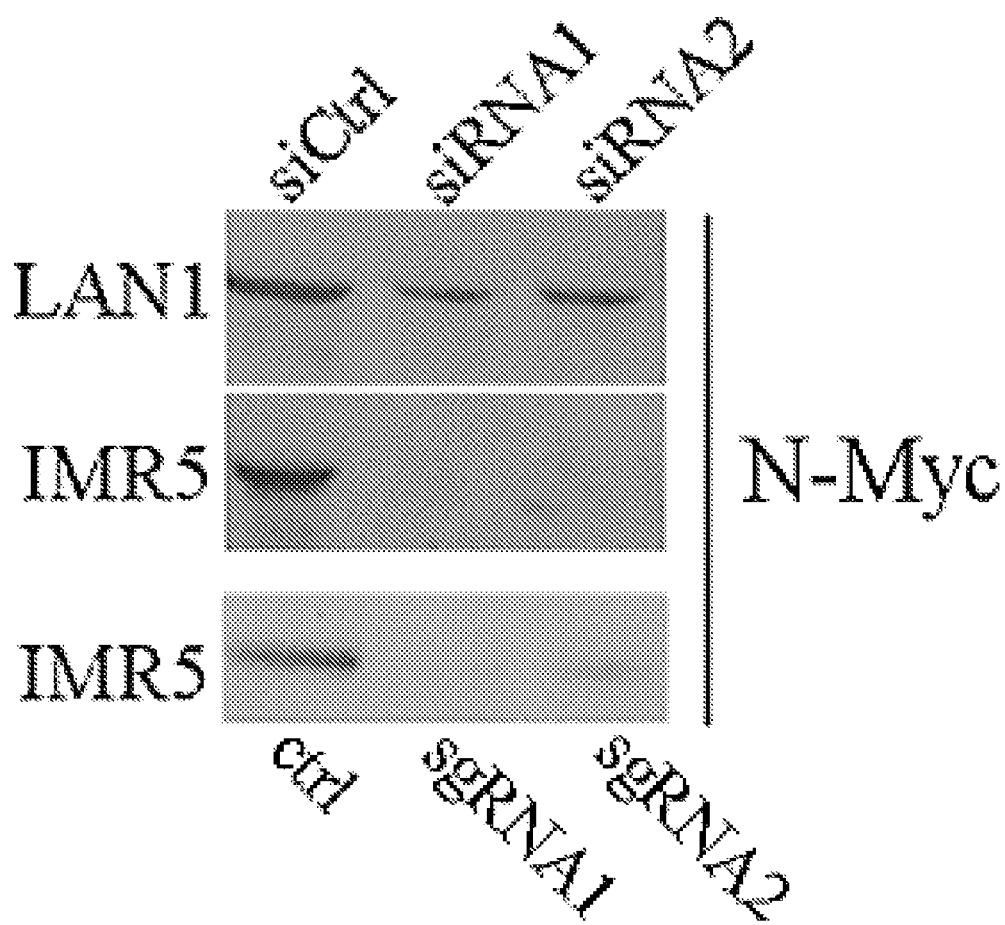
Figure 3L:
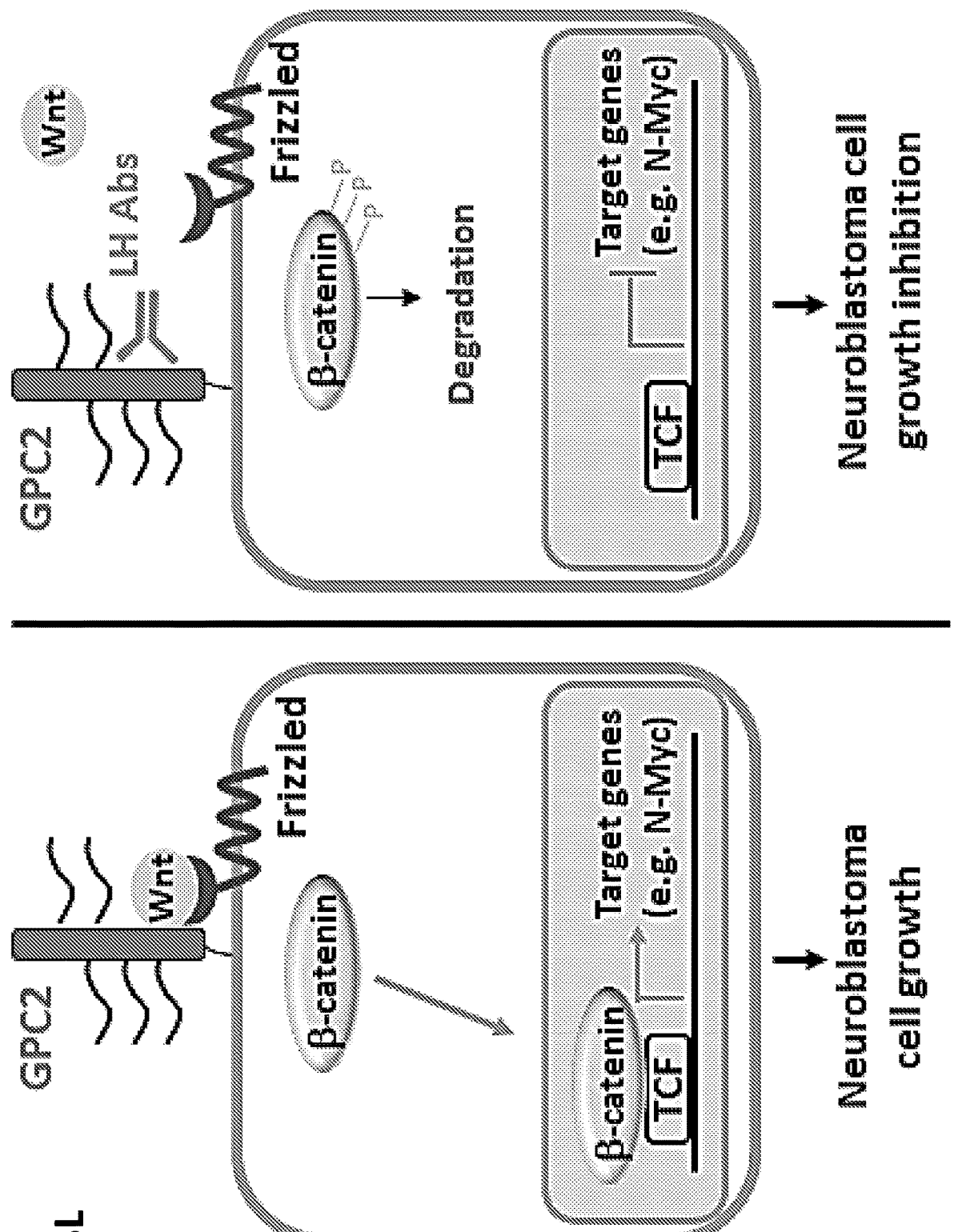

MYCN amplification occurs in approximately 25% to 33% of neuroblastoma cases, and results in N-Myc protein overexpression (Maris et al., *Lancet* 369(9579):2106-2120, 2007). Patients with MYCN-amplified tumors usually have a very poor prognosis. In addition, studies have shown that Wnt/β-catenin signaling acts upstream of N-Myc to regulate lung and limb development (Shu et al., *Dev Biol* 283(1): 226-239, 2005; ten Berge et al., *Development* 135(19):3247-3257, 2008). As shown in FIG. 3J, N-Myc protein was found in GPC2 high-expressing neuroblastoma cells (LAN1, IMR5, LAN5 and IMR32) but not in GPC2 low-expressing SKNSH cells. Furthermore, silencing of GPC2 suppressed N-Myc expression (FIG. 3K). Taken together, these data show that GPC2 is involved in Wnt signaling, and that targeting GPC2 by single domain antibodies such as LH7 can suppress neuroblastoma cell growth by inhibiting Wnt signaling and down-regulating Wnt target genes including N-Myc, an oncogenic driver of neuroblastoma pathogenesis. FIG. 3L shows a working model based on these observations.

GPC2-Specific Immunotoxins Inhibit Neuroblastoma Growth

Figure 4A:
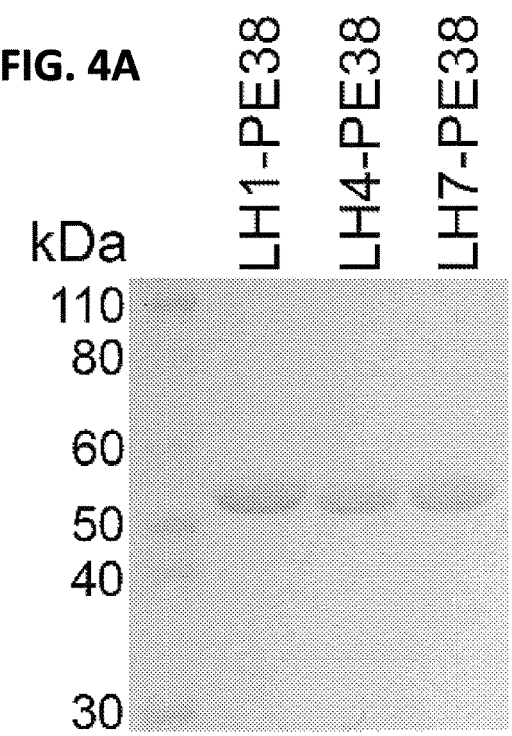
FIGS. 4A-4G: Recombinant immunotoxins against GPC2 inhibit neuroblastoma tumor growth in vitro and in vivo.
Figure 4B:
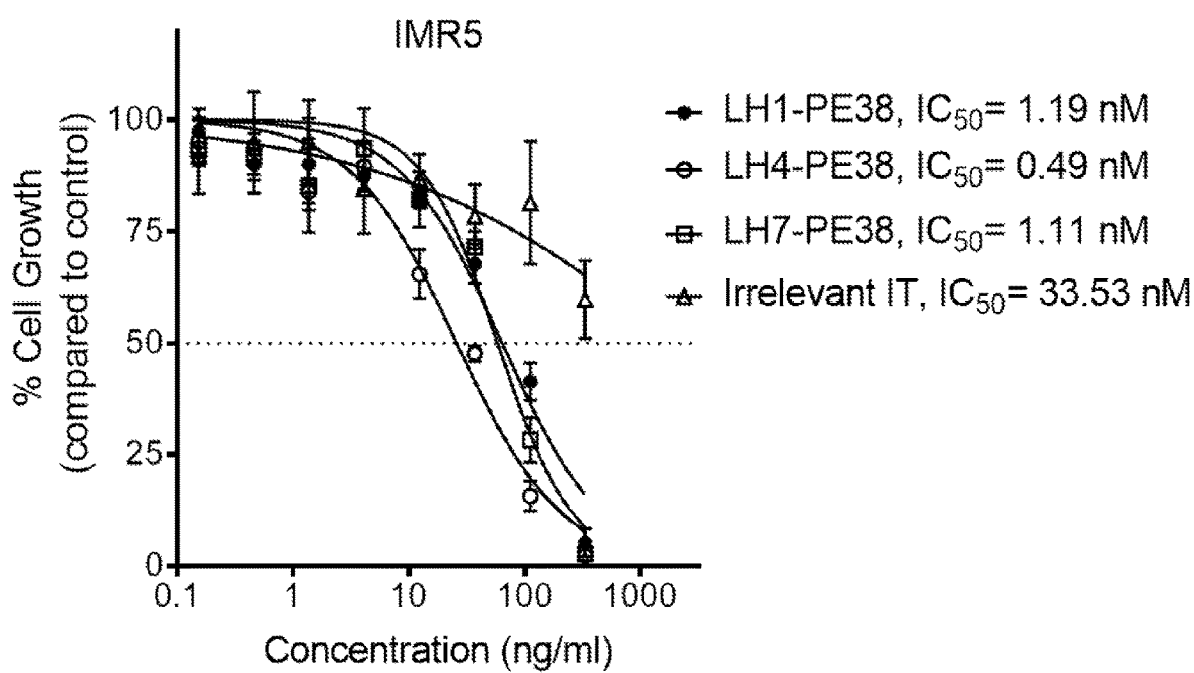
Figure 4C:
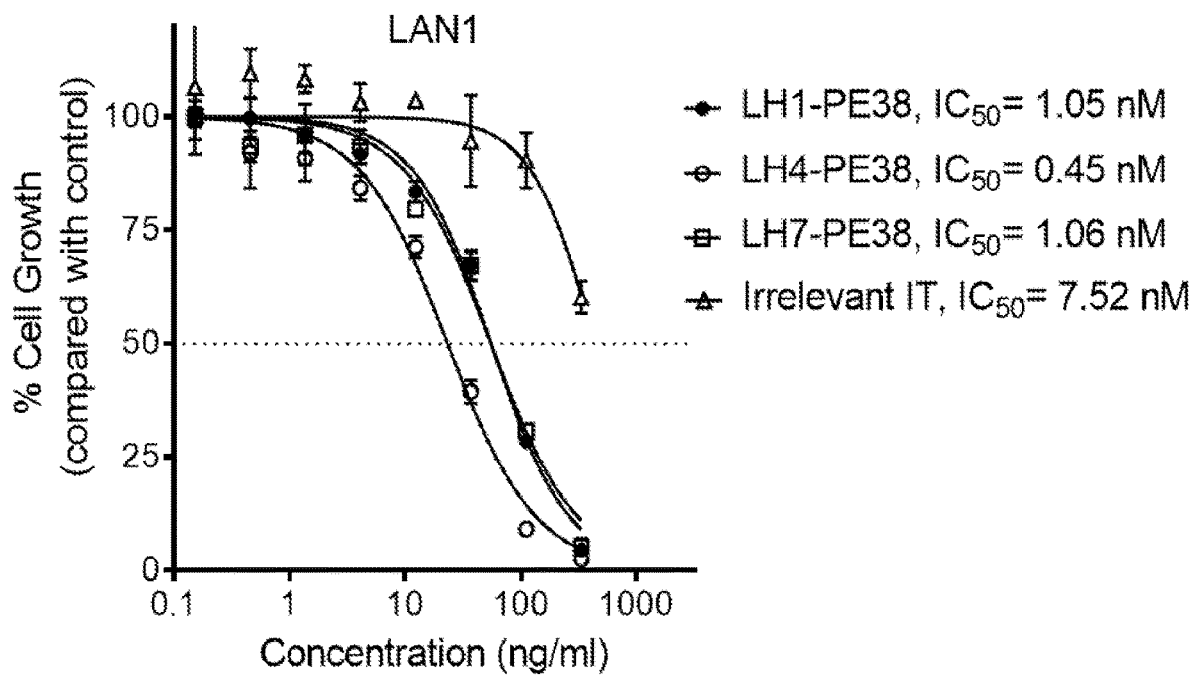
Figure 4D:
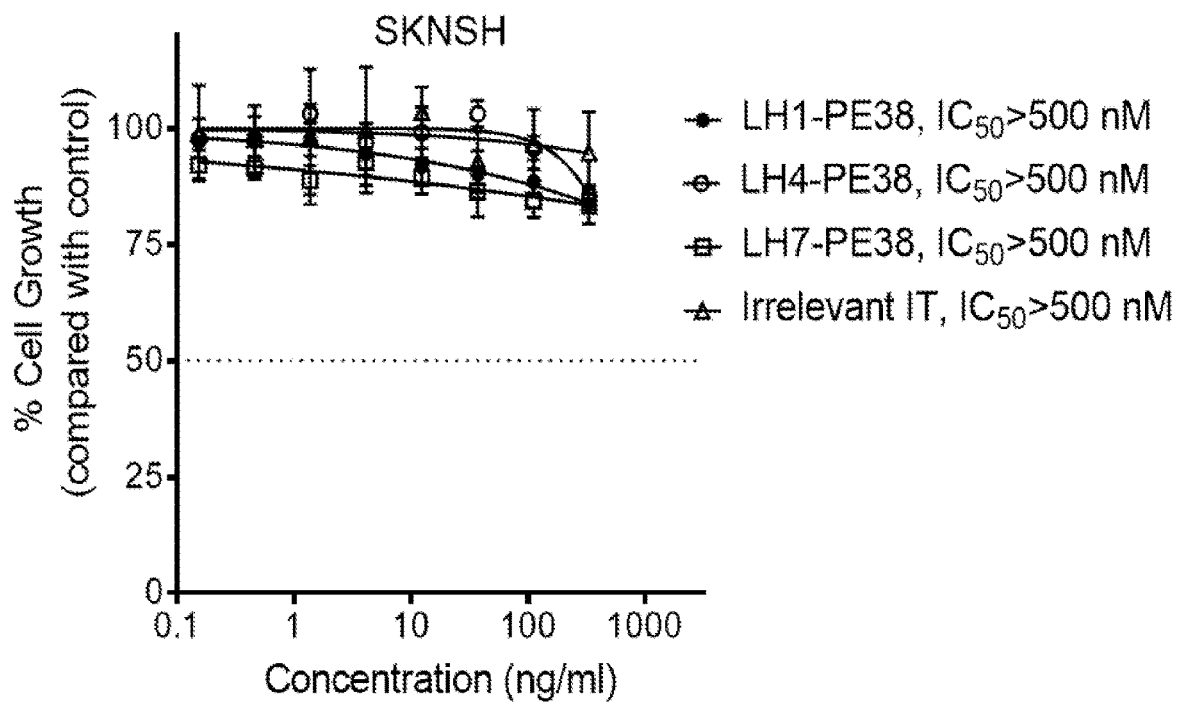
Figure 11:
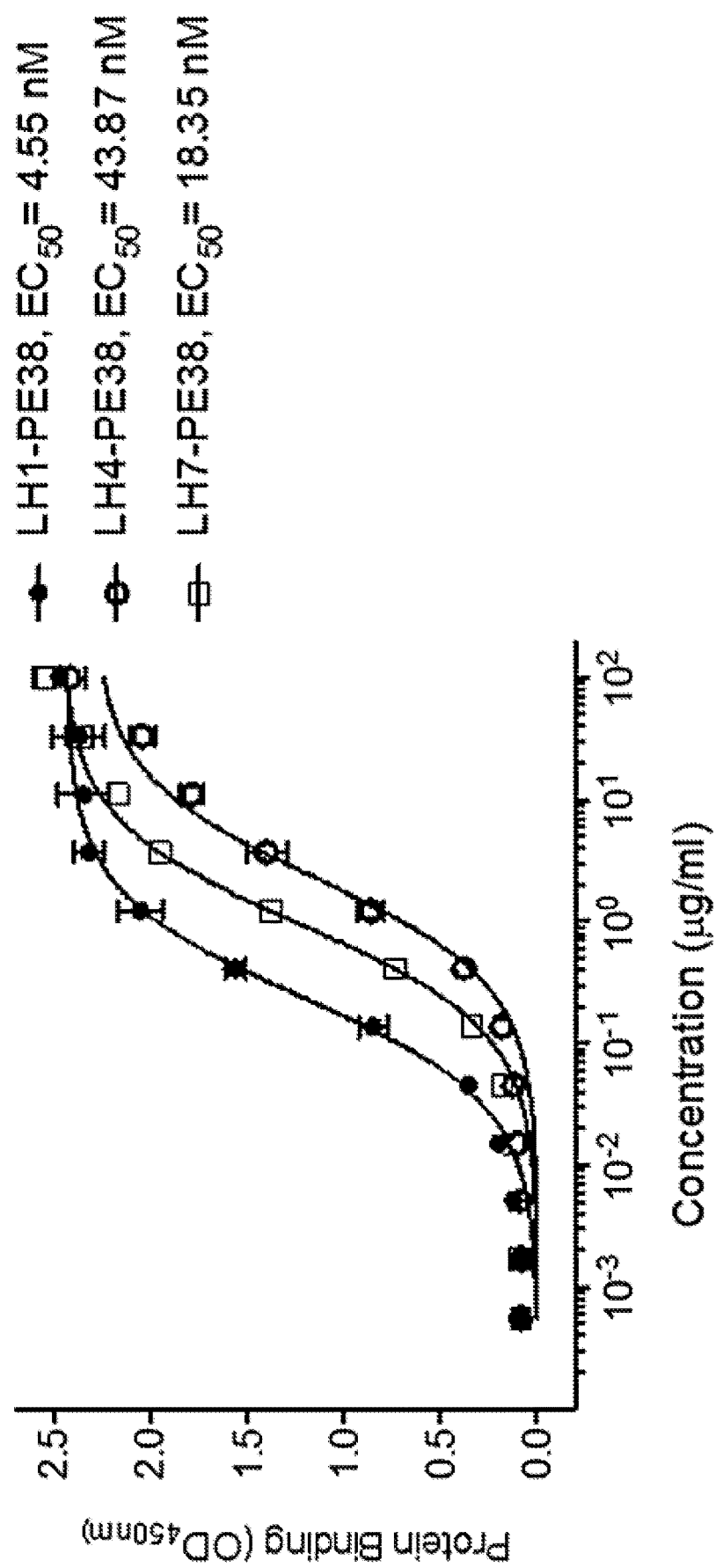
FIG. 11: ELISA analysis of the binding affinity of three anti-GPC2 immunotoxins for GPC2 protein.

To determine whether GPC2 could be used as a target of immunotoxins for the treatment of neuroblastoma, three immunotoxins were constructed using the LH1, LH4, and LH7 binding domains. All immunotoxins were expressed in *E. coli*, refolded in vitro, and isolated with over 90% purity (FIG. 4A). The binding affinities of all three immunotoxins on purified GPC2 protein was measured by ELISA. As shown in FIG. 11, the calculated $EC_{50}$ values for the three immunotoxins were in the range of 4.6 nM to 43.9 nM. The $EC_{50}$ value (18 nM) for the LH7-PE38 monomeric immunotoxin in ELISA was similar to the $K_D$ value (9.8 nM) of the LH7-Fc fusion protein (FIG. 1F), indicating the immunotoxin retained binding properties of the original single domain antibody. To determine the cytotoxicity of all immunotoxins in vitro, the inhibition of cell proliferation was examined on a panel of cell lines using the WST cell proliferation assay. All three immunotoxins potently and selectively inhibited the growth of GPC2-positive cell lines LAN1 and IMR5 with similar $IC_{50}$ values of 0.5-1.2 nM. LAN1 and IMR5 cells were poorly sensitive to an irrelevant immunotoxin targeting mesothelin ($IC_{50}$ for LAN1: 8 nM; $IC_{50}$ for IMR5: 34 nM). None of the immunotoxins affected the growth of low GPC2 expressing SKNSH cells (FIGS. 4B-4D).

Figure 4E:
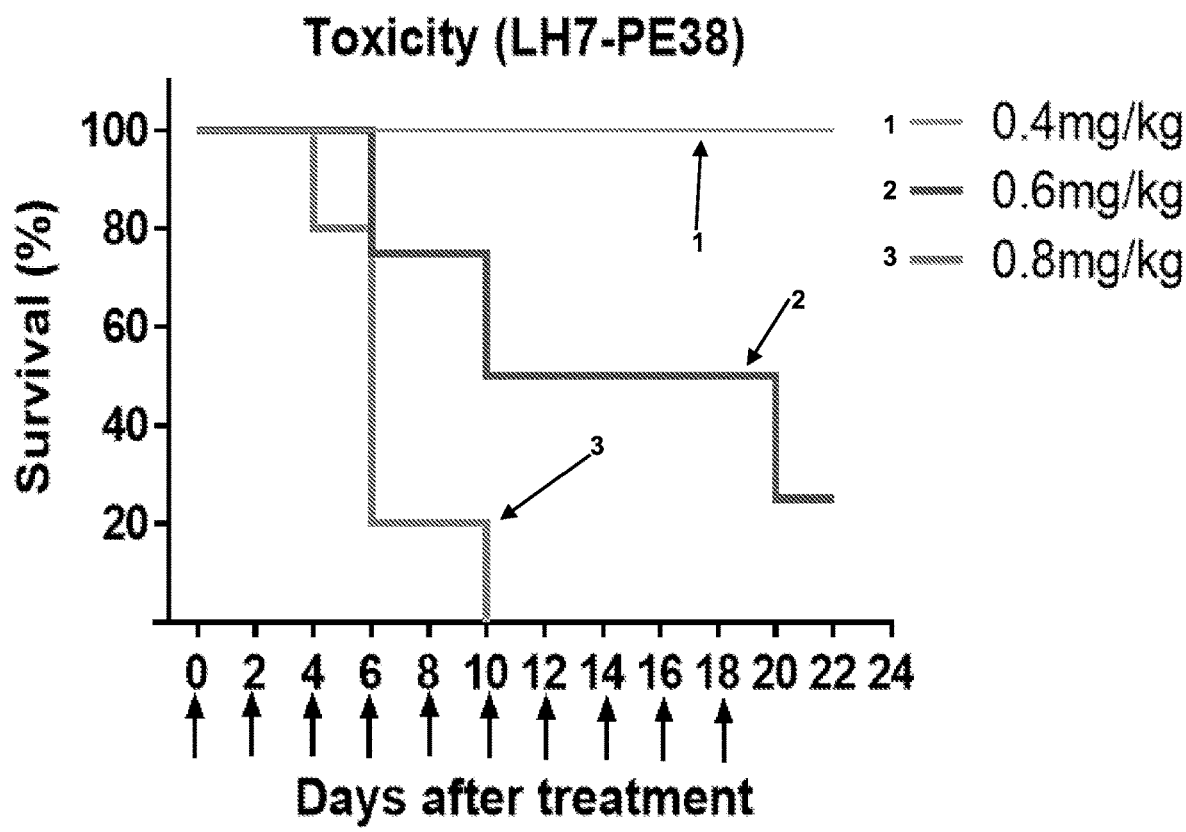
Figure 4F:
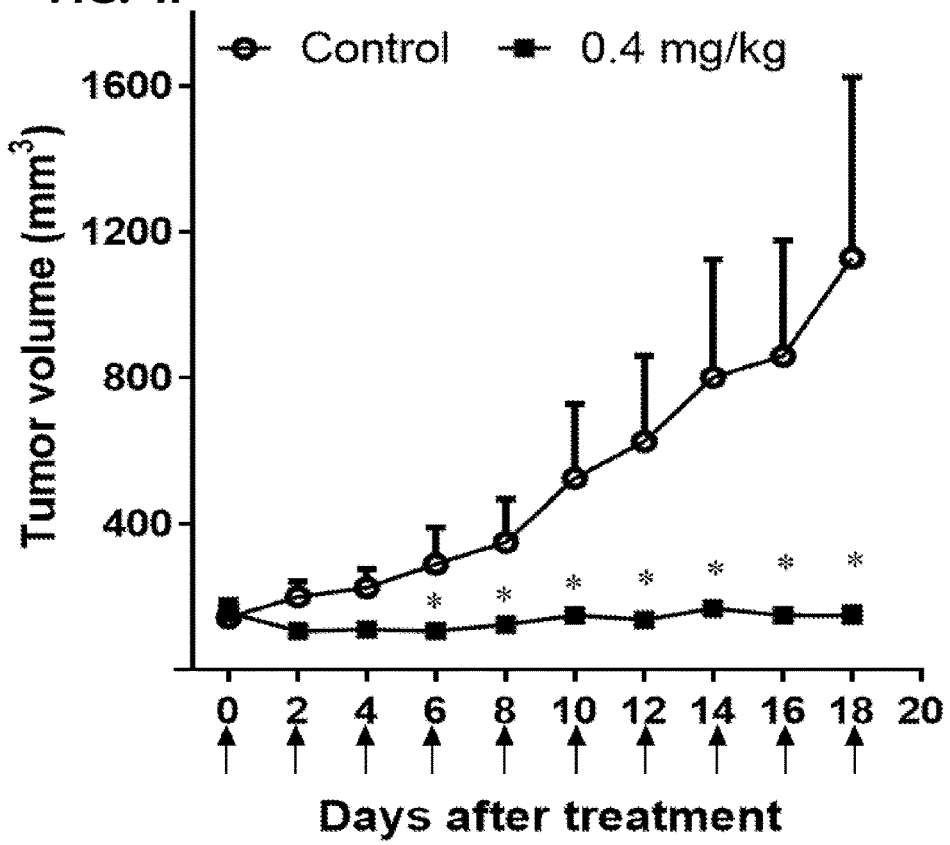
Figure 4G:
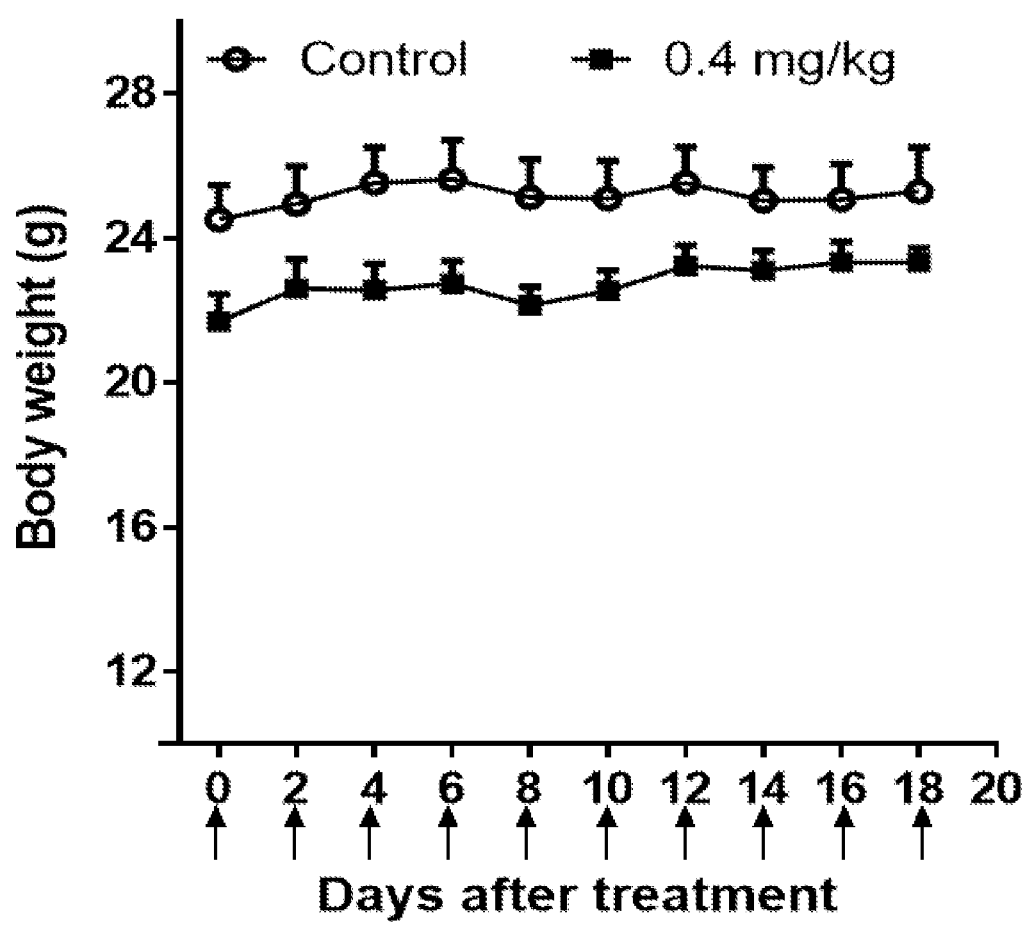

To evaluate the anti-tumor activity of LH7-PE38 in vivo, nude mice were subcutaneously inoculated with LAN1 cells. When tumors reached an average volume of 150 mm$^3$, mice were treated with LH7-PE38 every other day for a total of 10 injections. The different dose concentrations were used to determine the relative toxicity of the LH7-PE38 immunotoxin. As shown in FIG. 4E, the mice tolerated 0.4 mg/kg LH7-PE38 well. However, mice treated with 0.8 mg/kg died after 5 injections. Only two mice survived after 10 injections at the 0.6 mg/kg dose. Notably, 0.4 mg/kg of LH7-PE38 inhibited tumor growth during treatment without affecting body weight (FIGS. 4F and 4G). At the end of treatment, tumor volumes in the LH7-PE38-treated group were significantly smaller than those in the control group (FIG. 4H). In addition to measuring body weight, toxicology studies were also performed to further evaluate any side effects of LH7-PE38 at 0.4 mg/kg. The LH7-PE38 treated mice had an increase in white blood cells, indicating that the immunotoxin may be causing inflammatory effects in vivo (Table 7). In addition, the LH7-PE38 treated group showed an increase in alanine aminotransferase; however, we did not find any gross evidence of liver damage following mouse necropsy. All organ weights of the treated mice were statistically similar to those of the control group, except for the spleen. No significant differences were detected in any other parameters measured. In conclusion, immunotoxins based on the disclosed anti-GPC2 human single domains inhibited neuroblastoma cell proliferation both in vitro and in vivo.

TABLE 7

Toxicity of the LH7-PE38 immunotoxin in LAN1 neuroblastoma xenograft mice

| Parameters | Control | LH7-PE38 | Normal Values |
|---|---|---|---|
| White blood cells (K/μl) | 3.65 ± 0.77 | 8.15 ± 1.62* | 1.80-10.70 |
| Red blood cells (M/μl) | 7.53 ± 1.46 | 9.15 ± 0.90 | 6.36-9.42 |
| Albumin (g/dL) | 4.50 ± 0.17 | 4.23 ± 0.35 | 1.6-2.8 |
| Alkaline phosphatase (U/L) | 62.00 ± 7.55 | 77.67 ± 9.50 | 67-282 |
| Alanine aminotransferase (U/L) | 49.33 ± 10.21 | 842.33 ± 409.49* | 29-181 |
| Total bilirubin (mg/dL) | 0.30 ± 0.00 | 0.30 ± 0.00 | 0.0-0.6 |
| Creatinine (mg/dL) | 0.20 ± 0.00 | 0.50 ± 0.14 | 0.2-0.4 |
| Hemoglobin (g/dL) | 11.43 ± 2.04 | 13.77 ± 0.29 | 11.00-15.10 |
| Total protein (g/dL) | 6.27 ± 0.23 | 5.67 ± 0.35 | 4.2-5.9 |
| Blood urea nitrogen (mg/dL) | 21.33 ± 3.51 | 19.00 ± 2.65 | 12-52 |

TABLE 7-continued

Toxicity of the LH7-PE38 immunotoxin in LAN1 neuroblastoma xenograft mice

| Parameters | Control | LH7-PE38 | Normal Values |
|---|---|---|---|
| Select organ weight (mg) | | | |
| Brain | 0.50 ± 0.02 | 0.46 ± 0.03 | |
| Heart | 0.15 ± 0.02 | 0.14 ± 0.02 | |
| Kidney | 0.37 ± 0.04 | 0.33 ± 0.03 | |
| Liver | 1.35 ± 0.17 | 1.47 ± 0.14 | |
| Lung | 0.19 ± 0.05 | 0.18 ± 0.06 | |
| Spleen | 0.14 ± 0.00 | 0.10 ± 0.01* | |

Representative toxicological data and organ weights for LAN1 xenografted mice (n = 3/group) treated with LH7-PE38 (i.v. every other day, 0.4 mg/kg).
Data represent mean ± s.e.m.
*$P < 0.05$.

GPC2 CAR T Cells Kill Neuroblastoma Cells

Figure 5A:
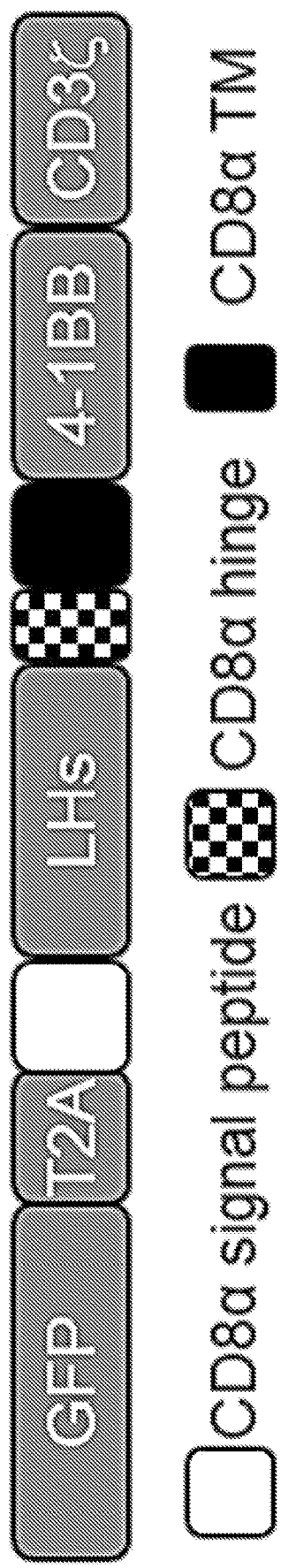
FIGS. 5A-5G: CAR T cells targeting GPC2 kill neuroblastoma cells.
Figure 5B:
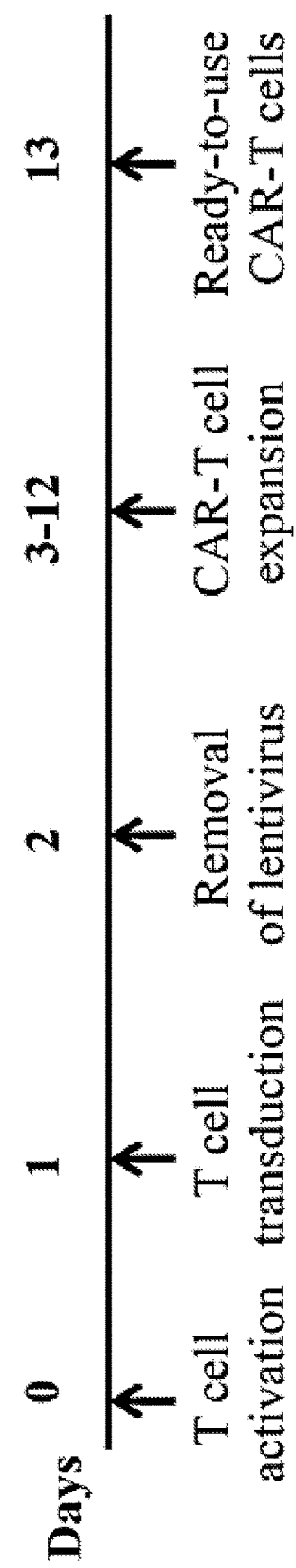
Figure 5C:
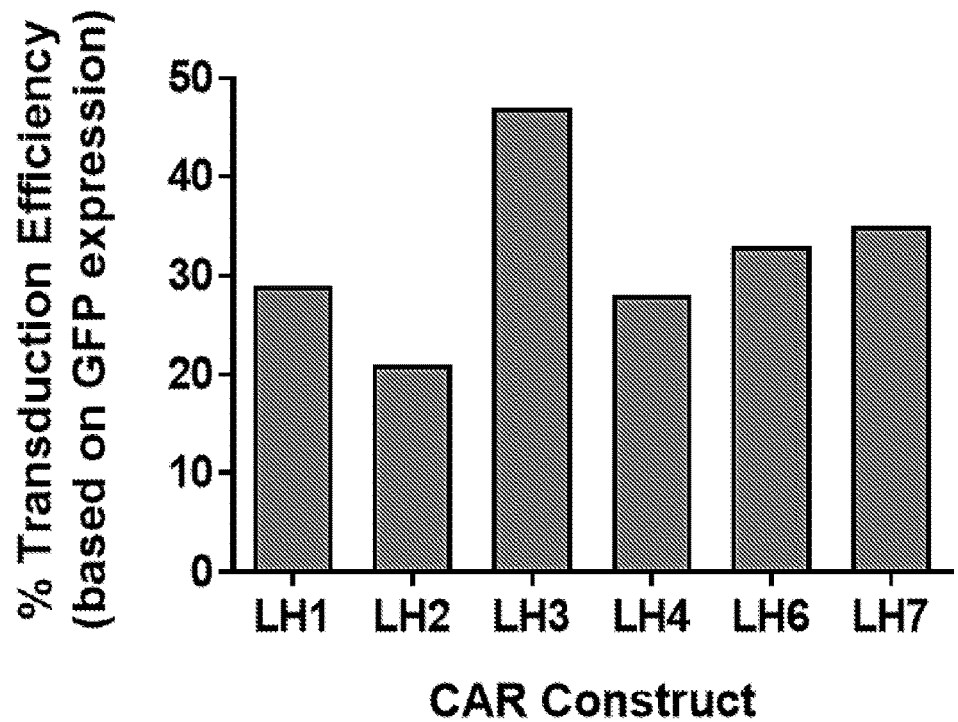
Figure 5D:
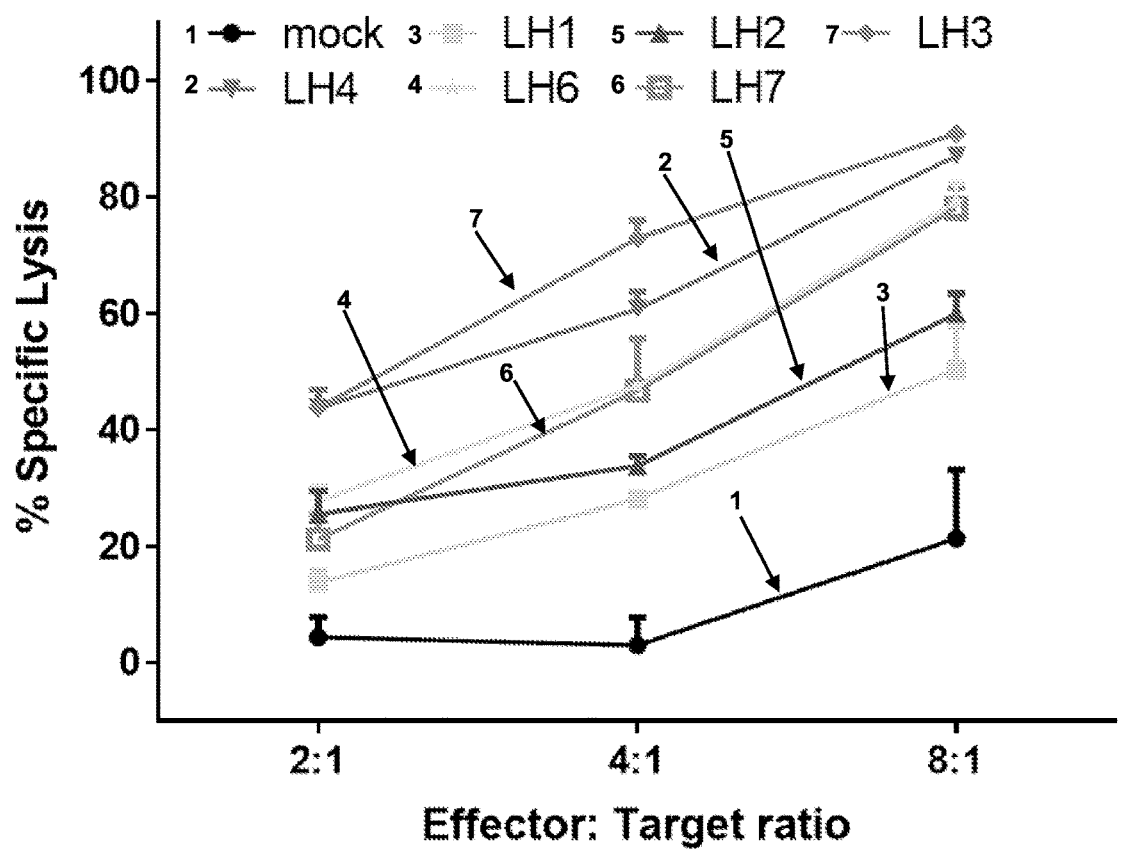
Figure 5E:
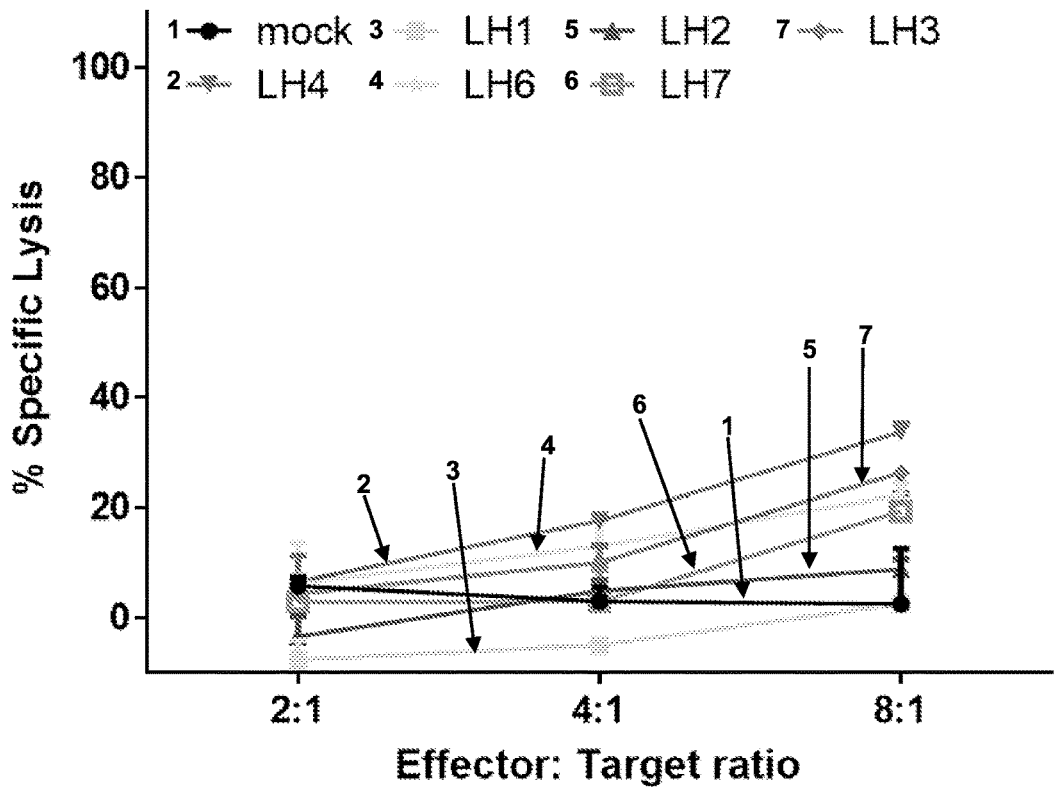
Figure 5F:
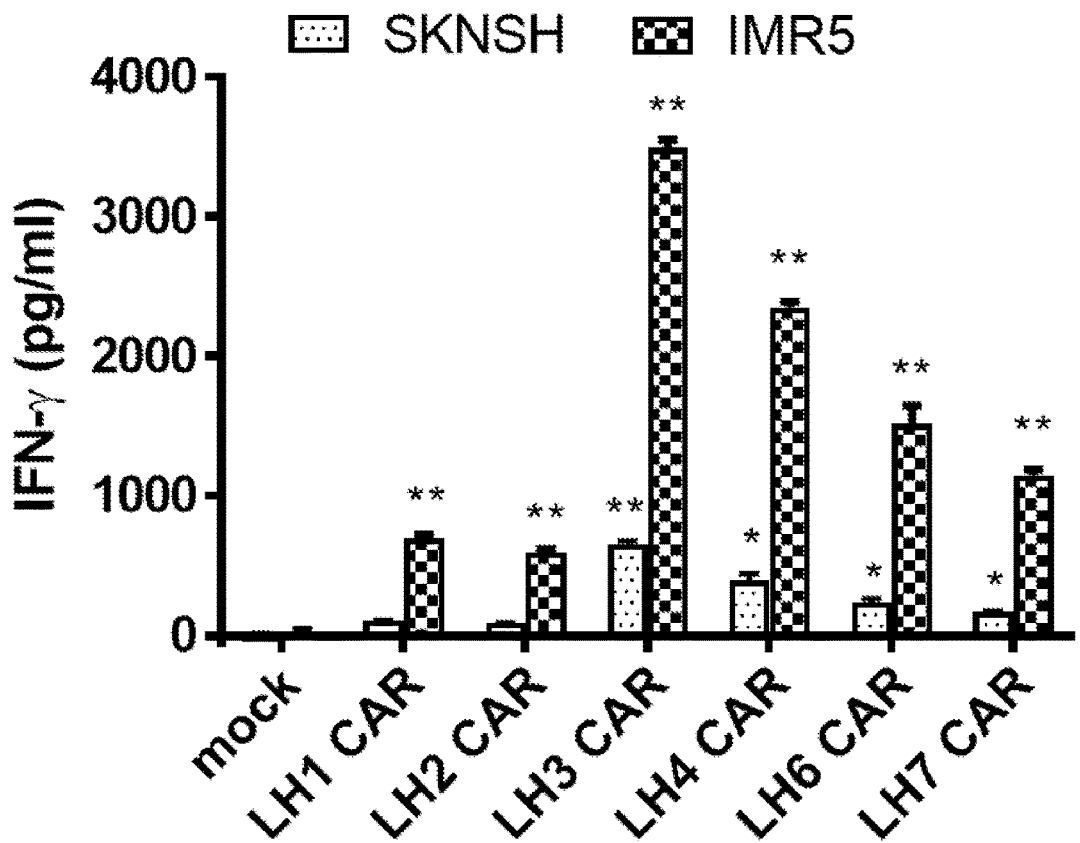
Figure 5G:
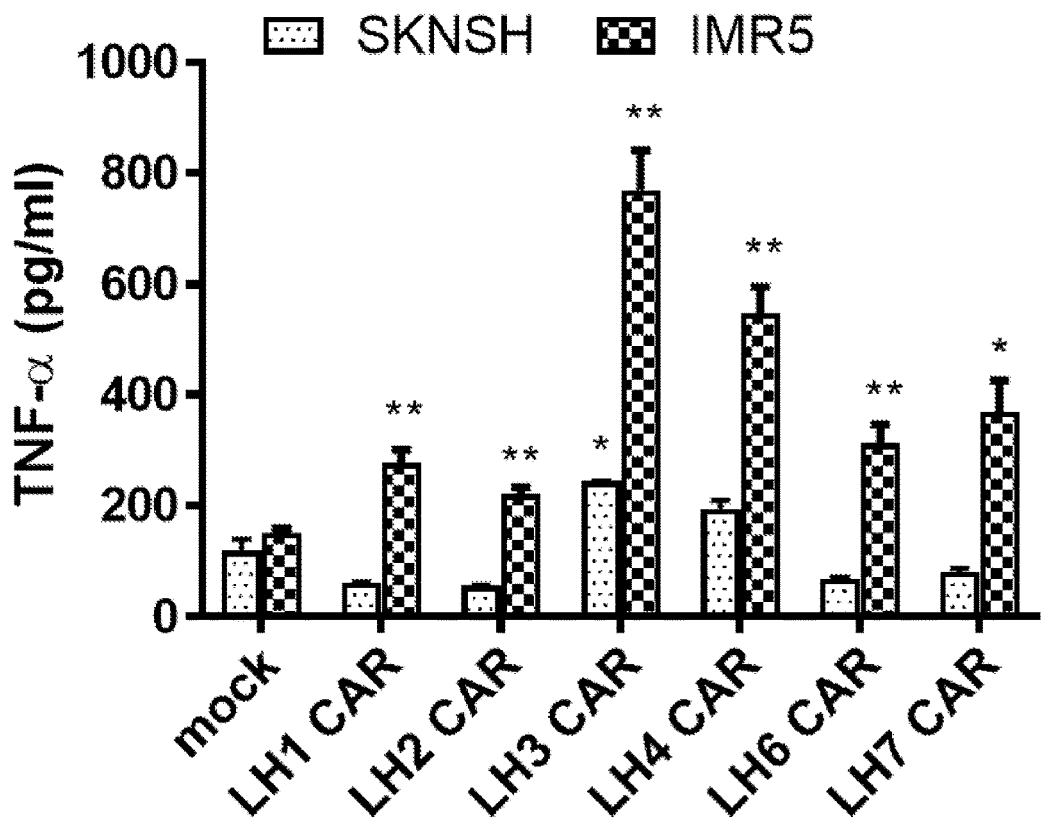
Figure 12:
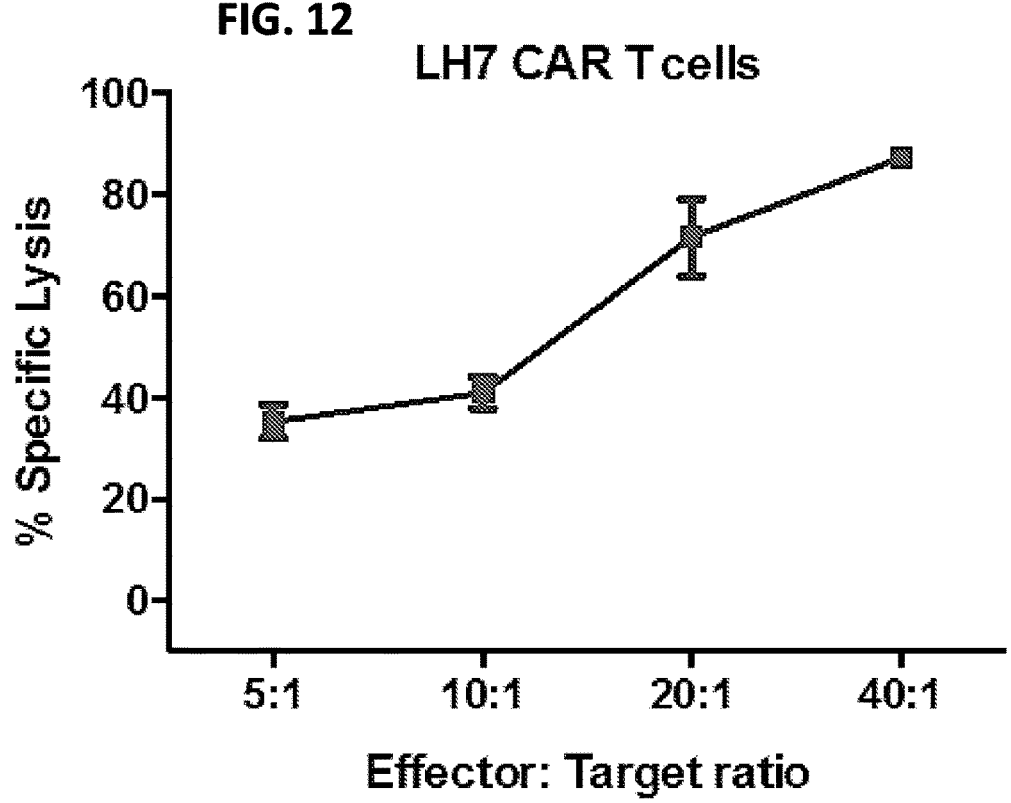
FIG. 12: Cytotoxic activity of LH7 CAR T cells in LAN1 neuroblastoma cells. The luciferase expressing LAN1 cells were co-cultured with LH7 CAR-transduced T cells at the indicated E:T ratios for 20 hours, and specific lysis was measured using a luminescent-based cytolytic assay.

To explore other therapeutic approaches, CARs were constructed containing anti-GPC2 antibody single domains linked to a CD8a hinge and transmembrane region, followed by the 4-1BB costimulatory signaling moiety and the cytoplasmic component of CD3ζ signaling molecule. The upstream GFP reporter was co-expressed with CAR using the "self-cleaving" T2A peptide (FIG. 5A). The genetically modified T cells began to expand after activation (FIG. 5B). On day 9, the expression of GPC2 CARs in the transduced T cells was demonstrated through GFP expression. The transduction efficiencies of CARs were between 21% and 47% (FIG. 5C). To determine whether T cells targeting GPC2 could specifically recognize and kill GPC2-positive neuroblastoma cells, a luminescent-based cytolytic assay was established using the neuroblastoma cells engineered to express luciferase. As shown in FIG. 5D, IMR5 cells which express high levels of GPC2, are resistant to mock-transduced T-cell-mediated killing. This was true even at E:T ratios as high as 8:1. Conversely, IMR5 cells were efficiently lysed by the GPC2 CAR T cells in a dose-dependent manner. In addition, anti-GPC2 CAR T cells demonstrated equivalent lytic capacity against LAN1 neuroblastoma cells (FIG. 12). The mock-transduced T cells and GPC2 CAR T cells showed similarly low cytolytic activity against the low GPC2 expressing SKNSH cells (FIG. 5E). A cytokine production assay revealed that GPC2 CAR T cells produced significantly more IFN-γ and TNF-α after exposure to IMR5 cells, than the mock T cells (FIGS. 5F and 5G). However, little to no induction of IFN-γ and TNF-α secretions were observed when mock or GPC2 CAR T cells were co-cultured with SKNSH cells.

Figure 6A:
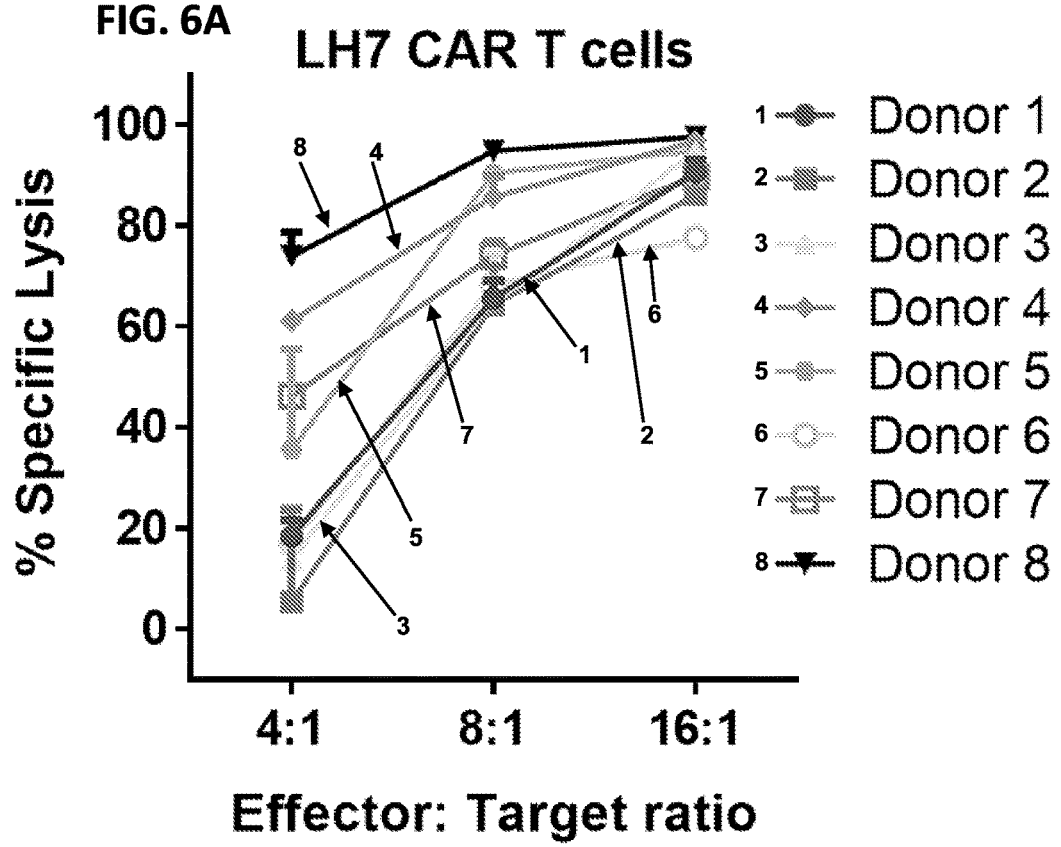
FIGS. 6A-6C: GPC2 specific CAR T cells demonstrate potent activity in mice bearing human neuroblastomas.
Figure 6B:
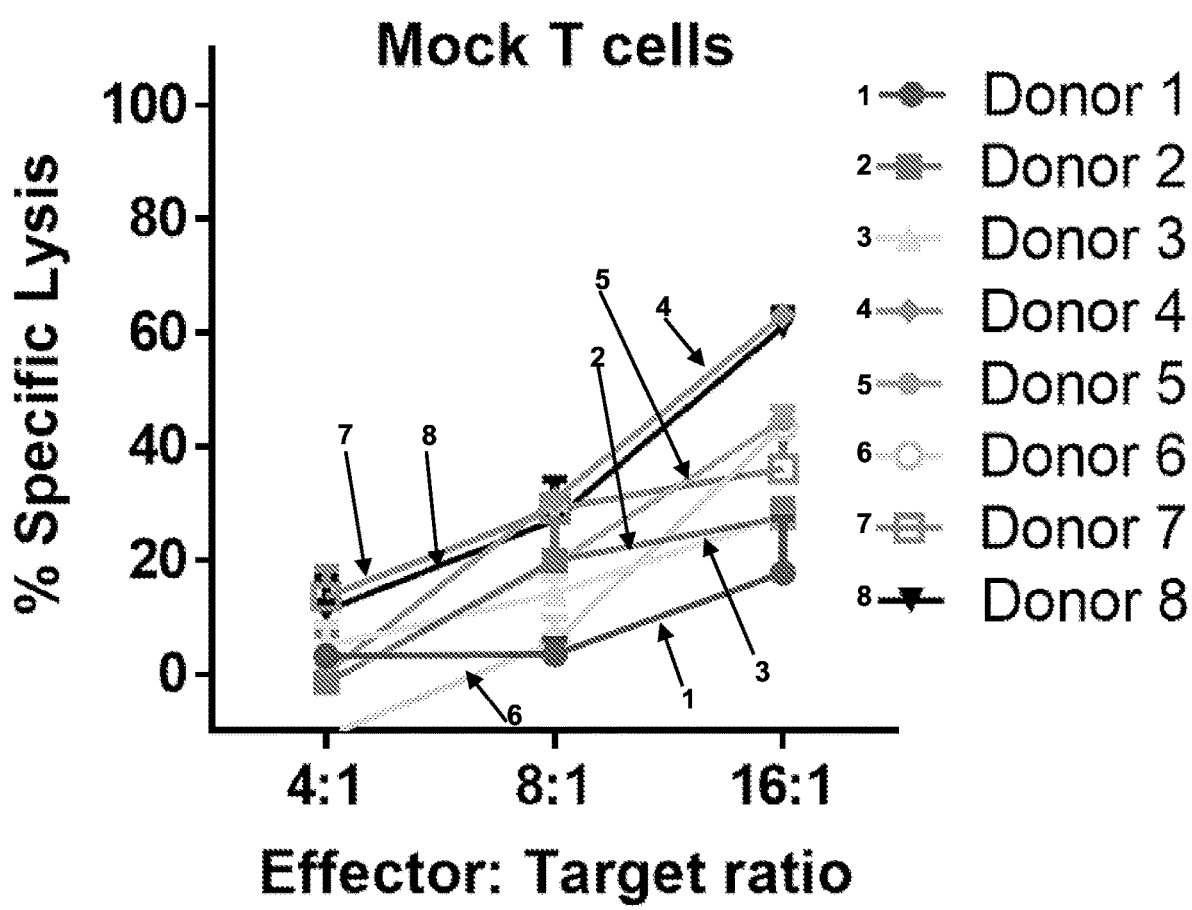

The killing ability of CAR T cells generated from eight individual human donors was tested. At an E:T ratio of 8:1, GPC2-specific CART cells lytic activity against IMR5 neuroblastoma cells ranged from 44% to 71%, with an average of 56% (FIG. 6A). Minimal cell lysis was observed in IMR5 cells treated with mock T cells (FIG. 6B). Next, the antitumor activity of GPC2-targeting CAR T cells was assessed in nude mice intravenously engrafted with luciferase expressing IMR5 cells. Although LH3 CAR T cells were the most potent in cell killing assay (FIG. 5D), the LH3 phage binder was also cross reactive with other glypican members (e.g. GPC3) (FIG. 1E). Therefore, LH7 was chosen for preclinical testing in neuroblastoma models.

Figure 6C:
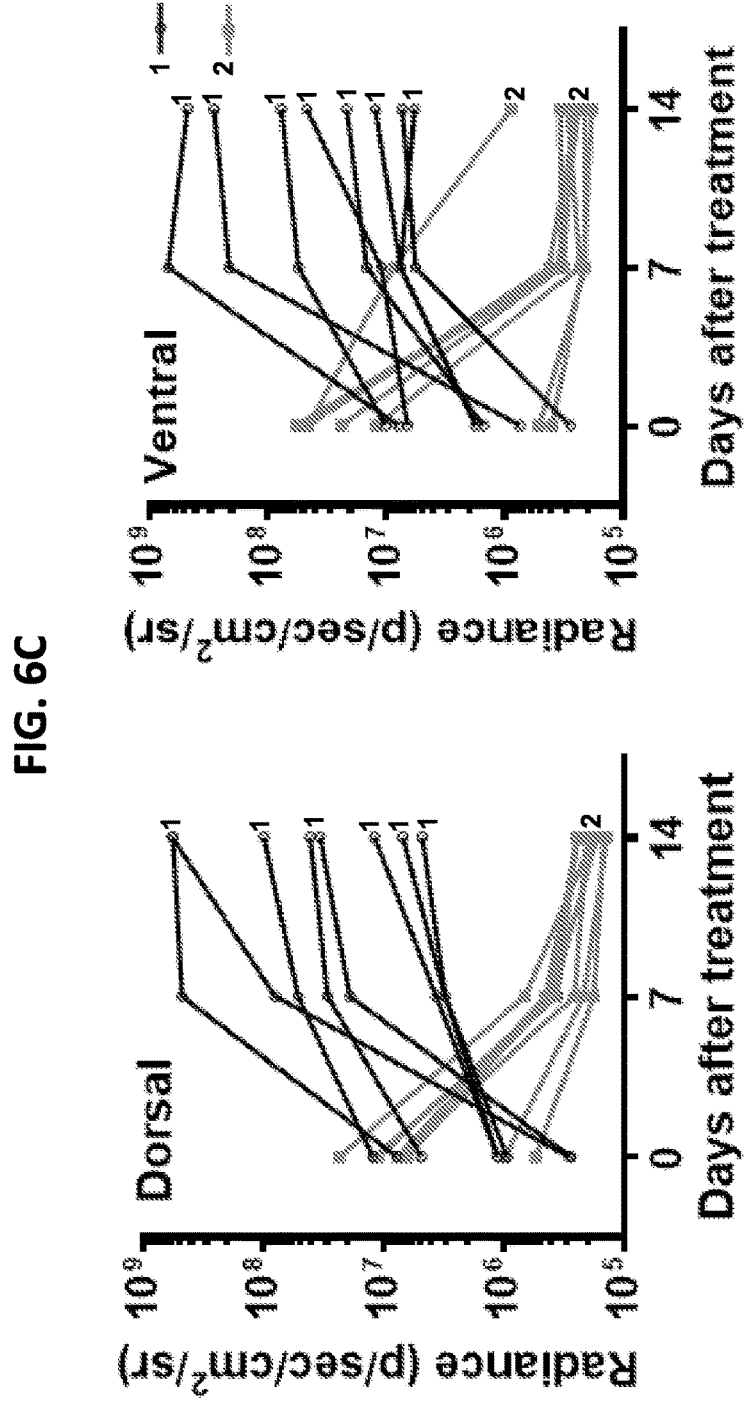
Figure 13:
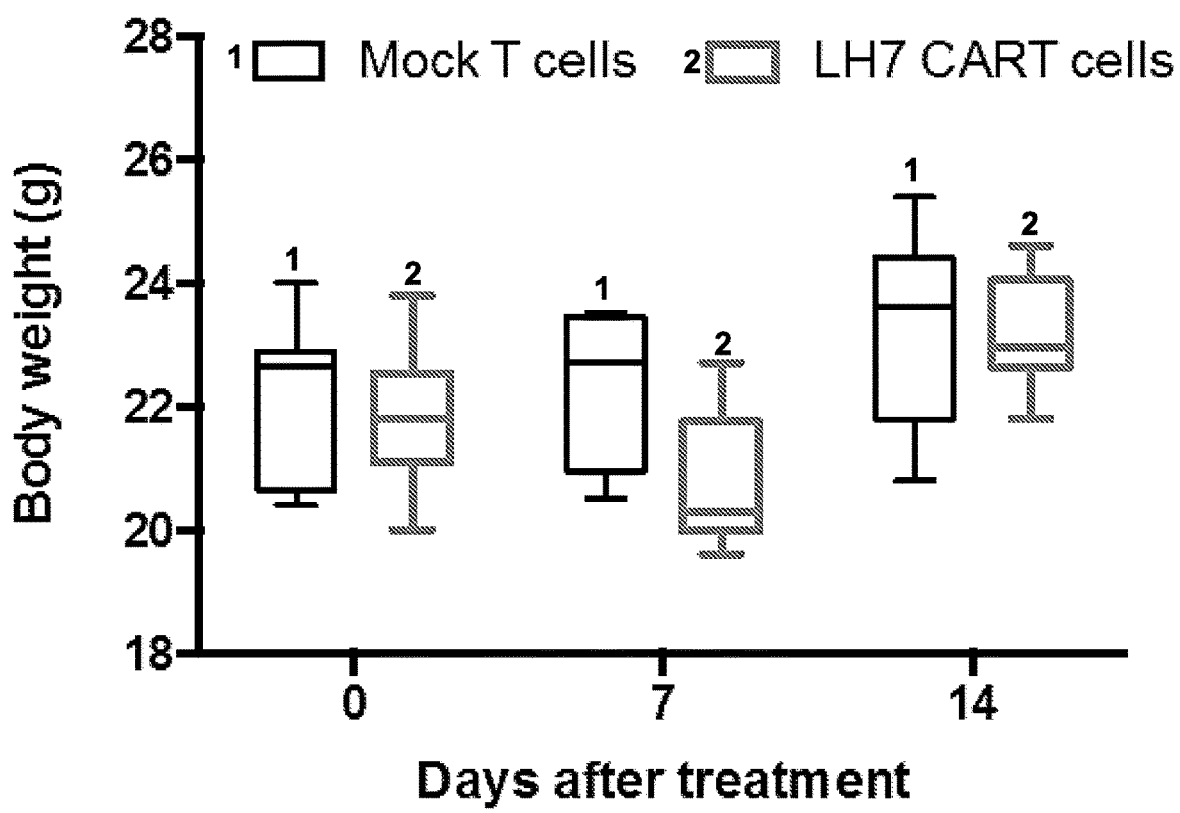
FIG. 13: Body weight of the mice with disseminated neuroblastoma tumors that were treated with either mock T cells or LH7 CAR T cells (n=8/group).
Figure 14A:
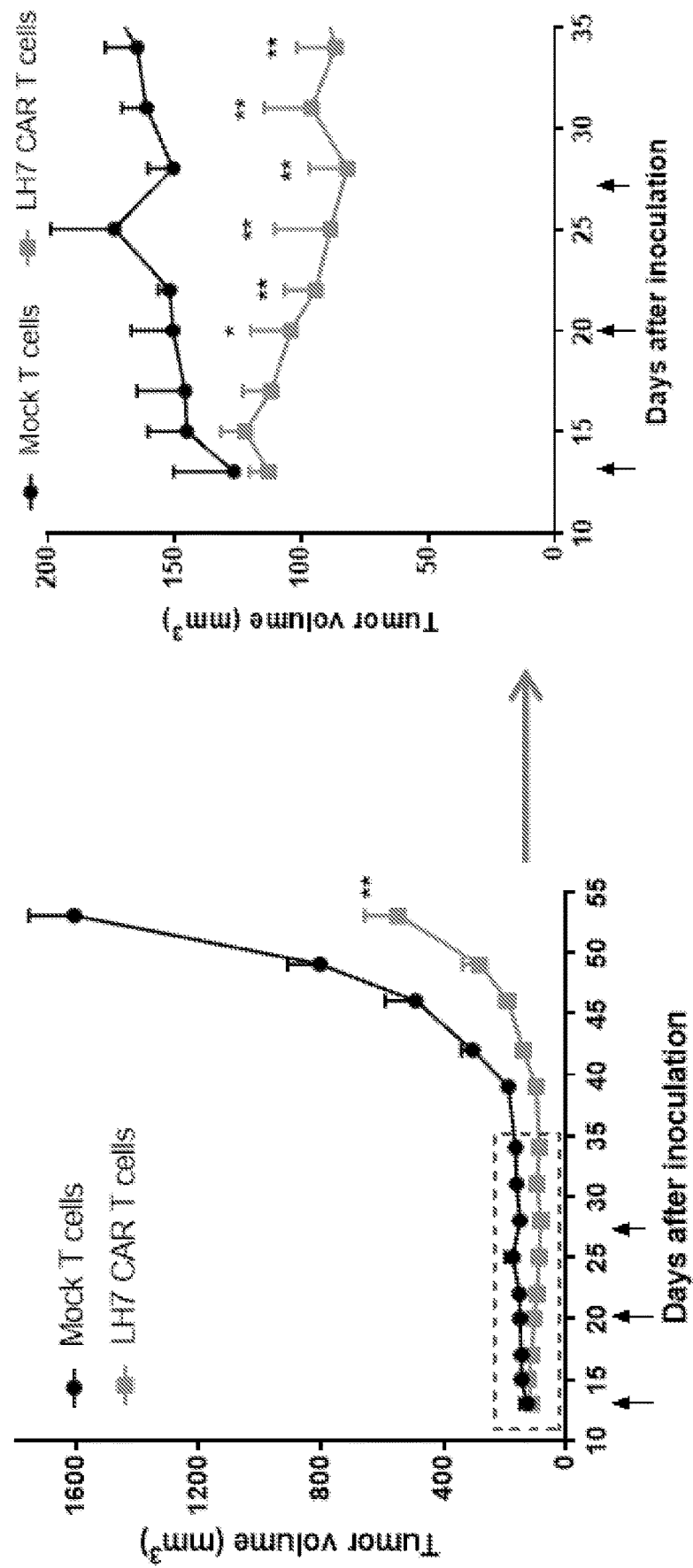
FIGS. 14A-14B: Inhibition of neuroblastoma xenograft tumor growth by LH7 CAR T cells.
Figure 14B:
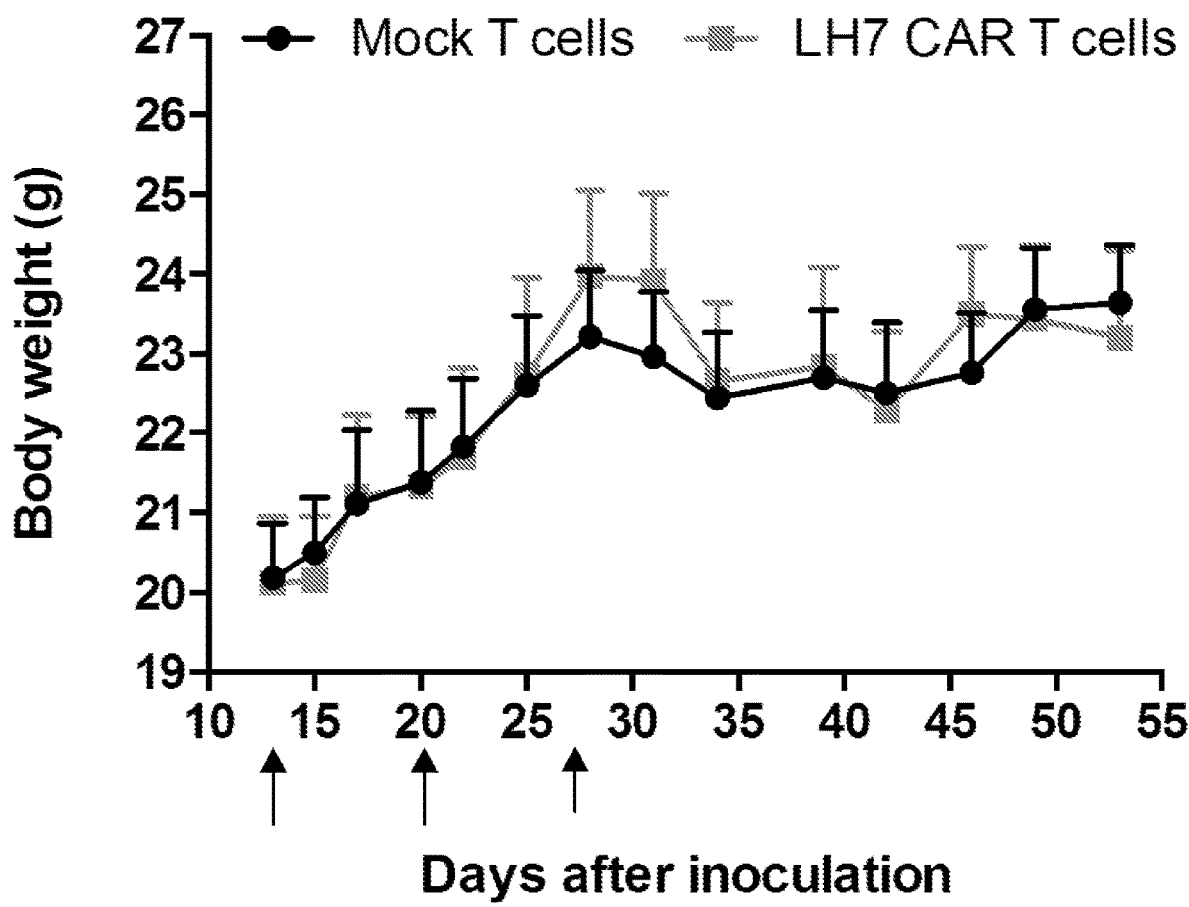

Bioluminescence imaging using IVIS showed that IMR5-bearing nude mice developed disseminated tumor lesions surrounding spine and bones. LH7 CAR T cells effectively suppressed metastatic tumors after 14 days of T cell infusion, whereas mock T cells failed to reduce tumor burden (FIG. 6C). Four out of eight (50%) of the mice treated with CAR T cells targeting GPC2 were tumor free at the end of this study. Neither mock T cells nor LH7 CAR T cells treatment affected mice body weight (FIG. 13). The efficacy of GPC2 targeting CAR T cells was also evaluated in a LAN1 xenograft mouse model. LH7 CAR T cells initially led to a reduction in tumor size and significantly suppressed tumor growth when compared to the control group at the end of study (FIG. 14). Taken together, it has been demonstrated that the disclosed single domain antibodies can be used to construct CAR T cells that are able to kill GPC2-expressing neuroblastoma cells in cell and mouse models.

Therapeutic Applications

It is demonstrated herein that GPC2 protein expression levels are elevated in human neuroblastoma tumors as compared with normal tissues. Genetic silencing of GPC2 also decreased neuroblastoma cell viability and induced apoptosis. It was also determined that GPC2 modulated Wnt/β-catenin signaling and the expression of the key oncogenic driver gene N-Myc in neuroblastoma. Seven heavy chain single-domain antibodies targeting GPC2 were identified by phage display. The immunotoxins and CARs based on these antibodies significantly inhibited neuroblastoma tumor cell growth. These findings indicate that GPC2 is an important therapeutic target in neuroblastoma.

An emerging approach to treating high-risk patients with neuroblastoma is immunotherapy targeting a tumor-associated antigen, for example, the disialoganglioside GD2. Anti-GD2 antibodies have been tested in clinical trials for neuroblastoma, with proven safety and efficacy (Yu et al., *New Engl J Med* 363:1324-1334, 2010; Cheung et al., *J Clin Oncol* 30:3264-3270, 2012). The US Food and Drug Administration (FDA) approved Unituxin, in combination with granulocyte-macrophage colony-stimulating factor (GM-CSF), interleukin-2 (IL-2), and 13-cis-retinoic acid (RA), for the treatment of patients with high-risk neuroblastoma in 2015. However, in patients with advanced disease, anti-GD2 antibodies only show limited activity. GD2 therapy is also associated with severe pain toxicity (Handgretinger et al., *Eur J Cancer* 21A(2):261-267, 1995; Yu et al., *J Clin Oncol* 16(6):2169-2180, 1998). These challenges emphasize the necessity of identifying a new target for neuroblastoma therapy.

Given the importance of Wnt/β-catenin signaling in neuroblastoma (Clevers and Nusse, *Cell* 149, 1192-1205, 2012; Chenn and Walsh, *Science* 297:365-369, 2002; Lee et al., *Science* 303:1020-1023, 2004), studies were carried out to determine if GPC2 inhibition could suppress this signaling pathway in neuroblastoma cells. GPC2 inhibition by the disclosed anti-GPC2 antibodies or knockout by sgRNA was found to reduce the expression of active-β-catenin and suppress target genes that may regulate neuroblastoma cell proliferation and survival. A previous study found that GPC3 could interact with Wnt3a to suppress hepatocellular carcinoma cell proliferation (Gao et al., *Hepatology* 60(2):576-587, 2014). Wnt11 is secreted in regions adjacent to the neural crest and could induce neural crest migration (De Calisto et al., *Development* 132(11):2587-2597, 2005). It has been shown that Wnt11 mRNA was highly expressed in neuroblastoma clinical samples (Wai et al., *Int J Oncol* 20(3):441-451, 2002). Thus, studies disclosed herein evaluated the expression of Wnt3a and Wnt11 in neuroblastoma cell lines. Wnt3a and Wnt11 were expressed in GPC2-high expressing neuroblastoma cells (e.g. LAN1, IMR5, LAN5 and IMR32). By contrast, Wnt3a and Wnt11 proteins were either not detected or poorly detected in GPC2-low expressing SKNSH cells. The differences in Wnt protein expression are in agreement with the sensitivity of GPC2-targeted immunotoxins and CAR T cells in LAN1/IMR5 and SKNSH cell lines. Furthermore, it was demonstrated that GPC2 could co-immunoprecipitate with Wnt3a. These observations are consistent with previous reports showing that activation of Wnt/β-catenin signaling contributes to the aggressiveness of neuroblastoma (Colombres et al., *J Cell Physiol* 216:805-815, 2008; Liu et al., *Oncogene* 27:1478-1488, 2008) and indicate the role of GPC2 in modulation of Wnt signaling in neuroblastoma cells. N-Myc is a key driver for neuroblastoma tumorigenesis (Brodeur and Seeger, *Cancer Genet Cytogenet* 19(1-2):101-111, 1986; Brodeur et al., *Science* 224(4653):1121-1124, 1984; Seeger et al., *New Engl J Med* 313(18):1111-1116, 1985). It was demonstrated herein that N-Myc was expressed in MYCN-amplified neuroblastoma cells including LAN1, IMR5, LAN5 and IMR32 (FIG. 3J). However, N-Myc protein was not found in MYCN-non-amplified SKNSH neuroblastoma cells. The present study found genetic silencing of GPC2 significantly inhibited the expression of N-Myc in neuroblastoma cells. It has been shown that Wnt signaling can regulate N-Myc expression level and β-catenin may activate the promoter of N-Myc during development (Shu et al., *Dev Biol* 283(1): 226-239, 2005; ten Berge et al., *Development* 135(19):3247-3257, 2008). The result described herein indicates that GPC2 can downregulate N-Myc expression by inhibiting Wnt/β-catenin signaling.

Protein surfaces contain clefts that are relatively inaccessible to conventional antibodies as a result of steric hindrance. Single domain antibodies have the ability to bind in protein clefts or hidden substrate pockets not accessible to conventional antibodies (De Genst et al., *Proc Natl Acad Sci USA* 103:4586-4591, 2006; Stanfield et al., *Science* 305: 1770-1773, 2004). A human single domain antibody was previously identified that recognizes a cryptic functional site on GPC3 and inhibits Wnt signaling in liver cancer (Gao et al., *Nat Commun* 6:6536, 2015). In the present study, a group of seven representative binders specific for GPC2 were isolated, and all of these single domain antibodies significantly inhibited Wnt/β-catenin signaling in neuroblastoma cells. Together, these studies indicate that single domain antibodies are an emerging class of promising therapeutic candidates that can inhibit the signaling related to the growth of cancer cells by blocking receptor-ligand interactions.

The immunotoxins based on the disclosed anti-GPC2 antibodies demonstrated highly specific and potent killing of neuroblastoma in both in vitro and in vivo mouse models. In mouse testing, the optimal dose appears to be 0.4 mg/kg, which is similar to the dose of other immunotoxins that are currently being evaluated in preclinical and clinical stages (including Phase III) (Mazor et al., *Immunol Rev* 270(1): 152-164, 2016).

CAR T cells have been shown to be a promising T-cell based immunotherapy in leukemia (Kochenderfer et al., *Blood* 119:2709-2720, 2012; Kochenderfer and Rosenberg, *Nat Rev Clin Oncol* 10:267-276, 2013; Grupp et al., *New Engl J Med* 368:1509-1518, 2013; Sterman et al., *Clin Cancer Res* 13:4456-4466, 2007; Maus et al., *Blood* 123: 2625-2635, 2014). CAR T cells targeting CD19 have resulted in sustained complete responses and have shown complete response rates of approximately 90% in patients with relapsed or refractory acute lymphoblastic leukemia (Maus and June, *Clin Cancer Res* 22(8):1875-1884, 2016). However, CAR T cell therapies have not yet been successful in treating solid tumors. The present study sought to evaluate the use of CAR T cells in treating neuroblastoma. An in vivo bioluminescent model of disseminated neuroblastoma was established in mice. Most neuroblastomas begin in the abdomen in the adrenal gland or next to the spinal cord, or in the chest. Neuroblastomas can spread to the bones, such as in the face, skull, pelvis and legs. They can also spread to bone marrow, liver, lymph nodes, skin and orbits. In the present study, disseminated tumors were frequently found near the spine and in the bones of face, skull, legs and pelvis, indicating the clinical relevance of the animal model. It was then demonstrated that a single infusion of LH7 CAR T cells significantly suppressed the growth of metastatic neuroblastoma cells in mice and led to complete remission in 50% of treated mice.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated variable heavy (VH) single domain monoclonal antibody that binds glypican-2 (GPC2), comprising a complemetarity determining region 1 (CDR1), a CDR2 and a CDR3, wherein the VH single domain monoclonal antibody comprises:
the CDR1, CDR2 and CDR3 sequences of SEQ ID NO: 2;
the CDR1, CDR2 and CDR3 sequences of SEQ ID NO: 4;
the CDR1, CDR2 and CDR3 sequences of SEQ ID NO: 6;
the CDR1, CDR2 and CDR3 sequences of SEQ ID NO: 8;
the CDR1, CDR2 and CDR3 sequences of SEQ ID NO: 10; or
the CDR1, CDR2 and CDR3 sequences of SEQ ID NO: 12.

2. The VH single domain monoclonal antibody of claim 1, wherein the CDR sequences are determined using the IMGT, Kabat or Chothia numbering scheme.

3. The VH single domain monoclonal antibody of claim 2, wherein the CDR1, CDR2 and CDR3 sequences are determined using IMGT and are respectively set forth as:
residues 26-33, 51-57 and 96-114 of SEQ ID NO: 2;
residues 26-33, 51-57 and 96-106 of SEQ ID NO: 4;
residues 26-33, 51-57 and 96-110 of SEQ ID NO: 6;
residues 26-33, 51-57 and 96-109 of SEQ ID NO: 8;
residues 26-33, 51-58 and 97-110 of SEQ ID NO: 10; or
residues 26-33, 51-57 and 96-109 of SEQ ID NO: 12.

4. The VH single domain monoclonal antibody of claim 2, wherein the CDR1, CDR2 and CDR3 sequences are determined using Kabat and are respectively set forth as:
residues 31-35, 50-65 and 96-114 of SEQ ID NO: 2;
residues 31-35, 50-65 and 96-106 of SEQ ID NO: 4;
residues 31-35, 50-65 and 96-110 of SEQ ID NO: 6;
residues 31-35, 50-65 and 96-109 of SEQ ID NO: 8;
residues 31-35, 50-66 and 97-110 of SEQ ID NO: 10; or
residues 31-35, 50-65 and 96-109 of SEQ ID NO: 12.

5. The VH single domain monoclonal antibody of claim 1, wherein:
the amino acid sequence of the antibody is at least 90% identical to SEQ ID NO: 2 and the antibody comprises the CDR1, CDR2 and CDR3 sequences of SEQ ID NO: 2;
the amino acid sequence of the antibody is at least 90% identical to SEQ ID NO: 4 and the antibody comprises the CDR1, CDR2 and CDR3 sequences of SEQ ID NO: 4;
the amino acid sequence of the antibody is at least 90% identical to SEQ ID NO: 6 and the antibody comprises the CDR1, CDR2 and CDR3 sequences of SEQ ID NO: 6;
the amino acid sequence of the antibody is at least 90% identical to SEQ ID NO: 8 and the antibody comprises the CDR1, CDR2 and CDR3 sequences of SEQ ID NO: 8;
the amino acid sequence of the antibody is at least 90% identical to SEQ ID NO: 10 and the antibody comprises the CDR1, CDR2 and CDR3 sequences of SEQ ID NO: 10; or
the amino acid sequence of the antibody is at least 90% identical to SEQ ID NO: 12 and the antibody comprises the CDR1, CDR2 and CDR3 sequences of SEQ ID NO: 12.

6. The VH single domain monoclonal antibody of claim 1, wherein the amino acid sequence of the antibody comprises or consists of SEQ ID NO: 2, SEQ ID NO: 4, SEQ ID NO: 6, SEQ ID NO: 8, SEQ ID NO: 10 or SEQ ID NO: 12.

7. The VH single domain monoclonal antibody of claim 1, which is a chimeric, synthetic, humanized or human antibody.

8. An immunoconjugate comprising the VH single domain monoclonal antibody of claim 1 and an effector molecule.

9. The immunoconjugate of claim 8, wherein the effector molecule is a toxin.

10. The immunoconjugate of claim 9, wherein the toxin is *Pseudomonas* exotoxin or a variant thereof.

11. The immunoconjugate of claim 10, wherein the *Pseudomonas* toxin is PE38.

12. The immunoconjugate of claim 8, wherein the effector molecule is a detectable label.

13. The immunoconjugate of claim 12, wherein the detectable label comprises a fluorophore, an enzyme or a radioisotope.

14. A chimeric antigen receptor (CAR) comprising the VH single domain monoclonal antibody of claim 1.

15. The CAR of claim 14, further comprising a hinge region, a transmembrane domain, a costimulatory signaling moiety, a signaling domain, or any combination thereof.

16. The CAR of claim 15, wherein the hinge region comprises a CD8α hinge region, the transmembrane domain comprises a CD8α or a CD28 transmembrane domain, the costimulatory signaling moiety comprises a 4-1BB and/or a CD28 signaling moiety, the signaling domain comprises a CD3ζ signaling domain, or any combination thereof.

17. An isolated cell expressing the CAR of claim 14.

18. An antibody-drug conjugate (ADC) comprising a drug conjugated to the VH single domain monoclonal antibody of claim 1.

19. The ADC of claim 18, wherein the drug is a small molecule.

20. The ADC of claim 18, wherein the drug is an anti-microtubule agent, an anti-mitotic agent and/or a cytotoxic agent.

21. A multi-specific antibody comprising the VH single-domain monoclonal antibody of claim 1 and at least one additional monoclonal antibody or antigen-binding fragment thereof.

22. The multi-specific antibody of claim 21, which is a bispecific antibody or a trispecific antibody.

23. The multi-specific antibody of claim 21, wherein the at least one additional monoclonal antibody or antigen binding fragment thereof specifically binds a component of the T cell receptor or a natural killer (NK) cell activating receptor.

24. An antibody-nanoparticle conjugate, comprising a nanoparticle conjugated to the VH single-domain monoclonal antibody of claim 1.

25. The antibody-nanoparticle conjugate of claim 24, wherein the nanoparticle comprises a polymeric nanoparticle, nanosphere, nanocapsule, liposome, dendrimer, polymeric micelle, or niosome.

26. The antibody-nanoparticle conjugate of claim 24, wherein the nanoparticle comprises a cytotoxic agent.

27. A fusion protein comprising the VH single domain monoclonal antibody of claim 1 and a heterologous protein or peptide.

28. The fusion protein of claim 27, wherein the heterologous protein is an Fc protein.

29. The fusion protein of claim 27, wherein the heterologous peptide is not endogenous to humans.

30. The fusion protein of claim 29, wherein the heterologous peptide is about 8 to about 20 amino acids in length.

31. The fusion protein of claim 29, wherein the heterologous peptide comprises or consists of NYHLENEVARLKKL (SEQ ID NO: 26).

32. A composition comprising a pharmaceutically acceptable carrier and the VH single domain monoclonal antibody of claim 1.

33. A nucleic acid molecule encoding the VH single domain monoclonal antibody of claim 1.

34. The nucleic acid molecule of claim 33, operably linked to a promoter.

35. A vector comprising the nucleic acid molecule of claim claim 33.

36. A method of treating a GPC2-positive cancer in a subject, comprising administering to the subject an immunoconjugate, a chimeric antigen receptor, or an antibody-drug conjugate comprising the VH single domain monoclonal antibody of claim 1, wherein the immunoconjugate comprises the VH single domain monoclonal antibody and a toxin.

37. The method of claim 36, wherein the GPC2-positive cancer is a pediatric cancer.

38. The method of claim 36, wherein the GPC2-positive cancer is a neuroblastoma, acute lymphoblastic leukemia, embryonal rhabdomyosarcoma, alveolar rhabdomyosarcoma, Ewing's sarcoma, desmoplastic small round cell tumor or osteosarcoma.

39. The method of claim 36, wherein the cancer is a neuroblastoma.

40. A method of inhibiting tumor growth or metastasis of a GPC2-positive cancer in a subject, comprising administering to the subject an immunoconjugate, a chimeric antigen receptor, or an antibody-drug conjugate comprising the VH single domain monoclonal antibody of claim 1, wherein the immunoconjugate comprises the VH single domain monoclonal antibody and a toxin.

41. A method of detecting expression of GPC2 in a sample, comprising:
   contacting the sample with the VH single domain monoclonal antibody of claim 1; and
   detecting binding of the antibody to the sample, thereby detecting expression of GPC2 in the sample.

42. The method of claim 41, wherein the VH single domain monoclonal antibody is directly labeled.

43. The method of claim 41, further comprising:
   contacting the VH single domain monoclonal antibody with a second antibody, and
   detecting the binding of the second antibody to the VH single domain monoclonal antibody, thereby detecting expression of GPC2 in the sample.

44. The method of claim 41, wherein the sample is obtained from a subject suspected of having a GPC2-positive cancer.

45. The method of claim 41, wherein the sample is a tumor biopsy.

* * * * *

SEQUENCE LISTING

```
<160> NUMBER OF SEQ ID NOS: 26

<210> SEQ ID NO 1
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 1
caggtgcagc tggtgcagtc tggggggaggc ttggtacagc ctggagggtc cctgagactc      60
tcctgtgcag cctctgattt cgatttcgct gcttatgaaa tgagctgggt ccgccaggct     120
ccagggaagg gtctagagtg gattgggaa atcaatcata gtggaagcac cacctacaac     180
ccgtccctca agagtcgagt caccatctcc agagacaatt ccaagaacac gctgtatctg     240
caaatgaaca ccctgagagc cgaggacaca gccgtgtatt actgtgcgac cgccgtgcat     300
```

```
tactatgata gtagtggtta ttaccatgat gcttttgata tctggggcca aggcaccctg    360
gtcaccgtct cctca                                                     375
```

<210> SEQ ID NO 2
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 2

```
Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Asp Phe Ala Ala Tyr
            20                  25                  30

Glu Met Ser Trp Val Arg Gln Ala Pro Gly Lys Gly Leu Glu Trp Ile
        35                  40                  45

Gly Glu Ile Asn His Ser Gly Ser Thr Thr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Val Tyr Tyr Cys Ala
                85                  90                  95

Thr Ala Val His Tyr Tyr Asp Ser Ser Gly Tyr Tyr His Asp Ala Phe
            100                 105                 110

Asp Ile Trp Gly Gln Gly Thr Leu Val Thr Val Ser Ser
        115                 120                 125
```

<210> SEQ ID NO 3
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 3

```
caggtgcagc tggtgcagtc tgggggaggc ttggtacagc ctggagggtc cctgagactc    60
tcctgtgcag cctctgattt ctatttctat tcttatgaag tgagctgggt ccgccaggct   120
ccagggaagg ccctggagtg gattgggtat atctattaca gtgggagcac cacctacaac   180
ccgtccctca agagtcgagt caccatctcc agagacaatt ccaagaacac gctgtatctg   240
caaatgaaca ccctgagagc cgaggacaca gccatatatt actgtgcggt ccgggacaac   300
tggaacgacg ttgactactg gggccaggga accctggtca ccgtctcctc a            351
```

<210> SEQ ID NO 4
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 4

```
Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Tyr Phe Tyr Ser Tyr
            20                  25                  30

Glu Val Ser Trp Val Arg Gln Ala Pro Gly Lys Ala Leu Glu Trp Ile
        35                  40                  45
```

Gly Tyr Ile Tyr Tyr Ser Gly Ser Thr Thr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Val Arg Asp Asn Trp Asn Asp Val Asp Tyr Trp Gly Gln Gly Thr Leu
            100                 105                 110

Val Thr Val Ser Ser
            115

<210> SEQ ID NO 5
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 5
caggtgcagc tggtgcagtc tggggggaggc ttggtacagc ctggagggtc cctgagactc    60
tcctgtgcag cctcttcttt ctctttcgct gattatgaaa tgagctgggt ccgccaggct   120
ccagggaagg ccctggagtg gattgggcgt atctatacca gtgggagcac aactacaac    180 ccctccctca gagtcgagt caccatctcc agagacaatt ccaagaacac gctgtatctg    240
caaatgaaca ccctgagagc cgaggacaca gccacatatt actgtgcgag aggatatagt    300
ggctacgatg gatcgcacta ctttgactac tggggccagg gaaccctggt caccgtctcc    360
tca                                                                  363

<210> SEQ ID NO 6
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 6

Gln Val Gln Leu Val Gln Ser Gly Gly Gly Leu Val Gln Pro Gly Gly
1               5                   10                  15

Ser Leu Arg Leu Ser Cys Ala Ala Ser Ser Phe Ser Phe Ala Asp Tyr
            20                  25                  30

Glu Met Ser Trp Val Arg Gln Ala Pro Gly Lys Ala Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Gly Tyr Ser Gly Tyr Asp Gly Ser His Tyr Phe Asp Tyr Trp Gly
            100                 105                 110

Gln Gly Thr Leu Val Thr Val Ser Ser
        115                 120

<210> SEQ ID NO 7
<211> LENGTH: 360
<212> TYPE: DNA
<213> ORGANISM: Artificial Sequence
<220> FEATURE:

<223> OTHER INFORMATION: Synthetic polynucleotide

<400> SEQUENCE: 7

```
caggtgcagc tggtgcagtc tggggaggc ttggtacagc ctggagggtc cctgagactc      60
tcctgtgcag cctcttcttt ctatttcgat gattatgaaa tgagctgggt ccgccaggct    120
ccagggaagg ccctggagtg gattgggcgt atctatacca gtgggagcac caactacaac    180
ccctccctca agagtcgagt caccatctcc agagacaatt ccaagaacac gctgtatctg    240
caaatgaaca ccctgagagc cgaggacaca gccacgtatt actgtgcgag ggatattgt     300
agtggtggta gctgctactt tgactactgg ggccaggaa ccctggtcac cgtctcctca    360
```

<210> SEQ ID NO 8
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 8

Gln Val Gln Leu Val Gln Ser Gly Gly Gly Leu Val Gln Pro Gly Gly
1               5                   10                  15

Ser Leu Arg Leu Ser Cys Ala Ala Ser Ser Phe Tyr Phe Asp Asp Tyr
            20                  25                  30

Glu Met Ser Trp Val Arg Gln Ala Pro Gly Lys Ala Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Gly Tyr Cys Ser Gly Gly Ser Cys Tyr Phe Asp Tyr Trp Gly Gln
            100                 105                 110

Gly Thr Leu Val Thr Val Ser Ser
        115                 120

<210> SEQ ID NO 9
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 9

```
caggtgcagc tggtgcagtc tggggaggc ttggtacagc ctggagggtc cctgagactc      60
tcctgtgcag cctctgattt ctatttcgat gattatgaaa tgagctgggt ccgccaggct    120
ccagggaagg ggctggagtg gtctcaact attagtggta gtggtggtgg cacatactac    180
gcagactcag tgaagggccg attcaccatc tccagagaca attccaagaa cacgctgtat    240
ctgcaaatga acaccctgag agccgaggac acagccacat attactgtgc gagaggttac    300
agttatgacg actcccgata ttttgactac tggggccagg gaaccctggt caccgtctcc    360
tca                                                                  363
```

<210> SEQ ID NO 10
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 10

Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Tyr Phe Tyr Asp Tyr
            20                  25                  30

Glu Met Ser Trp Val Arg Gln Ala Pro Gly Lys Gly Leu Glu Trp Val
        35                  40                  45

Ser Thr Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Thr Tyr Tyr Cys
                85                  90                  95

Ala Arg Gly Tyr Ser Tyr Asp Asp Ser Arg Tyr Phe Asp Tyr Trp Gly
            100                 105                 110

Gln Gly Thr Leu Val Thr Val Ser Ser
        115                 120

<210> SEQ ID NO 11
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 11
caggtgcagc tggtgcagtc tgggggaggc ttggtacagc ctggagggtc cctgagactc    60
tcctgtgcag cctctgattt ctatttctat gattatgaaa tgagctgggt ccgccaggct   120
ccagggaagg gtctggagtg gattggaact gtctcctata gtgggagcac ctactacaac   180
ccgtccctca agagtcgagt caccatctcc agagacaatt ccaagaacac gctgtatctg   240
caaatgaaca ccctaagagc cgaggacaca gccatgtatt actgtgcgag aggttacagc   300
tatgatgact cccgatattt tgactactgg ggccaggaa ccctggtcac cgtctcctca   360

<210> SEQ ID NO 12
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 12

Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Tyr Phe Tyr Asp Tyr
            20                  25                  30

Glu Met Ser Trp Val Arg Gln Ala Pro Gly Lys Gly Leu Glu Trp Ile
        35                  40                  45

Gly Thr Val Ser Tyr Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Met Tyr Tyr Cys Ala
                85                  90                  95

Arg Gly Tyr Ser Tyr Asp Asp Ser Arg Tyr Phe Asp Tyr Trp Gly Gln
            100                 105                 110

Gly Thr Leu Val Thr Val Ser Ser
        115                 120

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Asp or Ser
<220> FEATURE:
<221> NAME/KEY: MISC_FEATURE
<222> LOCATION: (3)..(3)
<223> OTHER INFORMATION: Xaa = Asp, Tyr or Ser
<220> FEATURE:
<221> NAME/KEY: MISC_FEATURE
<222> LOCATION: (5)..(5)
<223> OTHER INFORMATION: Xaa = Asp, Tyr or Ala
<220> FEATURE:
<221> NAME/KEY: MISC_FEATURE
<222> LOCATION: (6)..(6)
<223> OTHER INFORMATION: Xaa = Asp, Ser or Ala

<400> SEQUENCE: 13

Xaa Phe Xaa Phe Xaa Xaa Tyr Glu
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ala, Ser or Asp
<220> FEATURE:
<221> NAME/KEY: MISC_FEATURE
<222> LOCATION: (4)..(4)
<223> OTHER INFORMATION: Xaa = Met or Val

<400> SEQUENCE: 14

Xaa Tyr Glu Xaa Ser
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ile or Val
<220> FEATURE:
<221> NAME/KEY: MISC_FEATURE
<222> LOCATION: (2)..(2)
<223> OTHER INFORMATION: Xaa = Asn, Tyr or Ser
<220> FEATURE:
<221> NAME/KEY: MISC_FEATURE
<222> LOCATION: (3)..(3)
<223> OTHER INFORMATION: Xaa = His, Tyr, Gly or Thr
<220> FEATURE:
<221> NAME/KEY: MISC_FEATURE
<222> LOCATION: (6)..(6)
<223> OTHER INFORMATION: Xaa = Gly or no amino acid

```
<220> FEATURE:
<221> NAME/KEY: MISC_FEATURE
<222> LOCATION: (7)..(7)
<223> OTHER INFORMATION: Xaa = Gly or Ser

<400> SEQUENCE: 15

Xaa Xaa Xaa Ser Gly Xaa Xaa Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ile or Val
<220> FEATURE:
<221> NAME/KEY: MISC_FEATURE
<222> LOCATION: (2)..(2)
<223> OTHER INFORMATION: Xaa = Asn, Tyr or Ser
<220> FEATURE:
<221> NAME/KEY: MISC_FEATURE
<222> LOCATION: (3)..(3)
<223> OTHER INFORMATION: Xaa = His, Tyr, Gly or Thr

<400> SEQUENCE: 16

Xaa Xaa Xaa Ser Gly Ser Thr
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Glu, Tyr, Thr or Arg
<220> FEATURE:
<221> NAME/KEY: MISC_FEATURE
<222> LOCATION: (2)..(2)
<223> OTHER INFORMATION: Xaa = Ile or Val
<220> FEATURE:
<221> NAME/KEY: MISC_FEATURE
<222> LOCATION: (3)..(3)
<223> OTHER INFORMATION: Xaa = Asn, Tyr or Ser
<220> FEATURE:
<221> NAME/KEY: MISC_FEATURE
<222> LOCATION: (4)..(4)
<223> OTHER INFORMATION: Xaa = His, Tyr, Gly or Thr
<220> FEATURE:
<221> NAME/KEY: MISC_FEATURE
<222> LOCATION: (7)..(7)
<223> OTHER INFORMATION: Xaa = Gly or no amino acid
<220> FEATURE:
<221> NAME/KEY: MISC_FEATURE
<222> LOCATION: (8)..(8)
<223> OTHER INFORMATION: Xaa = Ser or Gly
<220> FEATURE:
<221> NAME/KEY: MISC_FEATURE
<222> LOCATION: (10)..(10)
<223> OTHER INFORMATION: Xaa = Thr, Tyr or Asn
<220> FEATURE:
<221> NAME/KEY: MISC_FEATURE
<222> LOCATION: (12)..(12)
<223> OTHER INFORMATION: Xaa = Asn or Ala
<220> FEATURE:
<221> NAME/KEY: MISC_FEATURE
<222> LOCATION: (13)..(13)
<223> OTHER INFORMATION: Xaa = Pro or Asp
<220> FEATURE:
```

```
<221> NAME/KEY: MISC_FEATURE
<222> LOCATION: (15)..(15)
<223> OTHER INFORMATION: Xaa = Leu or Val
<220> FEATURE:
<221> NAME/KEY: MISC_FEATURE
<222> LOCATION: (17)..(17)
<223> OTHER INFORMATION: Xaa = Ser or Gly

<400> SEQUENCE: 17

Xaa Xaa Xaa Xaa Ser Gly Xaa Xaa Thr Xaa Tyr Xaa Xaa Ser Xaa Lys
1               5                   10                  15

Xaa

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Glu, Tyr, Thr or Arg
<220> FEATURE:
<221> NAME/KEY: MISC_FEATURE
<222> LOCATION: (2)..(2)
<223> OTHER INFORMATION: Xaa = Ile or Val
<220> FEATURE:
<221> NAME/KEY: MISC_FEATURE
<222> LOCATION: (3)..(3)
<223> OTHER INFORMATION: Xaa = Asn, Tyr or Ser
<220> FEATURE:
<221> NAME/KEY: MISC_FEATURE
<222> LOCATION: (4)..(4)
<223> OTHER INFORMATION: Xaa = His, Tyr or Thr
<220> FEATURE:
<221> NAME/KEY: MISC_FEATURE
<222> LOCATION: (9)..(9)
<223> OTHER INFORMATION: Xaa = Thr, Tyr or Asn

<400> SEQUENCE: 18

Xaa Xaa Xaa Xaa Ser Gly Ser Thr Xaa Tyr Asn Pro Ser Leu Lys Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = Ser or Cys
<220> FEATURE:
<221> NAME/KEY: MISC_FEATURE
<222> LOCATION: (6)..(6)
<223> OTHER INFORMATION: Xaa = Gly, Ser or no amino acid
<220> FEATURE:
<221> NAME/KEY: MISC_FEATURE
<222> LOCATION: (7)..(7)
<223> OTHER INFORMATION: Xaa = Tyr or no amino acid
<220> FEATURE:
<221> NAME/KEY: MISC_FEATURE
<222> LOCATION: (8)..(8)
<223> OTHER INFORMATION: Xaa = Asp or Gly
<220> FEATURE:
<221> NAME/KEY: MISC_FEATURE
<222> LOCATION: (9)..(9)
<223> OTHER INFORMATION: Xaa = Asp or Gly
<220> FEATURE:
<221> NAME/KEY: MISC_FEATURE
<222> LOCATION: (11)..(11)
<223> OTHER INFORMATION: Xaa = Arg, His or Cys
```

<400> SEQUENCE: 19

Ala Arg Gly Tyr Xaa Xaa Xaa Xaa Xaa Ser Xaa Tyr Phe Asp Tyr
1               5                   10                  15

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
ggaccaggac cgggacacag                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gaacagcagg tgtactcctg                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gaggcagagc aggtagtcag                                              20

<210> SEQ ID NO 23
<211> LENGTH: 19
<212> TYPE: RNA
<213> ORGANISM: Artificial Sequence
<220> FEATURE:
<223> OTHER INFORMATION: siRNA

<400> SEQUENCE: 23
ggauauagcu uaaaccuaa                                               19

<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
caacgugguu cguggcugu                                               19

<210> SEQ ID NO 25
<211> LENGTH: 19
<212> TYPE: RNA
<213> ORGANISM: Artificial Sequence
<220> FEATURE:
<223> OTHER INFORMATION: siRNA

<400> SEQUENCE: 25
gaagaucucg gaggguuug                                               19

```
<210> SEQ ID NO 26
<211> LENGTH: 14
<212> TYPE: PRT
<213> ORGANISM: Artificial Sequence
<220> FEATURE:
<223> OTHER INFORMATION: Synthetic peptide

<400> SEQUENCE: 26

Asn Tyr His Leu Glu Asn Glu Val Ala Arg Leu Lys Lys Leu
1               5                   10
```

UNITED STATES PATENT AND TRADEMARK OFFICE
CERTIFICATE OF CORRECTION

Page 1 of 1

PATENT NO. : 11,066,479 B2
APPLICATION NO. : 16/322712
DATED : July 20, 2021
INVENTOR(S) : Ho et al.

It is certified that error appears in the above-identified patent and that said Letters Patent is hereby corrected as shown below:

In the Claims

In Claim 1, Column 71, Line 17, "complemetarity" should be --complementarity--.

In Claim 35, Column 73, Line 41, "claim claim 33" should be --claim 33--.

Signed and Sealed this
Fifteenth Day of February, 2022

Drew Hirshfeld
*Performing the Functions and Duties of the
Under Secretary of Commerce for Intellectual Property and
Director of the United States Patent and Trademark Office*